(12) United States Patent
Johnson et al.

(10) Patent No.: US 10,350,098 B2
(45) Date of Patent: Jul. 16, 2019

(54) DEVICES AND METHODS FOR CONTROLLED ENDOLUMINAL FILTER DEPLOYMENT

(71) Applicant: VOLCANO CORPORATION, San Diego, CA (US)

(72) Inventors: Eric Johnson, Woodside, CA (US); Jeremy Stigall, San Diego, CA (US); Princeton Saroha, San Diego, CA (US)

(73) Assignee: VOLCANO CORPORATION, San Diego, CA (US)

( * ) Notice: Subject to any disclaimer, the term of this patent is extended or adjusted under 35 U.S.C. 154(b) by 500 days.

(21) Appl. No.: 14/578,087

(22) Filed: Dec. 19, 2014

(65) Prior Publication Data

US 2015/0173924 A1    Jun. 25, 2015

Related U.S. Application Data

(60) Provisional application No. 61/919,573, filed on Dec. 20, 2013.

(51) Int. Cl.
   *A61F 2/966*  (2013.01)
   *A61F 2/82*   (2013.01)
   (Continued)

(52) U.S. Cl.
   CPC ........... *A61F 2/966* (2013.01); *A61F 2/01* (2013.01); *A61F 2002/011* (2013.01);
   (Continued)

(58) Field of Classification Search
   CPC .... A61F 2/2427; A61F 2/2436; A61F 2/2439; A61F 2/95; A61F 2/962; A61F 2/966;
   (Continued)

(56) References Cited

U.S. PATENT DOCUMENTS 152,652 A    6/1874   Knowlton
407,971 A    7/1889   Siersdorfer
(Continued)

FOREIGN PATENT DOCUMENTS

CN    2635045 Y    8/2004
GB    1588072      4/1981
(Continued)

OTHER PUBLICATIONS

Laroya et al.; U.S. Appl. No. 13/475,819 entitled "Retrieval Snare Device and Method," filed May 18, 2012.
(Continued)

*Primary Examiner* — Todd J Scherbel

(57) ABSTRACT

A delivery catheter having one or more securement devices can be used to control deployment of an implant from the delivery catheter. The securement device can be outwardly biased to automatically release the implant, or the securement device can be user actuated. The securement device allows the implant to be recaptured and repositioned during deployment if desired. The delivery catheter can be telescoping which allows the length and diameter of the implant to be controlled during deployment. A pullback system can be used to control deployment of the implant from the delivery catheter.

3 Claims, 77 Drawing Sheets

(51) Int. Cl.
*A61F 2/01* (2006.01)
*A61F 2/95* (2013.01)

(52) U.S. Cl.
CPC . *A61F 2002/016* (2013.01); *A61F 2002/9528* (2013.01); *A61F 2210/0014* (2013.01); *A61F 2220/0016* (2013.01); *A61F 2230/0008* (2013.01); *A61F 2230/0054* (2013.01); *A61F 2230/0067* (2013.01); *A61F 2230/0095* (2013.01)

(58) Field of Classification Search
CPC ........ A61F 2002/011; A61F 2002/9505; A61F 2002/9511; A61F 2002/9528; A61F 2002/9534; A61F 2002/9665
See application file for complete search history.

(56) References Cited

U.S. PATENT DOCUMENTS

| | | |
|---|---|---|
| 621,937 A | 3/1899 | Niemann |
| 796,910 A | 8/1905 | Hernan |
| 1,950,378 A | 3/1934 | Andrews |
| 2,163,324 A | 6/1939 | Reinhold |
| 4,046,150 A | 9/1977 | Schwartz et al. |
| 4,299,225 A | 11/1981 | Glassman |
| 4,347,846 A | 9/1982 | Dormia |
| 4,425,908 A | 1/1984 | Simon |
| 4,619,246 A | 10/1986 | Molgaard-Nielsen et al. |
| 4,727,873 A | 3/1988 | Mobin Uddin |
| 4,909,789 A | 3/1990 | Taguchi et al. |
| 4,990,151 A * | 2/1991 | Wallsten ............... A61B 17/29 606/108 |
| 4,990,156 A | 2/1991 | Lefebvre |
| 5,098,440 A | 3/1992 | Hillstead |
| 5,192,286 A | 3/1993 | Phan et al. |
| 5,234,458 A | 8/1993 | Metais |
| 5,342,371 A | 8/1994 | Welter et al. |
| 5,370,657 A | 12/1994 | Irie |
| 5,375,612 A | 12/1994 | Cottenceau et al. |
| 5,601,595 A | 2/1997 | Smith |
| 5,626,605 A | 5/1997 | Irie et al. |
| 5,683,411 A | 11/1997 | Kavteladze et al. |
| 5,725,552 A | 3/1998 | Kotula et al. |
| 5,733,294 A | 3/1998 | Forber et al. |
| 5,797,953 A | 8/1998 | Tekulve |
| 5,814,064 A | 9/1998 | Daniel et al. |
| RE36,057 E | 1/1999 | Martin |
| 5,925,060 A | 7/1999 | Forber |
| 5,944,738 A | 8/1999 | Amplatz et al. |
| 6,053,925 A | 4/2000 | Barnhart |
| 6,059,825 A | 5/2000 | Hobbs et al. |
| 6,080,182 A | 6/2000 | Shaw et al. |
| 6,099,534 A | 8/2000 | Bates et al. |
| 6,106,476 A | 8/2000 | Coral et al. |
| 6,146,404 A | 11/2000 | Kim et al. |
| 6,171,327 B1 | 1/2001 | Daniel et al. |
| 6,231,581 B1 | 5/2001 | Shank et al. |
| 6,346,116 B1 | 2/2002 | Brooks et al. |
| 6,361,545 B1 | 3/2002 | Macoviak et al. |
| 6,368,338 B1 | 4/2002 | Konya et al. |
| 6,375,670 B1 | 4/2002 | Greenhalgh |
| 6,443,972 B1 | 9/2002 | Bosma et al. |
| 6,454,775 B1 | 9/2002 | Demarais et al. |
| 6,458,145 B1 | 10/2002 | Ravenscroft et al. |
| 6,468,301 B1 | 10/2002 | Amplatz et al. |
| 6,485,502 B2 | 11/2002 | Don Michael et al. |
| 6,530,939 B1 | 3/2003 | Hopkins et al. |
| 6,537,297 B2 | 3/2003 | Tsugita et al. |
| 6,544,279 B1 | 4/2003 | Hopkins et al. |
| 6,554,849 B1 | 4/2003 | Jones et al. |
| 6,610,077 B1 | 8/2003 | Hancock et al. |
| 6,613,074 B1 | 9/2003 | Mitelberg et al. |
| 6,626,915 B2 | 9/2003 | Leveillee |
| 6,638,294 B1 | 10/2003 | Palmer |
| 6,645,152 B1 | 11/2003 | Jung et al. |
| 6,652,556 B1 | 11/2003 | VanTassel et al. |
| 6,776,770 B1 | 8/2004 | Trerotola |
| 6,783,538 B2 | 8/2004 | McGuckin, Jr. et al. |
| 6,824,545 B2 | 11/2004 | Sepetka et al. |
| 6,939,362 B2 | 9/2005 | Boyle et al. |
| 6,958,074 B2 | 10/2005 | Russell |
| 7,282,055 B2 | 10/2007 | Tsuruta |
| 7,582,100 B2 | 9/2009 | Johnson et al. |
| 7,645,292 B2 | 1/2010 | Porter |
| 7,655,013 B2 | 2/2010 | Bieneman |
| 7,695,484 B2 | 4/2010 | Wallace et al. |
| 7,713,275 B2 | 5/2010 | Greenberg et al. |
| 7,753,918 B2 | 7/2010 | Hartley et al. |
| 7,776,052 B2 | 8/2010 | Greenberg et al. |
| 7,785,343 B2 | 8/2010 | Johnson et al. |
| 7,789,892 B2 | 9/2010 | Johnson et al. |
| 7,806,906 B2 | 10/2010 | Don Michael |
| 7,854,747 B2 | 12/2010 | Johnson et al. |
| 7,875,038 B2 | 1/2011 | Que et al. |
| 8,057,506 B2 | 11/2011 | Gilson et al. |
| 8,162,974 B2 | 4/2012 | Eskuri et al. |
| 8,226,679 B2 | 7/2012 | Johnson et al. |
| 2001/0003801 A1 | 6/2001 | Strecker |
| 2001/0039432 A1 | 11/2001 | Whitcher et al. |
| 2001/0039450 A1 | 11/2001 | Pavcnik et al. |
| 2002/0004667 A1 | 1/2002 | Adams et al. |
| 2002/0022832 A1 | 2/2002 | Mikus et al. |
| 2002/0022858 A1 | 2/2002 | Demond et al. |
| 2002/0045916 A1 | 4/2002 | Gray et al. |
| 2002/0072730 A1 | 6/2002 | McGill et al. |
| 2002/0091408 A1 | 7/2002 | Sutton et al. |
| 2002/0099437 A1 | 7/2002 | Anson et al. |
| 2002/0107541 A1 | 8/2002 | Vale et al. |
| 2002/0120287 A1 | 8/2002 | Huter |
| 2002/0183783 A1 | 12/2002 | Shadduck |
| 2002/0193826 A1 | 12/2002 | McGuckin et al. |
| 2003/0040772 A1 | 2/2003 | Hyodoh et al. |
| 2003/0069596 A1 | 4/2003 | Eskuri |
| 2003/0083735 A1 | 5/2003 | Denardo et al. |
| 2003/0097094 A1 | 5/2003 | Ouriel et al. |
| 2003/0097114 A1 | 5/2003 | Ouriel et al. |
| 2003/0130681 A1 | 7/2003 | Ungs |
| 2003/0130684 A1 | 7/2003 | Brady et al. |
| 2003/0171774 A1 | 9/2003 | Freudenthal et al. |
| 2003/0171803 A1 | 9/2003 | Shimon |
| 2003/0187495 A1 | 10/2003 | Cully et al. |
| 2003/0208224 A1 | 11/2003 | Broome |
| 2003/0212429 A1 | 11/2003 | Keegan et al. |
| 2004/0093017 A1 | 5/2004 | Chanduszko |
| 2004/0122466 A1 | 6/2004 | Bales |
| 2004/0147939 A1* | 7/2004 | Rabkin ............... A61F 2/95 606/108 |
| 2004/0153118 A1 | 8/2004 | Clubb et al. |
| 2004/0199201 A1 | 10/2004 | Kellett et al. |
| 2004/0220608 A1 | 11/2004 | D'Aquanni et al. |
| 2004/0236368 A1 | 11/2004 | McGuckin et al. |
| 2004/0254601 A1 | 12/2004 | Eskuri |
| 2005/0080481 A1 | 4/2005 | Madda et al. |
| 2005/0107822 A1 | 5/2005 | WasDyke |
| 2005/0154416 A1 | 7/2005 | Herweck et al. |
| 2006/0020285 A1 | 1/2006 | Niermann |
| 2006/0020286 A1 | 1/2006 | Niermann |
| 2006/0069405 A1 | 3/2006 | Schaeffer et al. |
| 2006/0100658 A1 | 5/2006 | Obana et al. |
| 2006/0111770 A1 | 5/2006 | Pavcnik et al. |
| 2006/0149312 A1 | 7/2006 | Arguello et al. |
| 2006/0149313 A1 | 7/2006 | Arguello et al. |
| 2006/0195137 A1 | 8/2006 | Sepetka et al. |
| 2006/0229638 A1 | 10/2006 | Abrams et al. |
| 2006/0241677 A1 | 10/2006 | Johnson et al. |
| 2006/0241678 A1 | 10/2006 | Johnson et al. |
| 2006/0241679 A1 | 10/2006 | Johnson et al. |
| 2006/0253148 A1 | 11/2006 | Leone et al. |
| 2007/0112371 A1 | 5/2007 | Cangialosi et al. |
| 2007/0123932 A1 | 5/2007 | Gray et al. |
| 2007/0239254 A1* | 10/2007 | Chia ............... A61F 2/2436 623/1.11 |
| 2008/0004687 A1 | 1/2008 | Barbut et al. |

(56) References Cited

U.S. PATENT DOCUMENTS

| | | |
|---|---|---|
| 2008/0021497 A1 | 1/2008 | Johnson et al. |
| 2008/0033482 A1 | 2/2008 | Kusleika |
| 2008/0086149 A1 | 4/2008 | Diamant et al. |
| 2008/0147111 A1 | 6/2008 | Johnson et al. |
| 2009/0326575 A1 | 12/2009 | Galdonik et al. |
| 2010/0185231 A1 | 7/2010 | Lashinski |
| 2010/0191276 A1 | 7/2010 | Lashinski |
| 2010/0268265 A1 | 10/2010 | Krolik et al. |
| 2010/0318115 A1 | 12/2010 | Chanduszko et al. |
| 2010/0324590 A1 | 12/2010 | Johnson et al. |
| 2011/0034718 A1 | 2/2011 | Nakazawa |
| 2011/0264106 A1 | 10/2011 | Taube et al. |
| 2011/0282379 A1 | 11/2011 | Lee et al. |
| 2012/0010650 A1 | 1/2012 | Sos |
| 2012/0179196 A1 | 7/2012 | Johnson et al. |
| 2013/0012981 A1 | 1/2013 | Johnson et al. |
| 2013/0035715 A1 | 2/2013 | Johnson et al. |
| 2013/0184741 A1 | 7/2013 | Laroya et al. |
| 2013/0184744 A1 | 7/2013 | Johnson et al. |
| 2013/0190804 A1 | 7/2013 | Johnson et al. |
| 2013/0231696 A1 | 9/2013 | Johnson et al. |
| 2013/0238010 A1 | 9/2013 | Johnson et al. |
| 2013/0267991 A1 | 10/2013 | Johnson et al. |
| 2013/0282043 A1 | 10/2013 | Johnson et al. |
| 2013/0282044 A1 | 10/2013 | Johnson et al. |
| 2013/0282045 A1 | 10/2013 | Johnson et al. |
| 2013/0289519 A1 | 10/2013 | Johnson et al. |
| 2013/0289609 A1 | 10/2013 | Johnson et al. |
| 2013/0289610 A1 | 10/2013 | Johnson et al. |
| 2013/0289611 A1 | 10/2013 | Johnson et al. |
| 2013/0296918 A1 | 11/2013 | Johnson et al. |
| 2014/0277089 A1* | 9/2014 | Goode ............... A61F 2/01 606/200 |
| 2014/0343598 A1 | 11/2014 | Johanson et al. |
| 2014/0350593 A1 | 11/2014 | Laroya et al. |

FOREIGN PATENT DOCUMENTS

| | | |
|---|---|---|
| JP | 10-509623 | 9/1998 |
| WO | WO 01/49185 A1 | 7/2001 |
| WO | WO 02/02162 A2 | 1/2002 |
| WO | WO 2005/102211 A1 | 11/2005 |
| WO | WO 2006/034233 A1 | 3/2006 |
| WO | WO 2009/086482 A1 | 7/2009 |
| WO | WO 2012/003369 A2 | 1/2012 |
| WO | 2012/038550 * | 3/2012 |
| WO | WO 2012/031149 A1 | 3/2012 |
| WO | WO 2012/092377 A1 | 7/2012 |
| WO | WO 2012/118696 A1 | 9/2012 |

OTHER PUBLICATIONS

Johnson et al.; U.S. Appl. No. 14/574,203 entitled "Filter support members," filed Dec. 17, 2014.

Johnson et al.; U.S. Appl. No. 14/575,935 entitled "Extended anchor endoluminal filter," filed Dec. 18, 2014.

Johnson et al.; U.S. Appl. No. 62/090,580 entitled "Endoluminal filter design variations," filed Dec. 11, 2014.

Johnson et al.; U.S. Appl. No. 61/785,204 entitled "Filters with echogenic characteristics," filed Mar. 14, 2013.

Johnson et al.; U.S. Appl. No. 61/785,955 entitled "Endoluminal filter having enhanced echogenic properties," filed Mar. 14, 2013.

Johnson et al.; U.S. Appl. No. 14/581,638 entitled "Treatment structure and methods of use," filed Dec. 23, 2014.

Kahraman et al.; The Diameters of the Aorta and Its Major Branches in Patients with Isolated Coronary Artery Ectasia; Tex Heart Inst J.; vol. 33, No. 4: pp. 463-468; Oct. 2006.

Millward, Steven F.; Temporary and retrievable inferior vena cava filters; JVIR; vol. 9; No. 3; pp. 381-387, May/Jun. 1998.

Siskin, Gary P.; Inferior Vena Cava Filters; eMedicine; Sep. 7, 2004.

Streiff, Michael B.; Vena caval filters; a comprehensive review; Blood; vol. 95; No. 12; pp. 3669-3677; Jun. 15, 2000.

* cited by examiner

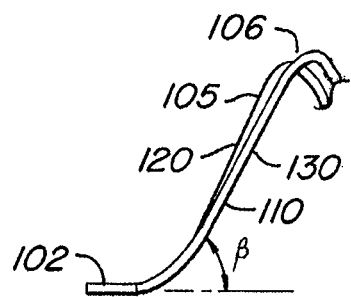
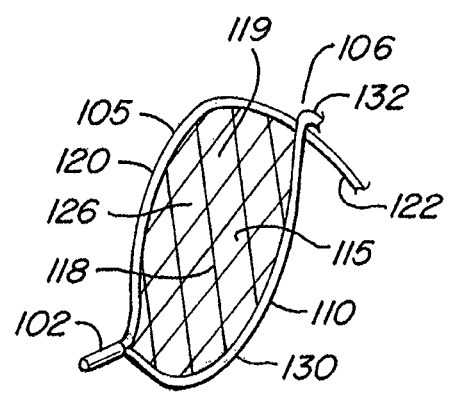
FIG. 9A
FIG. 9B
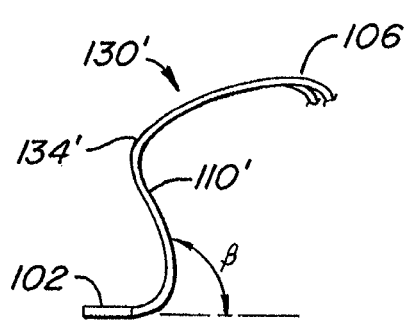
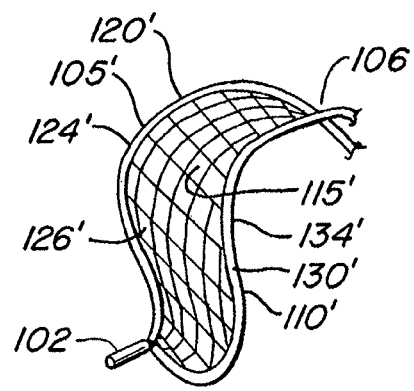
FIG. 10A
FIG. 10B

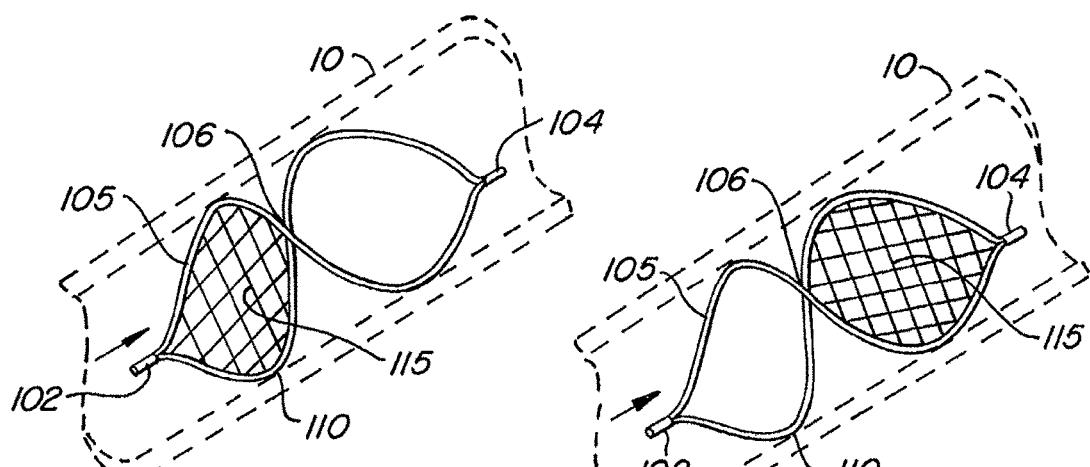
FIG. 13A
FIG. 13B
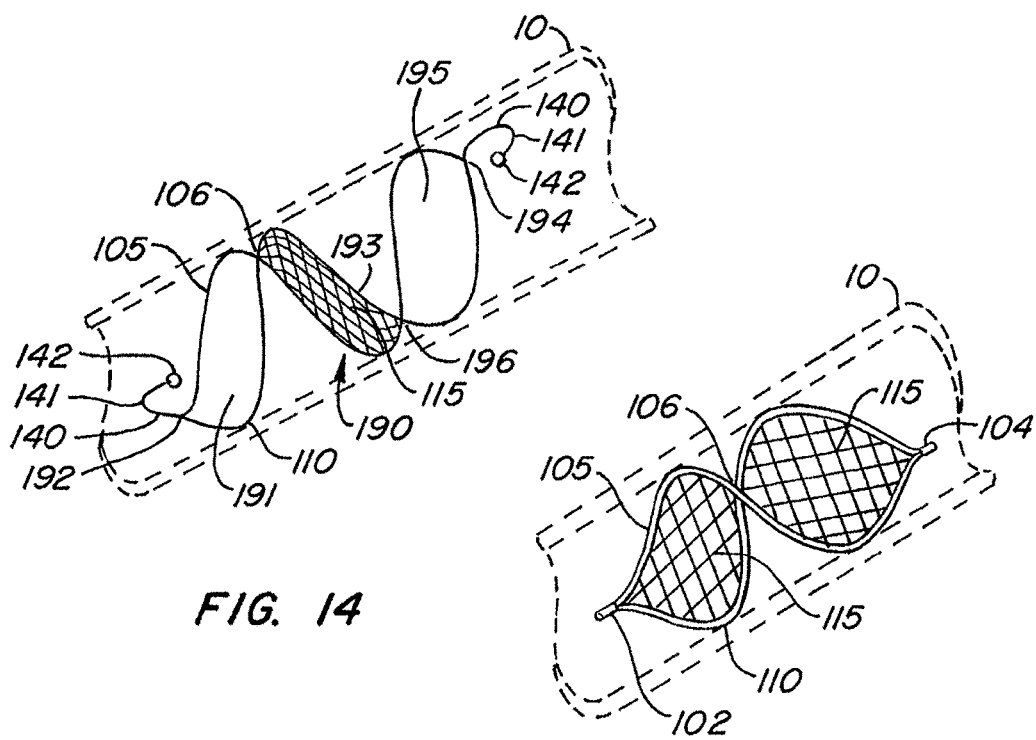
FIG. 14
FIG. 13C

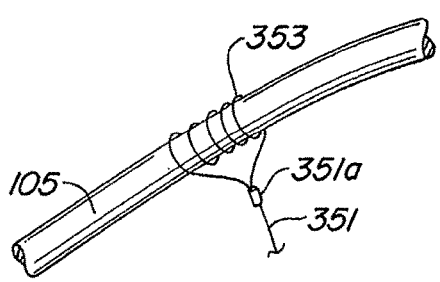
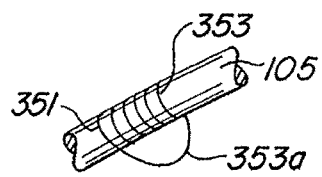
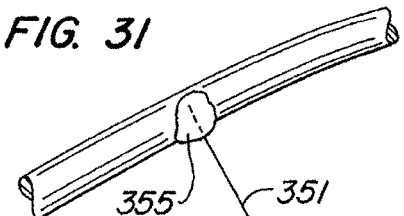
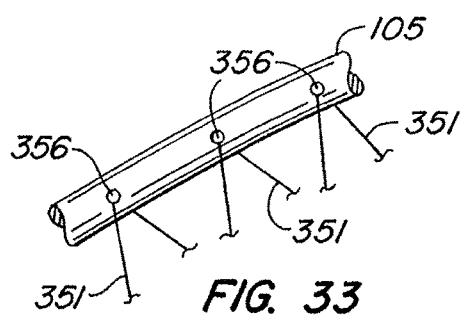
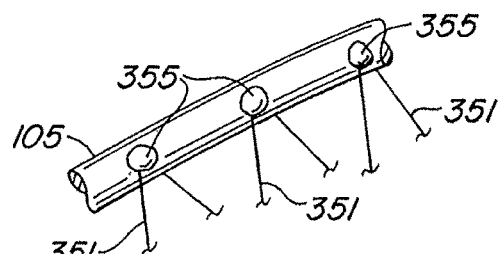
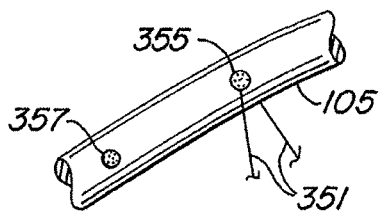
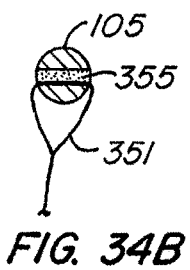
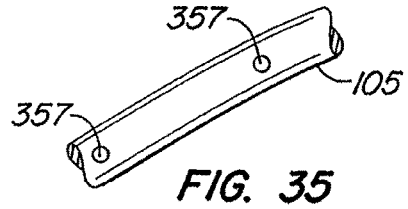
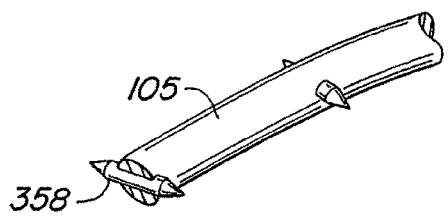
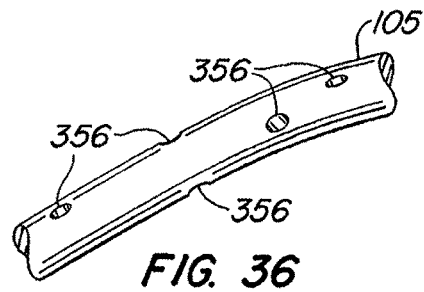

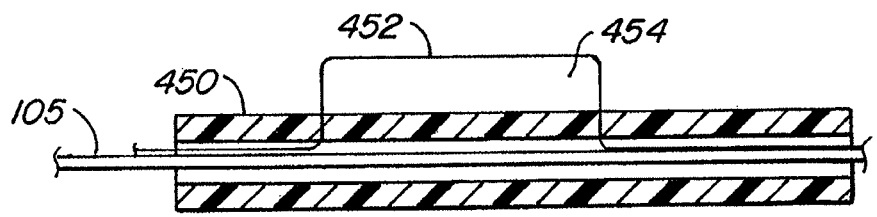
FIG. 50
FIG. 51A
FIG. 51B

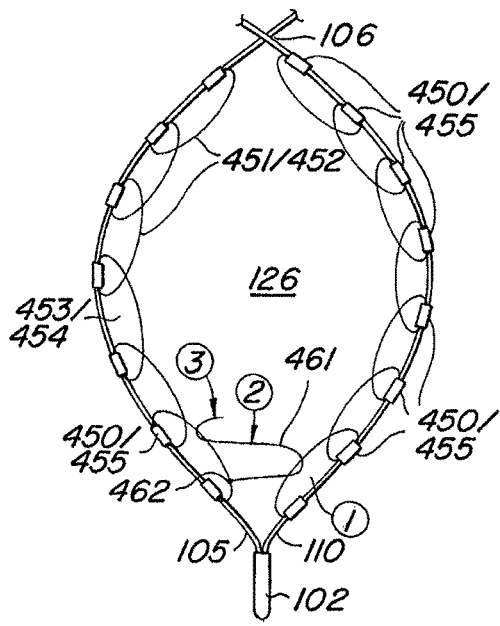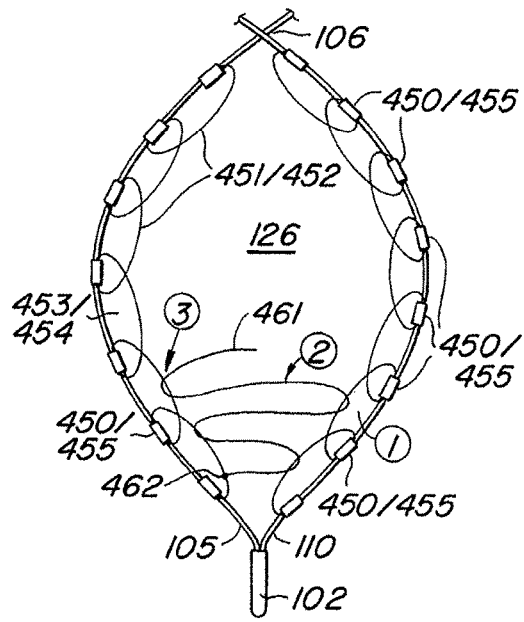
FIG. 52A    FIG. 52B
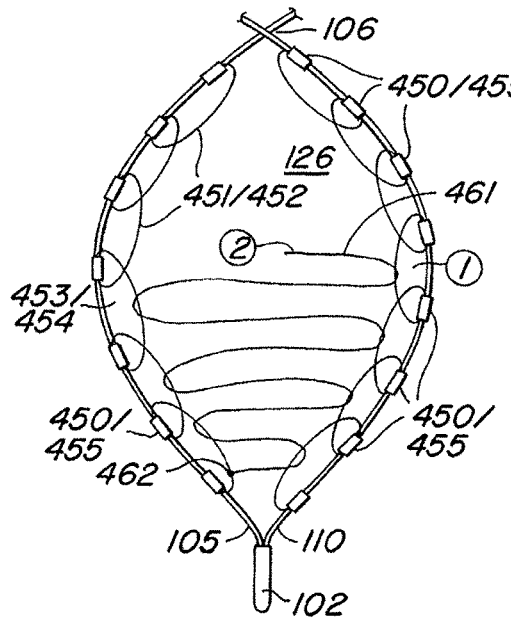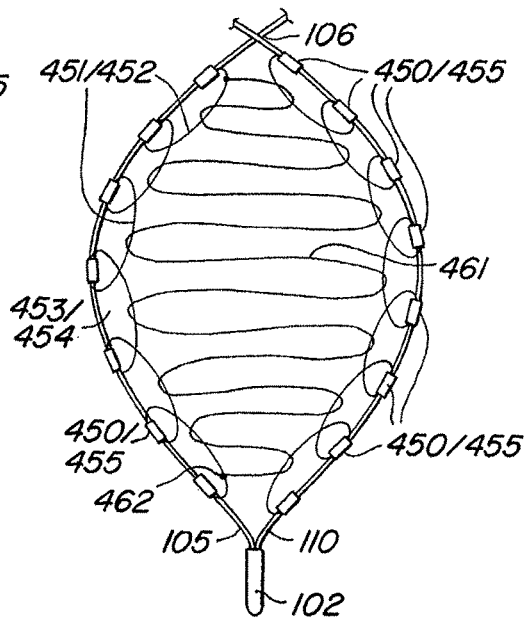
FIG. 52C    FIG. 52D

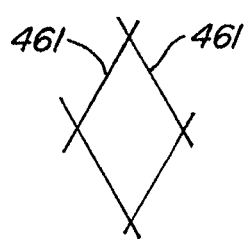 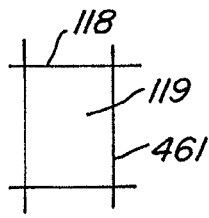 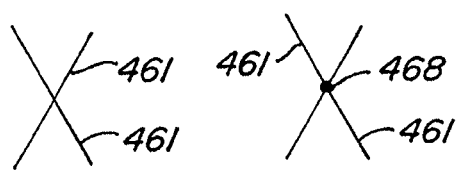
FIG. 54A  FIG. 54B  FIG. 54C  FIG. 55A
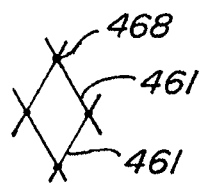 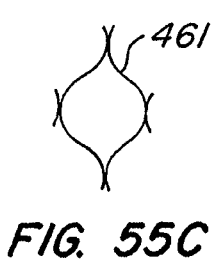 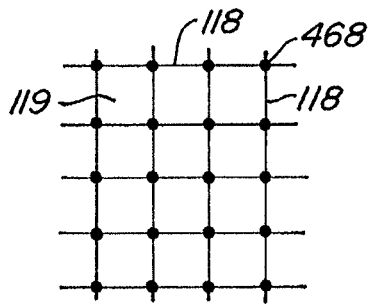
FIG. 55B  FIG. 55C  FIG. 55D
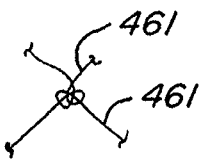 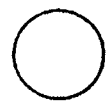 
FIG. 55E  FIG. 60A  FIG. 60B
 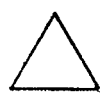 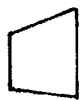
FIG. 60C  FIG. 60D  FIG. 60E

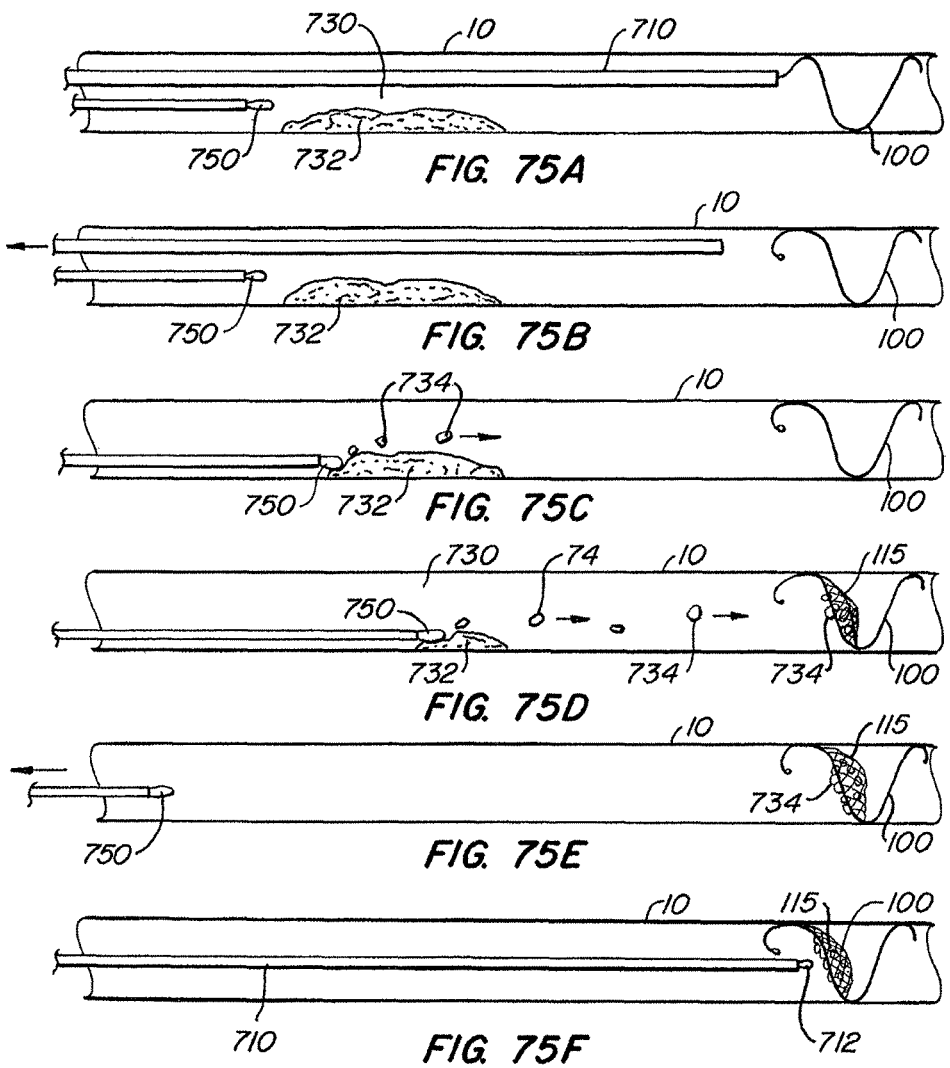

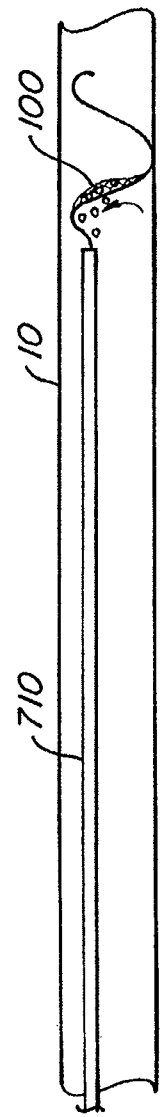
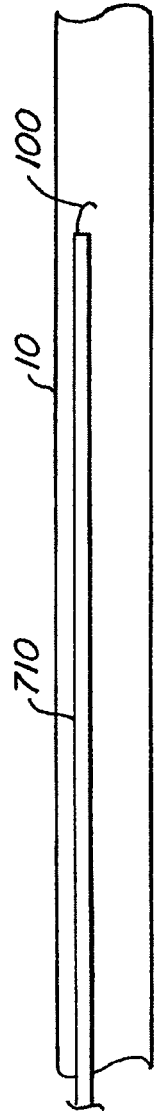
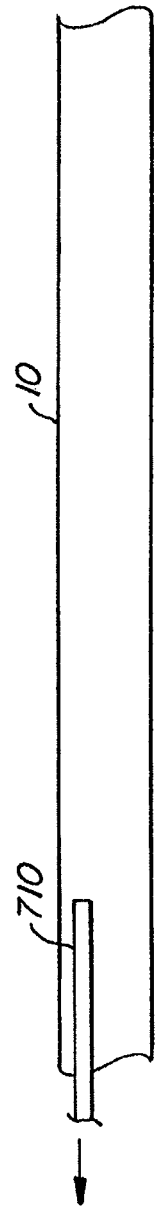
FIG. 75G
FIG. 75H
FIG. 75I

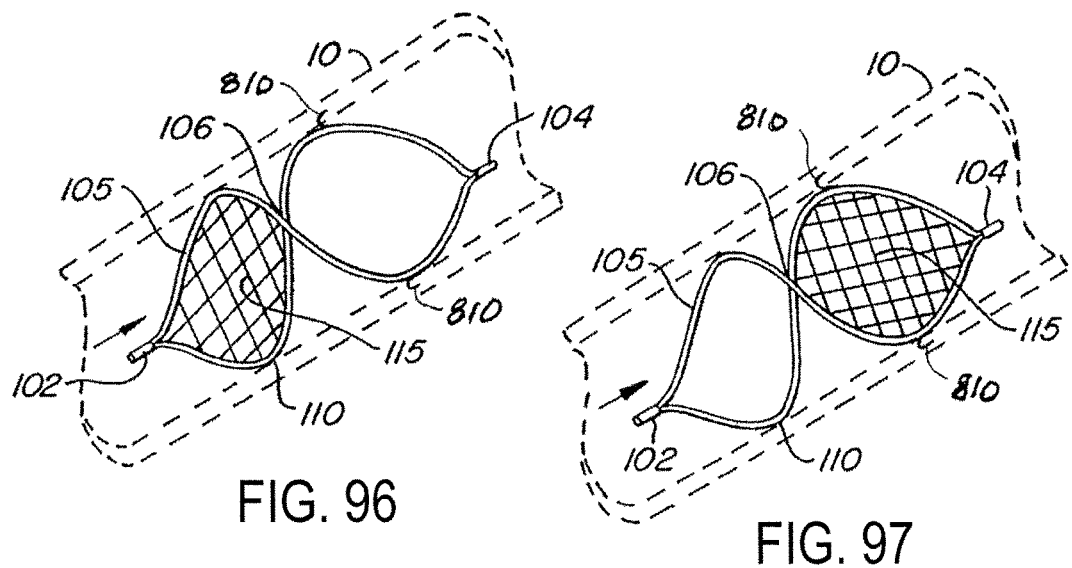
FIG. 96
FIG. 97
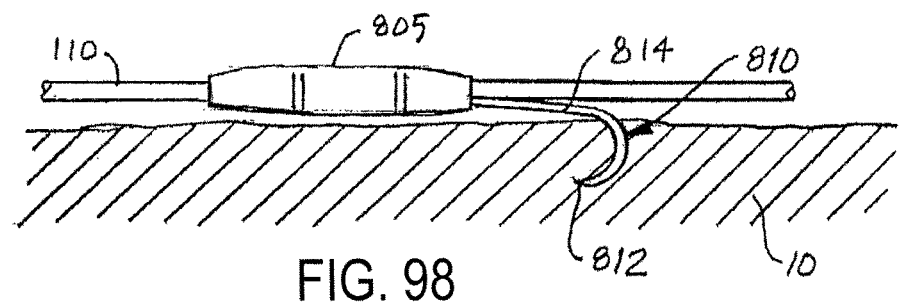
FIG. 98
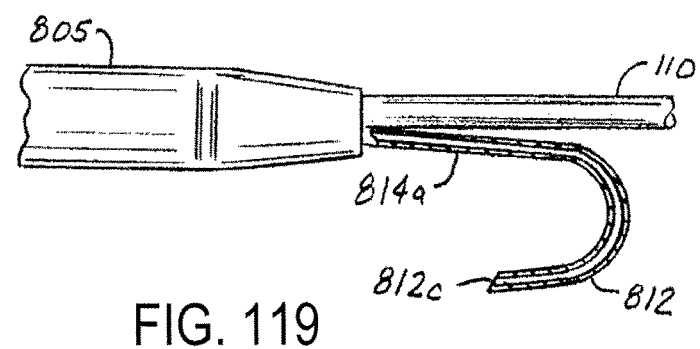
FIG. 119

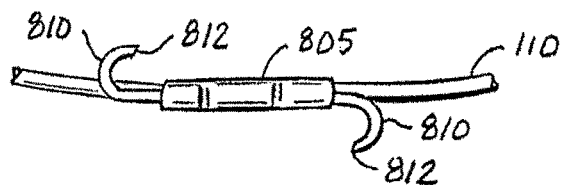
FIG. 104C
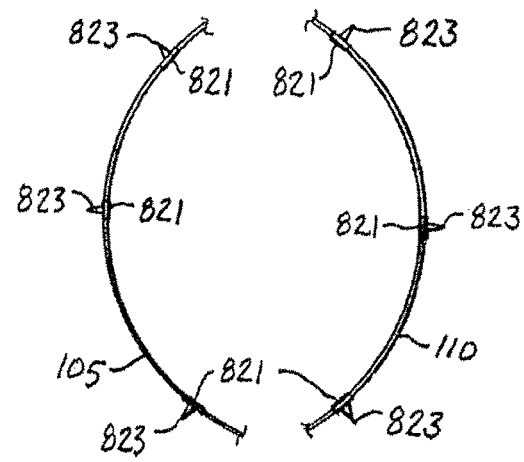
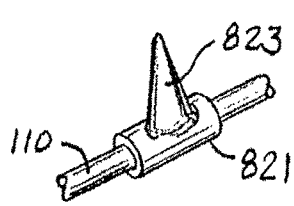
FIG. 107A
FIG. 107B
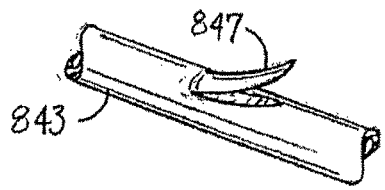
FIG. 108
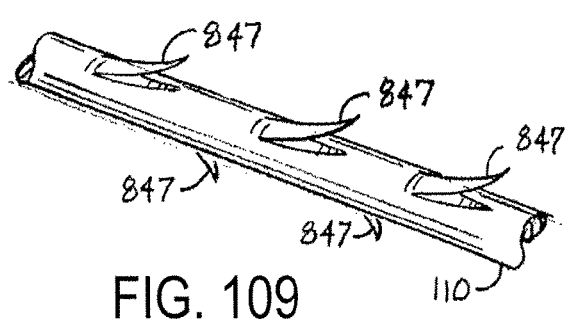
FIG. 109
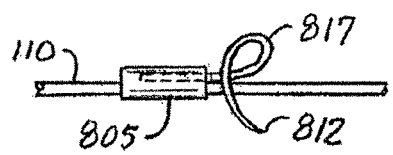
FIG. 105
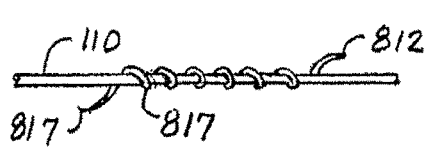
FIG. 106

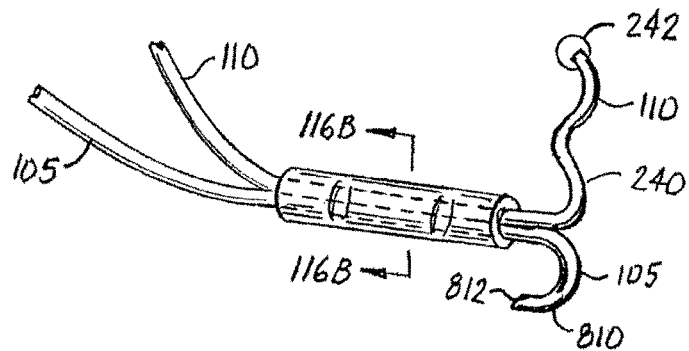
FIG. 116A
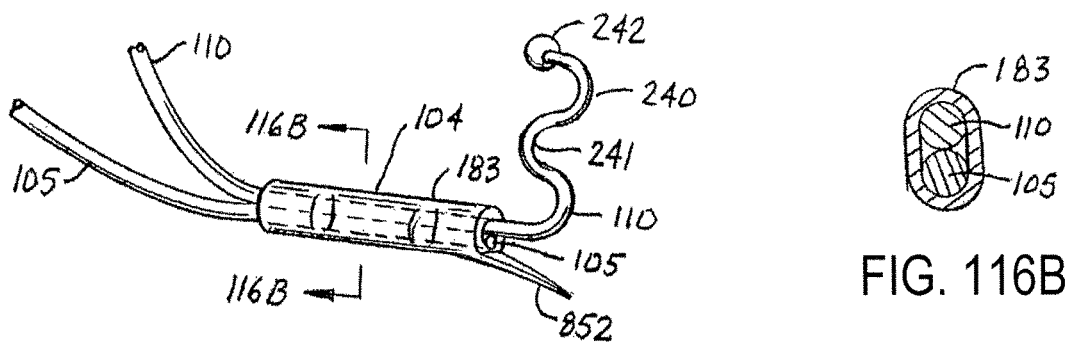
FIG. 117A
FIG. 116B
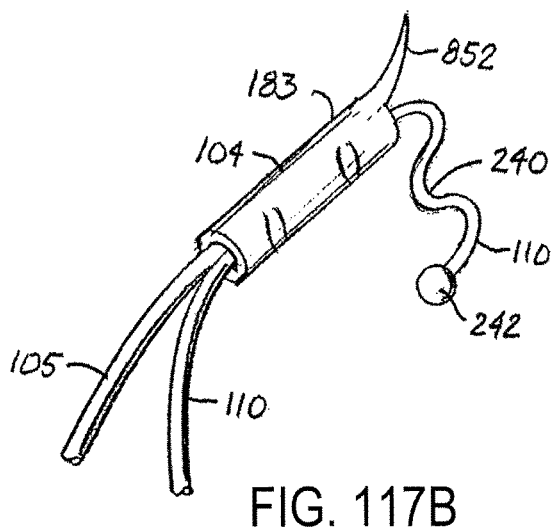
FIG. 117B

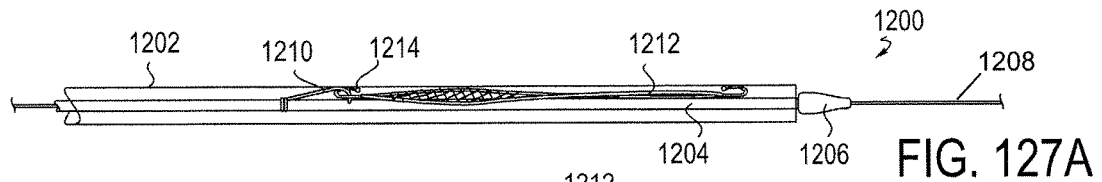
FIG. 127A
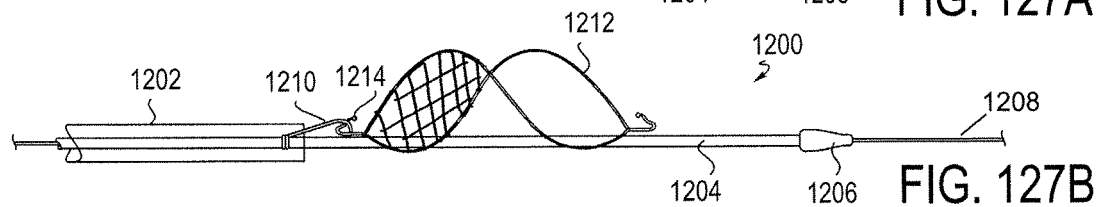
FIG. 127B
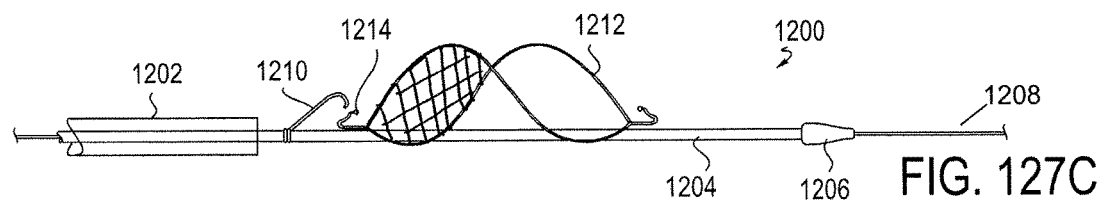
FIG. 127C
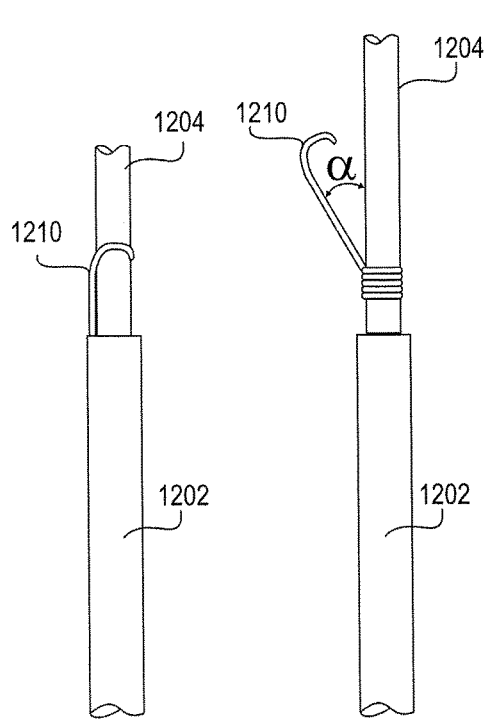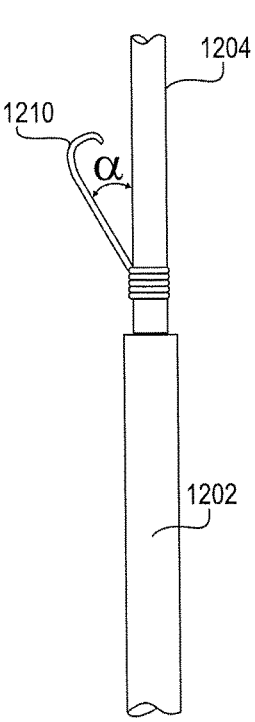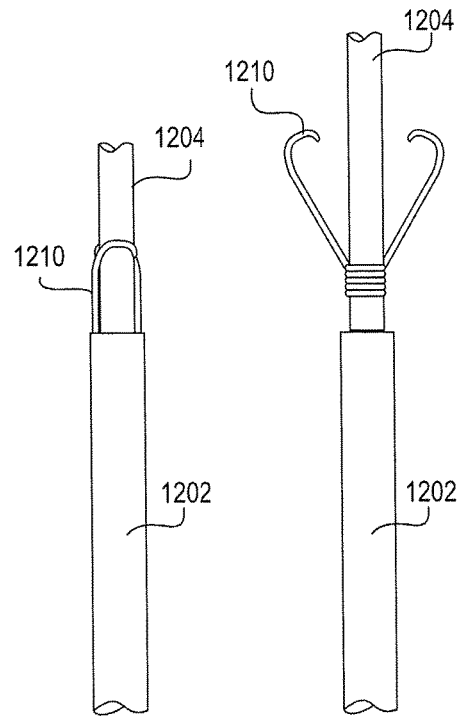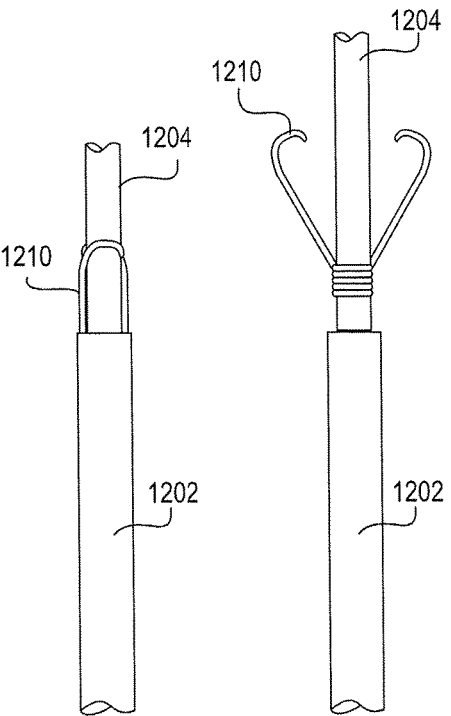
FIG. 128A   FIG. 128B   FIG. 129A   FIG. 129B

DEVICES AND METHODS FOR CONTROLLED ENDOLUMINAL FILTER DEPLOYMENT

CROSS REFERENCE TO RELATED APPLICATIONS

This application claims the benefit of U.S. Provisional Patent Application No. 61/919,573, filed Dec. 20, 2013, entitled "SECUREMENT DEVICE FOR CONTROLLED ENDOLUMINAL FILTER DEPLOYMENT".

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate generally to delivery catheters and methods of deploying an implant using a delivery catheter, and more specifically, to delivery catheters having a securement device for controllably deploying an implant.

BACKGROUND

Various endoluminal implants, such as stents and vena cava filters, are placed within a body lumen to treat or prevent various diseases or conditions. Precise placement of the implant within the lumen may be important for the implant to function optimally. During deployment, as the implant is initially being deployed, it may be determined that the initial placement of the implant is suboptimal and needs to be adjusted.

Accordingly, it would be desirable provide a delivery catheter that facilitates controlled deployment of the implant and allows the implant to be repositioned during deployment.

SUMMARY OF THE DISCLOSURE

The present invention relates generally to delivery catheters and methods of deploying an implant using a delivery catheter, and more specifically, to delivery catheters having a securement device for controllably deploying an implant.

In some embodiments, a delivery catheter for deploying an implant with a retrieval feature is provided. The delivery catheter can include a retractable outer sheath having a lumen; an inner sheath disposed within the lumen of the outer sheath, the inner sheath having a lumen configured to receive a guidewire; and an outwardly biased securement device attached to a distal portion of the inner sheath, the outwardly biased securement device configured to reversibly engage the retrieval feature of the implant, wherein the outwardly biased securement device is held in a closed configuration when the retractable outer sheath covers the outwardly biased securement device, and wherein the outwardly biased securement device adopts an open configuration for releasing the retrieval feature when the outer sheath is completely retracted past the outwardly biased securement device.

In some embodiments, wherein the outwardly biased securement device comprises a hook. In some embodiments, the outwardly biased securement device comprises a jaw.

In some embodiments, a delivery catheter for deploying an implant with a retrieval feature is provided. The delivery catheter can include a retractable outer sheath having a lumen; an inner sheath disposed within the lumen of the outer sheath, the inner sheath having a lumen configured to receive a guidewire; and a user actuated securement device attached to a distal portion of the inner sheath, the user actuated securement device configured to reversibly engage the retrieval feature of the implant.

In some embodiments, the user actuated securement device comprises a jaw. In some embodiments, the user actuated securement device comprises a loop of suture or wire.

In some embodiments, a delivery catheter for deploying an implant with a proximal retrieval feature and a distal retrieval feature is provided. The delivery catheter can include a retractable outer sheath having a lumen; an inner sheath slidably disposed within the lumen of the outer sheath, the inner sheath having a lumen; a guidewire sheath slidably disposed within the lumen of the inner sheath, the guidewire sheath having a lumen configured to receive a guidewire; a distal securement device located on the distal end of the guidewire sheath, the distal securement device configured to engage the distal retrieval feature of the implant; and a proximal securement device located on the distal end of the inner sheath, the proximal securement device configured to engage the proximal retrieval feature of the implant.

In some embodiments, both the proximal securement device and the distal securement device are user actuated.

In some embodiments, the proximal securement device comprises a loop of suture or wire and a port in the inner sheath, and the distal securement device comprises a loop or suture or wire and a port in the guidewire sheath.

In some embodiments, a pullback system for deploying an implant is provided. The system comprises a sliding clip configured to slide along a rail; a fixed clip in alignment with the sliding clip, the sliding clip configured to receive a retractable outer sheath of a delivery catheter, the retractable outer sheath having a lumen, the fixed clip configured to receive an inner sheath slidably disposed within the lumen of the outer sheath, the inner sheath having a lumen, a guidewire sheath slidably disposed within the lumen of the inner sheath, the guidewire sheath having a lumen configured to receive a guidewire, wherein the sliding clip is configured to move relative to the fixed clip; and a pullback grip attached to the sliding clip and configured to control movement of the sliding clip.

The sliding clip can comprise a recess configured to receive the outer sheath or a feature of the outer sheath. The fixed clip can comprise a recess configured to receive the inner sheath. The system can comprise a housing with a hinged cover. The system can comprise a plurality of pieces configured to be attached around the delivery catheter. The rail can comprise a locking feature or safety feature (e.g., a notch). The system can comprise a scale configured to indicate deployment information at a given pullback position. The system can be disposable.

In some embodiments, a method of deploying an implant is provided. The method comprises positioning a delivery catheter within the system comprising a retractable outer sheath having a lumen, an inner sheath slidably disposed within the lumen of the outer sheath, the inner sheath having a lumen, a guidewire sheath slidably disposed within the lumen of the inner sheath, the guidewire sheath having a lumen configured to receive a guidewire, the positioning comprising attaching the inner sheath to a fixed clip; attaching the outer sheath to a sliding clip in alignment with the fixed clip and configured to slide along a rail relative to the fixed clip; and pulling the sliding clip towards the fixed clip, thereby pulling the outer sheath relative to the inner sheath to expose at least a portion of the implant.

The method can further comprise snapping components of the system around the delivery catheter. The method can comprise positioning components of the outer sheath within a recess of the sliding clip. The method can comprise positioning components of the inner sheath within a recess of the fixed clip.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 9A and 9B illustrate various aspects of a generally planer support frame;

FIGS. 10A and 10B illustrate various aspects of a non-planer support frame;

FIGS. 11-13C illustrate various aspects of and configurations for material capture structures;

FIGS. 30-53D illustrate several alternatives techniques for joining material capture structures to support frames and forming filtering structures;

FIGS. 54A-65F illustrate several alternative filtering structures;

FIGS. 75A-78F illustrate several exemplary methods of using a filtering device;

FIGS. 96 and 97 illustrate filter devices with fixation elements in use within a lumen with the filtering structure in a upstream (FIG. 96) and downstream (FIG. 97) positions;

FIG. 98 illustrates a fixation element engaged with the side wall of lumen;

FIG. 104C illustrates a double ended fixation element with different tip orientations attached to an elongate body;

FIGS. 105 and 106 illustrate tissue anchor embodiments having an end raised above the support member;

FIG. 107A illustrates a tissue anchor attached to a tube that is attached to a support member;

FIG. 107B illustrates a plurality of the tissue anchors illustrated in FIG. 107A positioned along a pair of support structures;

FIG. 108 illustrates tissue anchors formed in a tube that is placed over an elongate body or other portion of a filtering device;

FIG. 109 illustrates tissue anchors formed by cutting into an elongate body;

FIG. 116A illustrates a perspective view of one end of a filtering device where the ends of elongate bodies pass through the securing or attachment feature and are formed into a retrieval feature and a tissue engagement element;

FIG. 116B is a section view through the securing or attachment feature shown in FIG. 116A;

FIGS. 117A and 117B illustrate perspective and bottom up views respectively of one end of a filtering device where the end of one elongate body pass through the securing or attachment feature and is formed into a retrieval feature and a tissue engagement element is formed in a portion of the securing or attachment feature;

FIG. 119 illustrates an alternative embodiment of the tissue engagement element of FIG. 98 with the addition of a hollowed tip portion;

FIGS. 127A-127C illustrate an embodiment of a delivery catheter with a securement device.

FIGS. 128A and 128B illustrate an embodiment of a securement device.

FIGS. 129A and 129B illustrate another embodiment of a securement device.

DETAILED DESCRIPTION

Figure 1A:
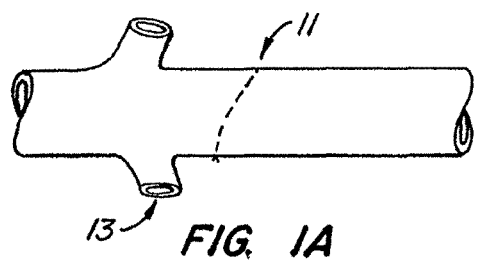
FIGS. 1A-1H illustrate various prior art filters.
Figure 1B:
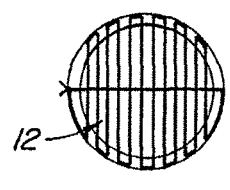
Figure 1C:
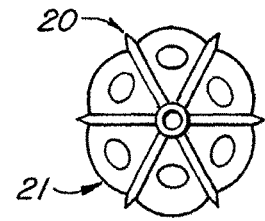
Figure 1D:
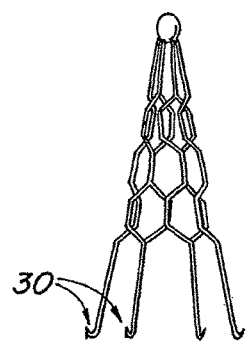
Figure 1E:
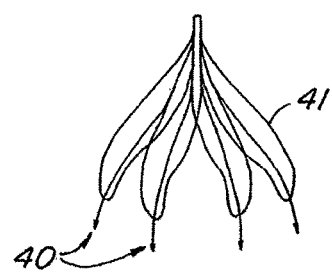
Figure 1F:
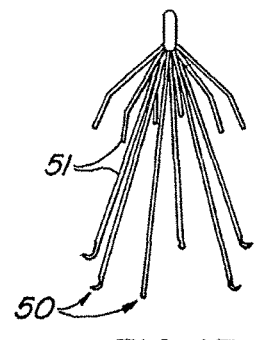
Figure 1G:
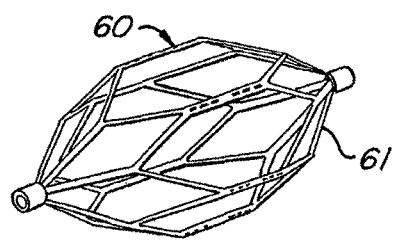
Figure 1H:
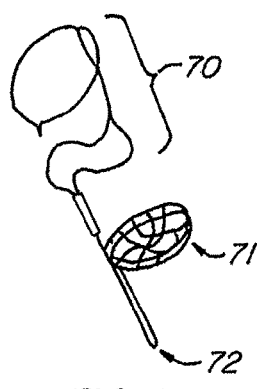

There remains a clinical need for improved endoluminal filter devices and methods. Improved endoluminal filter devices provide effective filtration over a range of lumen sizes and are easy to deploy into and retrieve from a lumen. In addition, improved endoluminal filter devices minimize thrombosis formation or tissue ingrowth on the device and are resistant to migration along the lumen. Embodiments of the filter devices of the present invention provide many and in some cases all of the features of improved endoluminal filters and have a number of uses such but are not limited to: embolic protection, thrombectomy, vessel occlusion, and tethered or untethered distal protection. Additional description of these filters is disclosed in U.S. Publication No. 2013/0012981, PCT Publication No. WO2013/106746, U.S. Provisional Application No. 61/785,204, and U.S. Provisional Application No. 61/785,955, each of which is herein incorporated by reference in its entirety.

Several embodiments of the present invention provide improved filtration devices that are durable, provide effective and nearly constant filter capacity over a range of lumen sizes and are easily delivered and removed from a lumen via either end of the device. Additionally, embodiments of the present invention can be delivered into and retrieved from a lumen using minimally invasive surgical techniques. One aspect of an embodiment of the present invention is the construction of support structure elements using a shape memory material. The shape memory material may have a pre-shaped form that ensures the support elements are uniformly collapsible and, when deployed, provides a pre-defined range of controllable force against the lumen wall without use of hooks or barbs. Alternatively, hooks barbs, or other fixation elements or devices may be used in conjunction with an embodiment of a filtering device as described below.

The elongate support structure elements are configured to collapse and expand with natural vessel movements while maintaining constant apposition with the vessel wall. One result is that the support structure shape and size track to vessel movements. As a result, the filter density and capacity of embodiments of the present invention remain relatively independent of changes in vessel size. Moreover, the self centering aspect of the support structure ensures the filtration device provides uniform filtration across the vessel diameter. As such, embodiments of the present invention provide generally constant filtration capacity of the device is maintained across the entire vessel lumen and during vessel contractions and expansions.

Uniform filter capacity is a significant improvement over conventional devices. Conventional devices typically have a filter capacity that varies radially across a lumen. The radial variation in filter capacity usually results from the fact that conventional filtration elements have a generally wider spacing at the periphery of the lumen and closer spacing along the central lumen axis. The result is that larger emboli can escape along the lumen periphery. During vessel expansions and contractions, the radial variations in filter capacity are exacerbated in conventional devices.

Another advantage of some embodiments of the present invention is that when released from a constrained state (i.e., within a delivery sheath), the device assumes a pre-determined form with elongate support members that extend along and self center the device in the vessel. These elongate support members exert atraumatic radial force against the vessel wall to prevent or minimize device migration. In some embodiments, radial forces generated by the elongate support members work in cooperation with hooks, barbs or other fixation devices to secure the device within the vessel. Hooks, barbs or other fixation devices or elements may be used as an added precaution against migration of the filtering device while in a lumen. When device retrieval is initiated, the uniformly collapsible form of the elongate support members causes the elongate support members to pull away from the vessel wall as the device is being re-sheathed. The movement of the elongate members away from the vessel wall facilitates the atraumatic removal of the device from the vessel wall. Additionally, in those embodiments having hooks, barbs or other fixation devices or elements, elongate member movement during retrieval also facilitates withdrawal of the fixation elements from the lumen wall.

Additional embodiments of the present invention may include a retrieval feature on one or both ends of the device. The use of retrieval features on both ends of the device allows deployment, repositioning and removal of the device to be accomplished from either end of the device. As a result, the use of retrieval features on both ends of the device enables both antegrade or retrograde approaches to be used with a single device. The retrieval feature may be integral to another structural member or a separate component. In some embodiments, the retrieval feature is collapsible and may have a curved shape or a generally sinusoidal shape. Additional aspects of retrieval features are described below.

General Principals and Construction

Figure 2A:
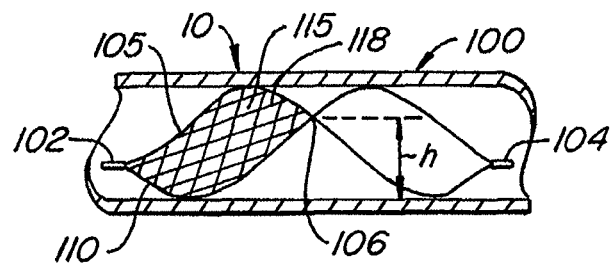
FIGS. 2A-2C illustrate the response of a filtering device to changes in lumen size.

FIG. 2A illustrates an embodiment of a filtering device 100 of the present invention positioned within a lumen 10. The lumen 10 is cut away to show the position of filter 100 deployed into within a lumen and in contact with the lumen wall. The filter 100 includes a first elongate member 105 and a second elongate member 110. The elongate members are joined to form ends 102, 104. The elongate members cross but are not joined to one another at crossover 106. In one embodiment, the elongate members have first and second sections. First sections extend between the end 102 and the crossover 106 and the second sections extend from the crossover 106 to the second end 104. While some embodiments contact the lumen in different ways, the illustrated embodiment has the ends 102, 104 against one side of the lumen interior wall while the crossover 106 contacts the other side of the lumen interior wall with the elongate bodies in constant or nearly constant apposition along the lumen interior wall between the ends 102, 104.

Material (i.e., thrombus, plaque and the like) flowing through the lumen 10 of a size larger than the filtering size of the material capture structure 115 is captured between or cut down by the filaments 118. In the illustrated embodiment of FIG. 2A, the material capture structure 115 is supported by a rounded frame formed by the elongate members 105, 110 formed between the end 102 and the crossover 106. Another rounded frame formed between the crossover 106 and the second end 104 and could also be used to support a material capture structure of the same or different construction and filter capacity of the a material capture structure 115. As such, a material removal structure supported by one rounded frame may be configured to remove material of a first size and the material removal structure supported a the other rounded frame may be configured to remove material of a second size. In one embodiment, the material removal structure in the upstream rounded frame removes larger size debris than material removal structure in the downstream rounded frame. Also illustrated in FIGS. 2A-2C is how the filter cells 119 that make up the material capture structure is 115 maintain their size and shape relatively independent of movement of the first and second structural members 105, 110 over a physiological range of vessel diameters.

Figure 2B:
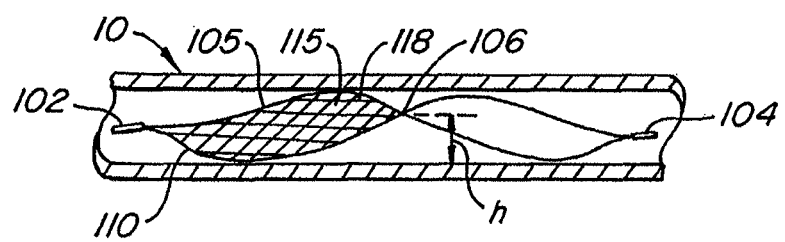
Figure 2C:
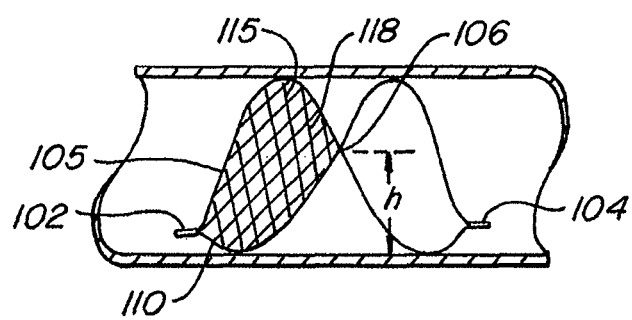

FIGS. 2B and 2C illustrate how the elongate support structure elements of embodiments of the present invention are configured to collapse and expand with natural vessel movements while maintaining constant apposition with the vessel wall. FIGS. 2A, 2B and 2C also illustrate how devices according to embodiments of the present invention are both radially and axially elastic. In response to vessel size changes, ends 102, 104 move out as the vessel size decreases (FIG. 2B) and then move in as the vessel size increases (FIG. 2C). In addition, the device height "h" (measured from the lumen wall in contact with ends 102, 104 to crossover) also changes. Device height "h" changes in direct relation to changes in vessel diameter (i.e., vessel diameter increases will increase device height "h"). As such, device height ("h") in FIG. 2C is greater than device height ("h") in FIG. 2A which is in turn greater than the device height ("h") in FIG. 2B.

FIGS. 2A, 2B and 2C also illustrate how a single sized device can be used to accommodate three different lumen diameters. FIG. 2C illustrates a large lumen, FIG. 2A a medium sized lumen and FIG. 2B a small sized lumen. As these figures make clear, one device can adapt to cover a range of vessel sizes. It is believed that only 3 device sizes are needed to cover the range of human vena cava interior diameters that range from approximately 12-30 mm with an average interior diameter of 20 mm. Also illustrated is the static or nearly static filter capacity of the material capture structure 115. In each different vessel size, the material capture structure 115, the filaments 118 and filter cell 119 maintain the same or nearly the same shape and orientation within the support frame formed by the elongate bodies. These figures also illustrate the dynamic shape changing aspect of the device that may also be used to accommodate and conform to vessel irregularities, tortuosity, flares and tapers and while remaining in apposition to the wall. Because each elongate body may move with a high degree of independence with respect to the other, the loops or support frames formed by the elongate bodies can also independently match the shape/diameter of the lumen section in which it is placed.

Figure 3:
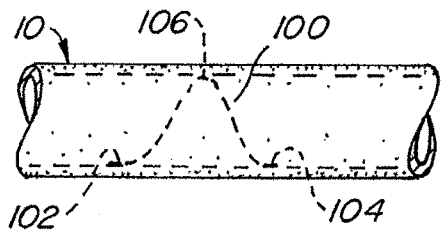
FIGS. 3-5 illustrate the interaction of a structural member with a lumen wall.
Figure 3A:
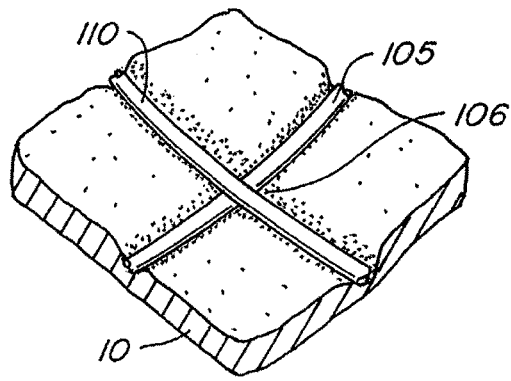
Figure 3B:
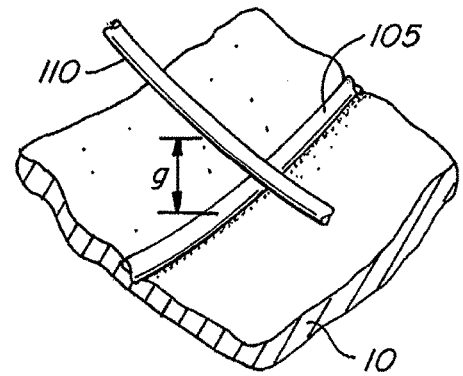

FIGS. 3, 3A and 3B illustrate the device 100 deployed into the lumen 10. As illustrated in FIG. 3, the device 100 is oriented in the lumen with the ends 102, 104 along one side of the interior vessel wall with the crossover 106 on the opposite side. FIG. 3 illustrates an embodiment of a device of the present invention that is shaped to fit within the lumen 10 without distending the lumen. In FIG. 3A the elongate bodies 105, 110 are in contact but are not joined at crossover 106. In FIG. 3B the elongate bodies 105, 110 cross one another at crossover 106 but are separated (i.e., by a gap "g").

Figure 4:
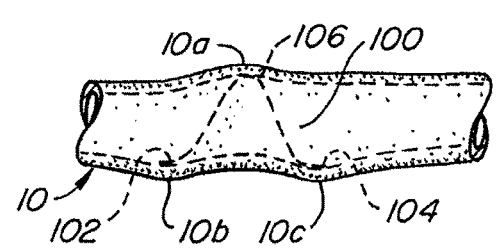
Figure 5:
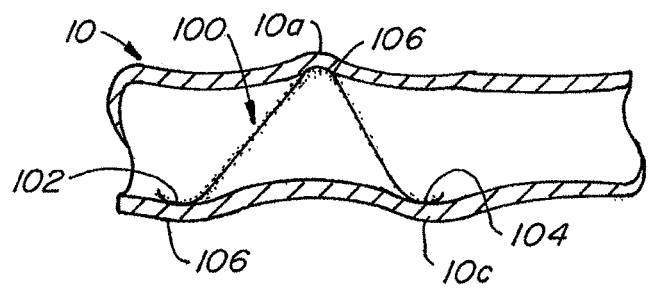

FIGS. 4 and 5 illustrate how aspects of the device design can be modified to increase the radial force applied against the interior wall of lumen 10. Devices having increased fixation force may be useful for some applications, such as vessel occlusion or for distal protection when a large amount of debris is expected. If a device is not intended to be retrieved (i.e., permanently installed into a lumen) then high radial force design devices may be used to ensure the device remains in place and distention may be used to trigger a systemic response (i.e., a tissue growth response) in the lumen to ensure device ingrowth and incorporation with the lumen interior wall.

Filter device embodiments of the present invention having low or atraumatic radial force are particularly useful in retrievable devices. As used herein, atraumatic radial force refer to radial forces produced by a filtering device embodiment that meets one or more of the following: radial forces high enough to hold the device in place with little or no migration and without damaging or overly distending the lumen interior wall; radial forces high enough to hold the device in place but while triggering little or no systemic response for the vessel wall; or forces generated by device operation that trigger reduced systemic response or a systemic response below that of a conventional filter.

In contrast to the device sized in FIG. 3 to minimize vessel distention, FIG. 4 illustrates a device 100 configured to exert greater radial force to a degree to cause lumen wall to distend. FIGS. 4 and 5 illustrate lumen wall distention by the end 102 (distention 10b), by the crossover 106 (distention 10a), and by the end 104 (distention 10c). Although not shown in these figures, the elongate bodies would likely distend the lumen along their length as well.

The radial force of a device may be increased using a number of design factors. Radial force may be increased by increasing the rigidity of the elongate body by, for example, using an elongate body with a larger diameter. Radial force may also be increased when forming the shapes of the elongate bodies (i.e., during the heat treat/set processes for Nitinol devices and the like), as well as in the material composition and configuration.

Figure 6A:
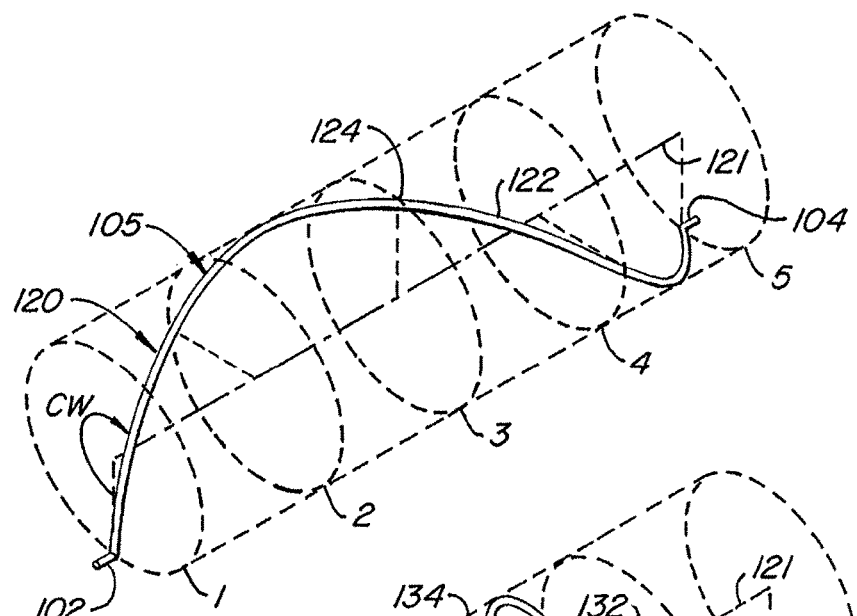
FIGS. 6A-8D illustrate various aspects of the structural members in a filtering device.
Figure 6B:
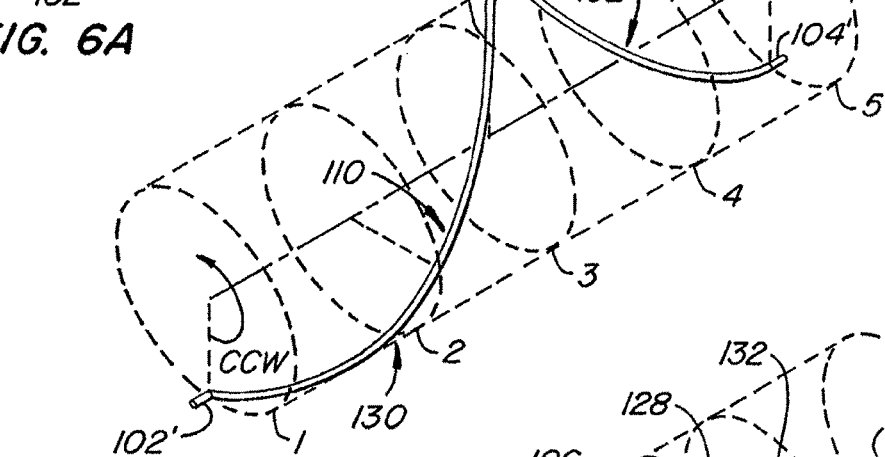
Figure 6C:
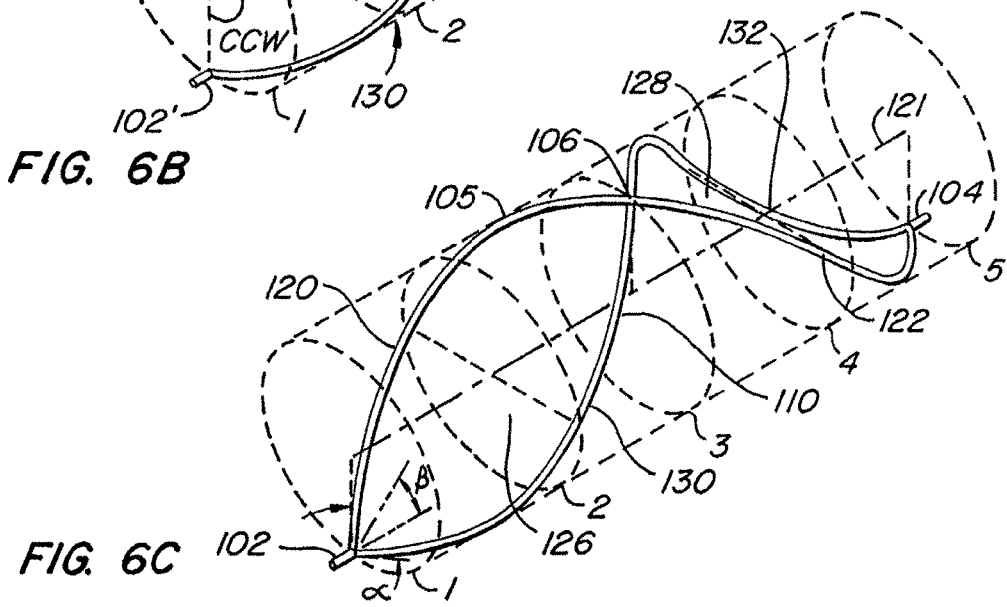

Additional details of an embodiment of the support members 105, 110 may be appreciated with reference to FIGS. 6A, 6B and 6C. FIGS. 6A, 6B illustrate the support members separately and then assembled together (FIG. 6C) about device axis 121. In general, the device axis 121 is the same as the axis along the central of a lumen into which the device is deployed. For purposes of illustration, the support members 105, 110 will be described with reference to a sectioned lumen shown in phantom having a generally cylindrical shape. The support members may also be thought of as deployed within and/or extending along the surface of an imaginary cylinder.

In the illustrative embodiments of FIGS. 6A, 6B and 6C, the support members 105, 110 are shown in an expanded, pre-defined shape. In one embodiment, the support members are formed from MRI compatible materials. The support members contain no sharp bends or angles to produce stress risers that may lead to fatigue issues, vessel erosion, and facilitate device collapse. In some embodiments, each elongate member is conventionally formed by constraining a shape memory material such as a shape memory metal alloy or shape memory polymer on a cylindrical shaping mandrel that contains pins to constrain the material into the desired shape. Thereafter, the material can be subjected to a suitable conventional heat treatment process to set the shape. One or more planes of symmetry (i.e., FIG. 15) may be provided, for example, by forming both elongate members on a single mandrel and at the same time. Other conventional processing techniques may also be used to produce symmetrical filtering device embodiments. Additionally, retrieval features described herein (if present) may be directly formed on the wire ends during support member processing. In addition, multiple devices, in a series on a long mandrel, can be made using these methods.

Examples of suitable shape memory alloy materials include, for example, copper-zinc-aluminium, copper-aluminum-nickel, and nickel-titanium (NiTi or Nitinol) alloys. Nitinol support structures have been used to construct a number of working prototypes of filter devices of the present invention as well as for use in ongoing animal studies and human implants. Shape memory polymers may also be used to form components of the filter device embodiments of the present invention. In general, one component, oligo(e-caprolactone) dimethacrylate, furnishes the crystallizable "switching" segment that determines both the temporary and permanent shape of the polymer. By varying the amount of the comonomer, n-butyl acrylate, in the polymer network, the cross-link density can be adjusted. In this way, the mechanical strength and transition temperature of the polymers can be tailored over a wide range. Additional details of shape memory polymers are described in U.S. Pat. No. 6,388,043 which is incorporated herein by reference in its entirety. In addition, shape memory polymers could be designed to degrade. Biodegradable shape memory polymers are described in U.S. Pat. No. 6,160,084 which is incorporated herein by reference in its entirety.

It is believed that biodegradable polymers may also be suited to form components of the filter device embodiments of the present invention. For example, polylactide (PLA), a biodegradable polymer, has been used in a number of medical device applications including, for example, tissue screws, tacks, and suture anchors, as well as systems for meniscus and cartilage repair. A range of synthetic biodegradable polymers are available, including, for example, polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(DTH iminocarbonate), poly(bisphenol A iminocarbonate), poly(ortho ester), polycyanoacrylate, and polyphosphazene. Additionally, a number of biodegradable polymers derived from natural sources are available such as modified polysaccharides (cellulose, chitin, dextran) or modified proteins (fibrin, casein). The most widely compounds in commercial applications include PGA and PLA, followed by PLGA, poly(e-caprolactone), polydioxanone, trimethylene carbonate, and polyanhydride.

While described as forming the support structures, it is to be appreciated that other portions of the filter device may also be formed from shape memory alloys, shape memory polymers or biodegradable polymers. Other filter device components that may also be formed from shape memory alloys, shape memory polymers or biodegradable polymers include, for example, all or a portion of a retrieval feature, a material capture structure or an attachment between a material capture structure and a support structure. Additionally or alternatively, the devices described herein may have all or a portion of their components formed from medical grade stainless steel.

FIG. 6A illustrates the first support member 105 extending from an end 102 to an end 104 along in a clockwise manner about the lumen interior wall (sectioned phantom lines) and the device axis 121. The support member 105 extends from the end 102 in section 1 at the 6 o'clock position, up to the 9 o'clock position in section 2, the 12 o'clock position in section 3, the 3 o'clock position in section 4 to the end 104 at the 6 o'clock position in section 5. The support member 105 has two sections 120, 122 on either side of an inflection point 124. The inflection point 124 is positioned at about the 12 o'clock position in section 3. The radius of curvature of the sections 120, 122 may be the same or different. The cross section shape of the support member 105 is generally circular but may have one or more different cross section shapes in alternative embodiments.

FIG. 6B illustrates the second support member 105 extending from an end 102' to an end 104' along in a counter-clockwise manner about the lumen interior wall (sectioned phantom lines) and the device axis 121. The support member 110 extends from the end 102' in section 1 at the 6 o'clock position, up to the 3 o'clock position in section 2, the 12 o'clock position in section 3, 9 o'clock position in section 4 to the end 104' at the 6 o'clock position in section 5. The support member 110 has two sections 130, 132 on either side of an inflection point 134. The inflection point 134 is positioned at about the 12 o'clock position in section 3. The radius of curvature of the sections 120, 122 may be the same or different. The cross section shape of the support member 105 is generally circular but may have one or more different cross section shapes in alternative embodiments.

Figure 7A:
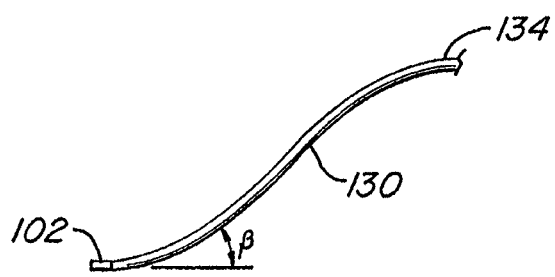
Figure 7B:
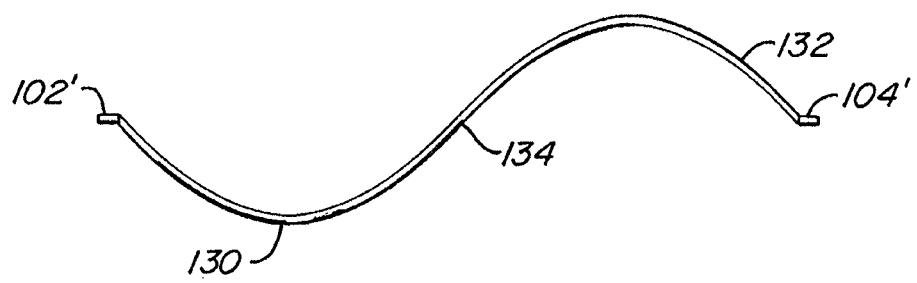
Figure 7C:
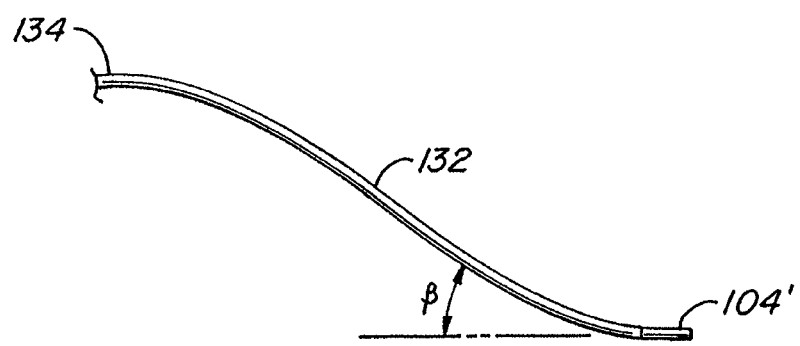

FIG. 6C illustrates the crossover 106 and first and second support members 105, 110 joined together at the ends. The first sections 120, 130 form a rounded frame 126. The angle β is formed by a portion of the lumen wall contacting end 102 and a plane containing the frame 126 and is referred to as the take off angle for the elongate members at end 102. In one alternative, the angle β is formed by a portion of the lumen wall contacting end 102 and a plane containing all or a portion of one or both sections 120, 130. In yet another alternative, the angle β is formed by a portion of the lumen wall contacting end 102 and a plane containing all or a portion of end 102 and all or a portion of the crossover 106. Another angle β is formed on end 104 as discussed above but in the context of end 104, a portion of the lumen wall contacting end 104, sections 122, 132 and the rounded frame 128 as illustrated in FIGS. 7A-7C. An angle formed by the support frames 126, 128 ranges generally between 20 degrees to 160 degrees in some embodiments and generally between 45 degrees to 120 degrees in some other embodiments.

FIG. 7A is a side view of section 130 in FIG. 6B, FIG. 7B is a top down view of FIG. 6B and FIG. 7C is side view of section 132 in FIG. 6B. The angle β ranges generally between 20 degrees to 160 degrees in some embodiments and generally between 45 degrees to 120 degrees in some other embodiments. The angle α is formed by a portion of section 120, a portion of section 130 and the end 102. Alternatively, the angle α is formed by the end 102 and tangents formed with a portion of the sections 120, 130. Another angle α is formed on end 104 as discussed above but in the context of end 104, a portion of the lumen wall contacting end 104 and sections 122, 132. The angle α ranges generally between 40 degrees to 170 degrees in some embodiments and generally between 70 degrees to 140 degrees in some other embodiments.

Figure 7D:
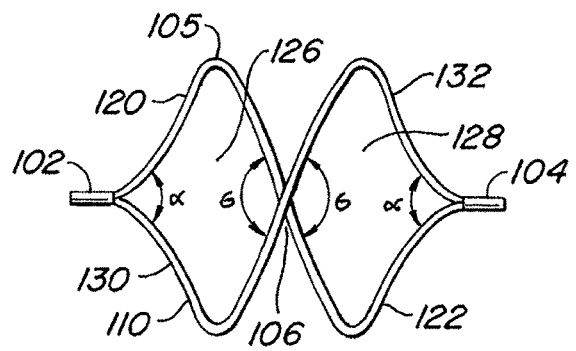
Figure 7E:
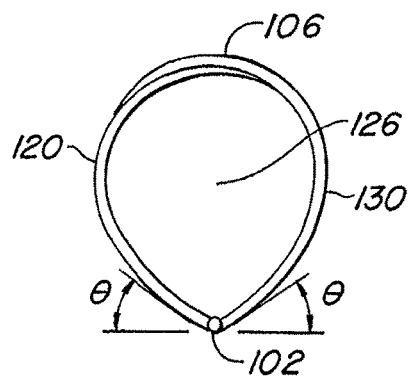

FIG. 7D illustrates a top down view of FIG. 6C. The angle σ is defined as the angle between a portion of section 120 between the inflection point 124 and the end 102 on one side and a portion of section 130 between the inflection point 134 and the end 102' on the other side. The angle σ is also defined as the angle between a portion of section 122 between the inflection point 124 and the end 104 on one side and a portion of section 132 between the inflection point 134 and the end 104' on the other side. The angle σ defined by sections 120, 130 may be the same, larger, or smaller than the angle σ formed by the sections 122, 132. The angle CT ranges generally between 10 degrees to 180 degrees in some embodiments and generally between 45 degrees to 160 degrees in some other embodiments.

FIG. 7D illustrates an end view of FIG. 6C taken from end 102. The angle θ is defined as the angle between a plane tangent to a portion of section 120 and a plane containing the end 102 that is also generally parallel to the device axis 121. An angle θ may also be defined as the angle between a plane tangent to a portion of section 130 and a plane containing the end 102 that is also generally parallel to the device axis 121. The angle θ defined by section 120 may be the same, larger, or smaller than the angle θ formed by the section 130. Similarly, an angle θ may be defined as discussed above and using as the angle between a plane tangent to a portion of section 122 or 132 and a plane containing the end 102 that is also generally parallel to the device axis 121. The angle θ ranges generally between 5 degrees to 70 degrees in some embodiments and generally between 20 degrees to 55 degrees in some other embodiments.

Figure 7F:
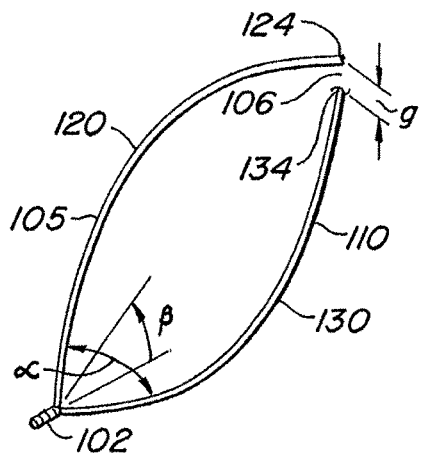
Figure 7G:
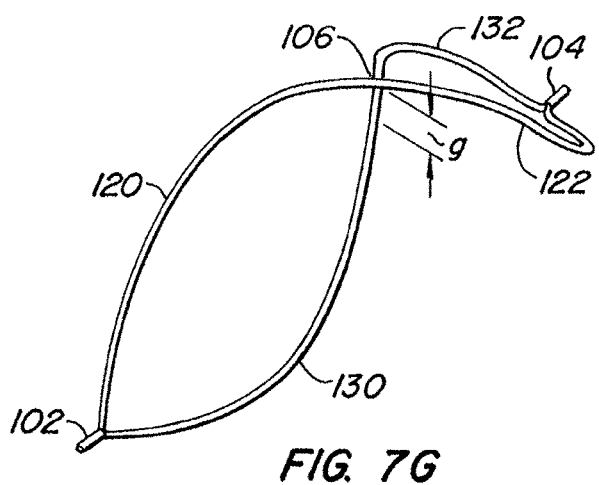

FIGS. 7F and 7G are perspective views of an alternative embodiment of the device illustrated in FIG. 6C. In the embodiment illustrated in FIGS. 7F and 7G, the support member 110 crosses underneath and does not contact the support member 105 at the crossover 106. The gap "g" between the support members is also illustrated in the FIG. 7G.

Figure 8A:
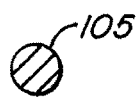
Figure 8B:
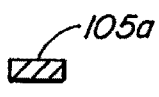
Figure 8C:
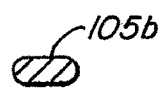
Figure 8D:
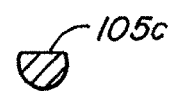

FIG. 8A illustrates the elongate body 105 with a generally circular cross section. However, many other cross section shapes are possible and may be used such as, for example, rectangular elongate body 105a (FIG. 8B), rectangular elongate body with rounded edges (not shown), oval elongate body 105b (FIG. 8C) and circular elongate body with a flattened edge 105c (FIG. 8D). In some embodiments, an elongate body will have the same cross section along its length. In other embodiments, an elongate body will have different cross sections along its length. In another embodiment, an elongate body has a number of segments and each segment has a cross section shape. The segment cross section shapes may be the same or different. The cross section shape of the elongate member is a factor used to obtain the desired radial force along the elongate member. The material used to form the elongate body (i.e., a biocompatible metal alloy such as Nitinol) may be drawn to have a desired cross section shape, or drawn in one cross section shape and then treated using conventional techniques such as grinding, laser cutting and the like to obtain the cross section shape were desired.

FIGS. 9A, 9B illustrate an embodiment of a material capture structure 115 extended across a generally planar, rounded frame 126 formed by the support members. FIG. 9A is a slight perspective view of a side view of the device. In this embodiment, sections 120, 130 of the support members lie mostly within in a single plane (i.e., in a side view of FIG. 9A section 110 is visible and blocks view of section 120) that also holds the rounded frame 126. FIG. 9B is a perspective view showing the material capture structure 115 extended between and attached to rounded frame 126. In this embodiment, the capture structure 115 extends across and is attached to the first sections 120, 130. In this embodiment, the material capture structure is a plurality of generally rectangular filter cells 119 formed by intersecting filaments 118. Other types of filter structures are described in greater detail below and may also be supported by the support frames formed by the structural members. In some embodiments such as FIGS. 9A and 9B, the angle β may also define the angle between the device axis and a plane containing a material capture structure.

The support frame 126 and the material capture structure 115 is not limited to planar configurations. Non-planar and compound configurations, for example, are also possible as illustrated in FIGS. 10A and 10B. FIG. 10A is a side view of a non-planar structural support 110' having another inflection point 134' between the inflection point 134 and the end 102. The structural support 110' has more than one different radius of curvature between the end 102 and the crossover 106. In some embodiments, there could be more than one radius of curvature between the end 102 and the inflection point 134' as well as be more than one radius of curvature between the inflection point 134' and the inflection point 134. As a result, section 130' is a section possibly having different shapes, a number of different curvatures and at least one inflection point. As seen in FIG. 10B, the support structure 105' is also non-planar with more than one different radius of curvature between the end 102 and the inflection point 124. In some embodiments, there could be more than one radius of curvature between the end 102 and the inflection point 124' as well as be more than one radius of curvature between the inflection point 124' and the inflection point 124. As a result, section 120' is a section having different shapes, a number of different curvatures and one or more inflection points. Similar non-planar configurations may be used on end 104. The material capture structure 115' is adapted to conform to the shape of non-planar frame 126' to produce a non-planar filter support structure.

Figures 11, 12A:
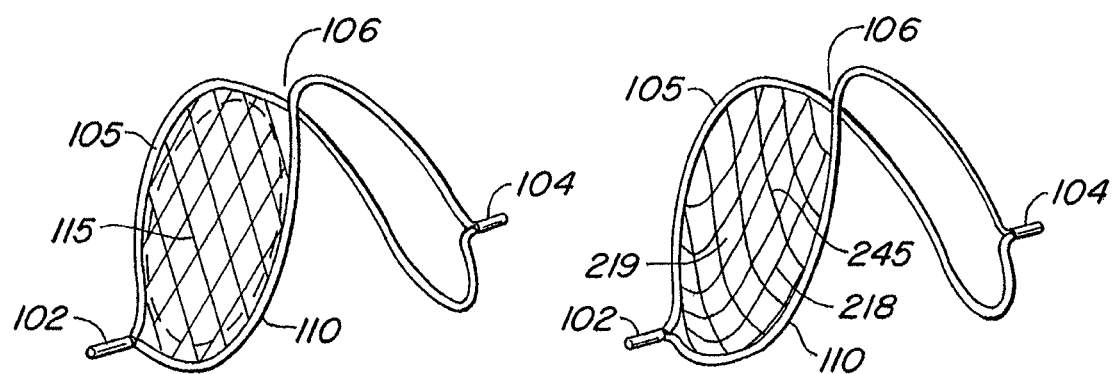
Figure 12B:
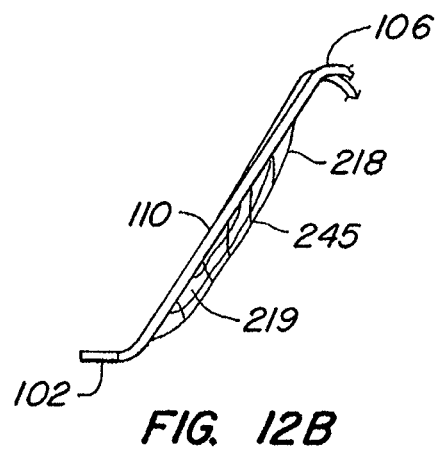

FIG. 11 illustrates a material capture structure 115 that remains in a generally planar arrangement between opposing portions of the support members 105, 110. In addition to FIG. 10B above, other alternative non-planar capture structures are possible even if the support frame is generally planar. FIG. 12A is a perspective view of a non-planar capture structure 245 within a generally planar support frame formed by support members 105, 110. Capture structure 245 is formed by intersecting strands, fibers, filaments or other suitable elongate material 218 to form filter cells 219. The capture structure 245 is slightly larger than the support frame dimensions resulting in a filter structure that is deformed out of the plane formed by the support structure as illustrated in FIG. 12B.

The material capture structure 115 may be in any of a number of different positions and orientations. FIG. 13A illustrates an embodiment of a filter of the present invention having two open loop support frames formed by support members 105, 110. Flow within the lumen 10 is indicated by the arrow. In this embodiment, the material capture structure 115 is placed in the upstream open loop support structure. In contrast, the material capture structure may be positioned in the downstream open loop support structure (FIG. 13B). In another alternative configuration, both the upstream and the downstream support frames contain material capture structures 115. FIG. 13C also illustrates an embodiment where a material capture structure is placed in every support loop in the device.

There are filter device embodiments having equal numbers of support frames with capture structures as support frames without capture structures (e.g., FIGS. 13A and 13B). There are other embodiments having more support frames without capture structures than there are support frames with capture structures. FIG. 14 illustrates a filter embodiment 190 having more support frames without capture structures than support frames with captures structures. The filter device 190 has two support members 105, 110 that are positioned adjacent to one another to form a plurality of support frames that are presented to the flow within the lumen 10. Alternatively, the plurality of support frames positioned to support a material capture structure across the flow axis of the device 190 or the lumen 10. The support members are joined together at end 192 and have two inflection points before being joined at end 194. The support members 105, 110 cross over one another at crossovers 106 and 196. The support frame 191 is between end 192 and crossover 106. The support frame 193 is between the crossovers 106, 196. The support frame 195 is between the cross over 196 and the end 194.

In addition, the filter device 190 has a retrieval feature 140 on each end. The retrieval feature 140 has a curved section 141 ending with an atraumatic tip or ball 142. The retrieval feature 140 rises up above the lumen wall placing the ball 142 and all or a portion of the curved section 141 into the lumen flow path to simplify the process of snaring the device 190 for retrieval or repositioning. Having a retrieval feature on each end of the device allows the device 190 to be recovered from the upstream or downstream approach to the device in the lumen 10. Various aspects of retrieval feature embodiments of the present invention are described in greater detail below.

Figure 14A:
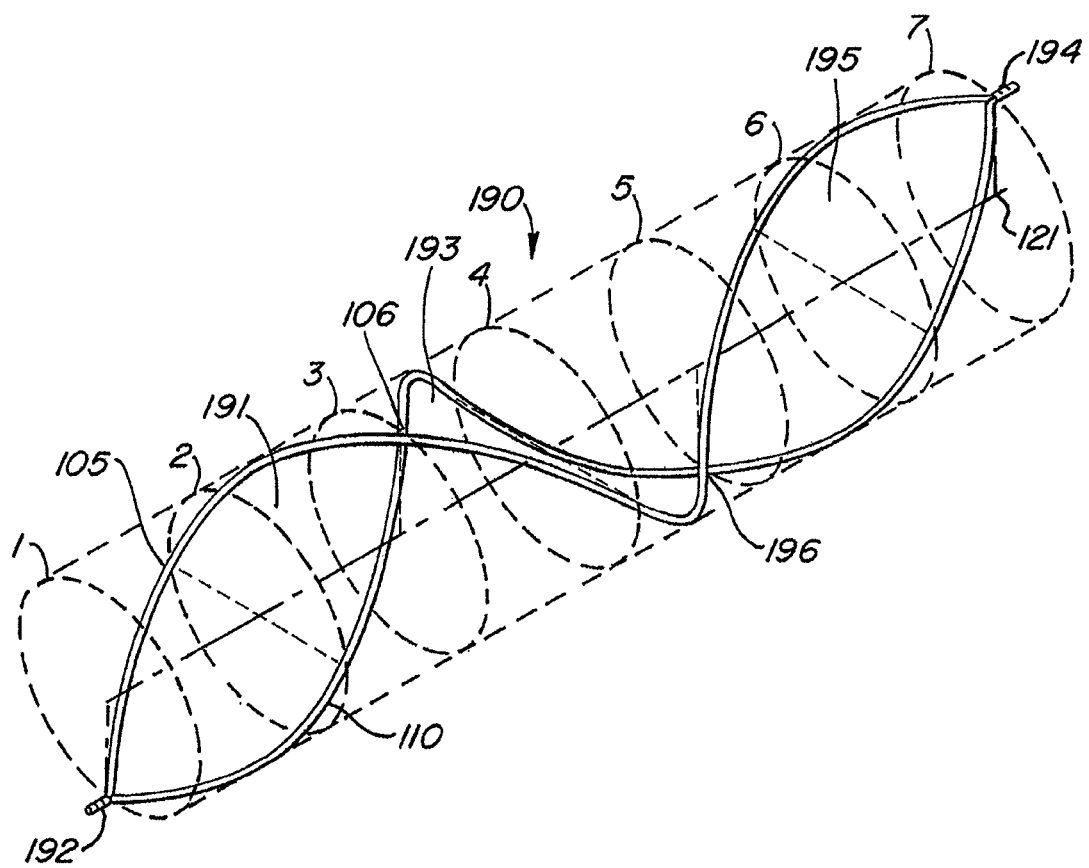
FIGS. 14-14C illustrate various aspects of a filtering device having three support frames.
Figure 14B:
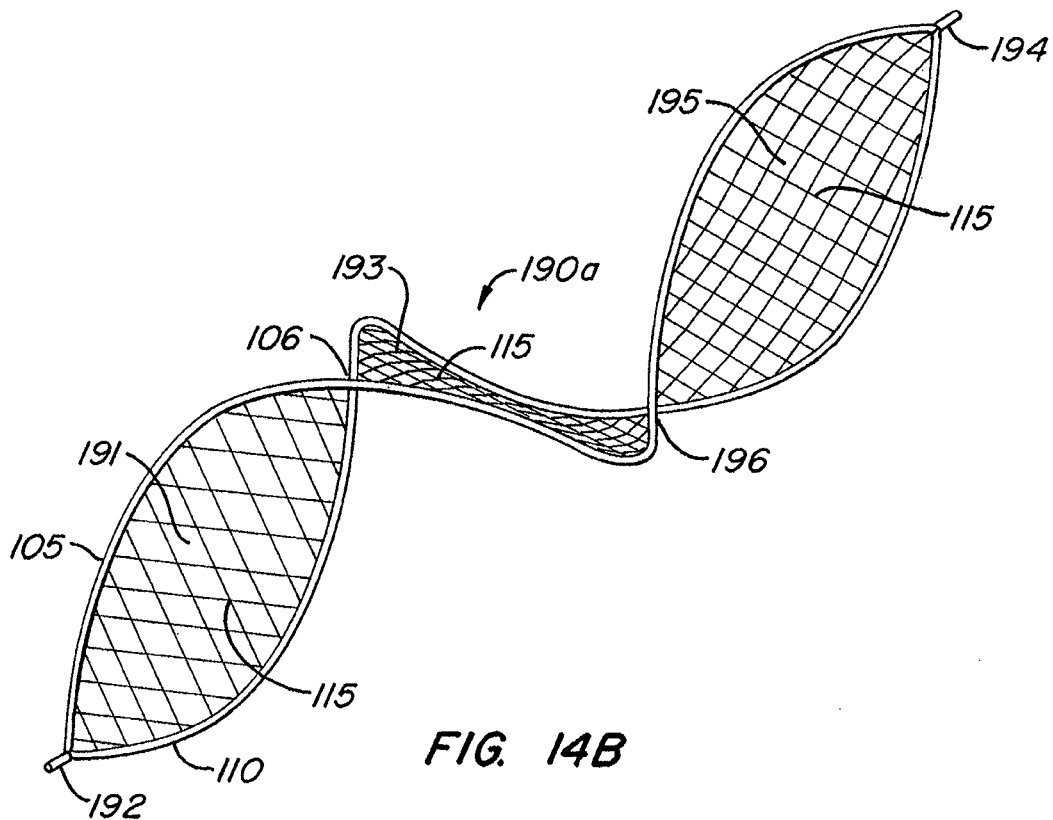

FIG. 14A illustrates the filter 190 imposed on a phantom cylinder having 7 sections. The retrieval features 140 have been omitted for clarity. The first support member 105 extends clock wise from end 192 about and along the axis of the device 121. The first support member 105 crosses section 2 at the 9 o'clock position, section 3 and the crossover 106 at the 12 o'clock position, section 4 at the 3 o'clock position, section 5 and the crossover 196 at the 6 o'clock position, section 6 at the 9 o'clock position and section 7 and the end 194 at the 12 o'clock position. The second support member 110 crosses section 2 at the 3 o'clock position, section 3 and the crossover 106 at the 12 o'clock position, section 4 at the 9 o'clock position, section 5 and the crossover 196 at the 6 o'clock position, section 6 at the 3 o'clock position and section 7 and the end 194 at the 12 o'clock position. FIG. 14B illustrates an alternative device embodiment 190*a* that is similar to the device 190 except that all support frames formed by the elongate members is used to support a material capture structure. In the illustrated embodiment, frames 191, 193 and 195 each support at material capture structure 115.

Figure 14C:
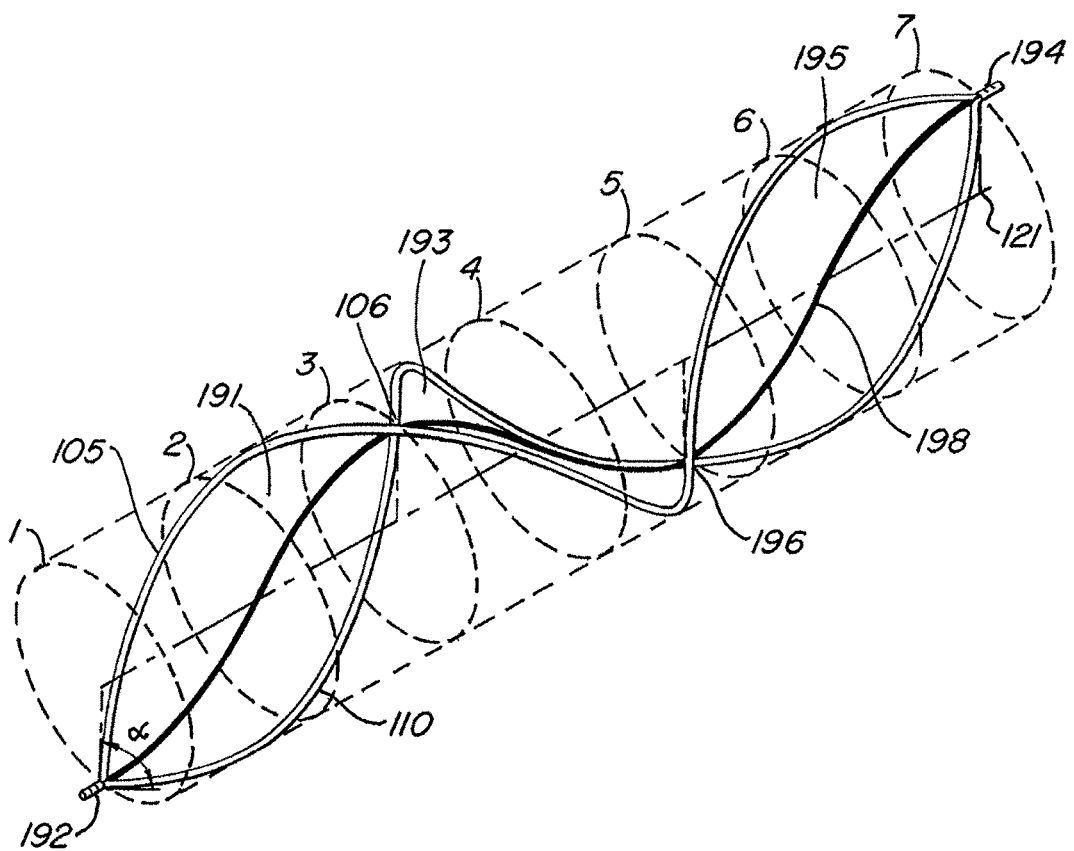

FIG. 14C illustrates an alternative configuration of filter 190. The filter device 190*b* is similar to device 190 and 190*a* and includes an additional support member 198 extending along the support member 105. In one embodiment, the additional support member 198 extends along the device axis 121, is positioned between the first and the second support members 105, 110 and is attached to the first end 192 and the second end 194. In the illustrative embodiment, the third support member 198 begins at end 192 and the 6 o'clock position in section 1, crosses section 3 and the crossover 106 at the 12 o'clock position, crosses section 5 and the crossover 196 at the 6 o'clock position, and ends at the 12 o'clock position in section 7 at the end 194.

Figure 15:
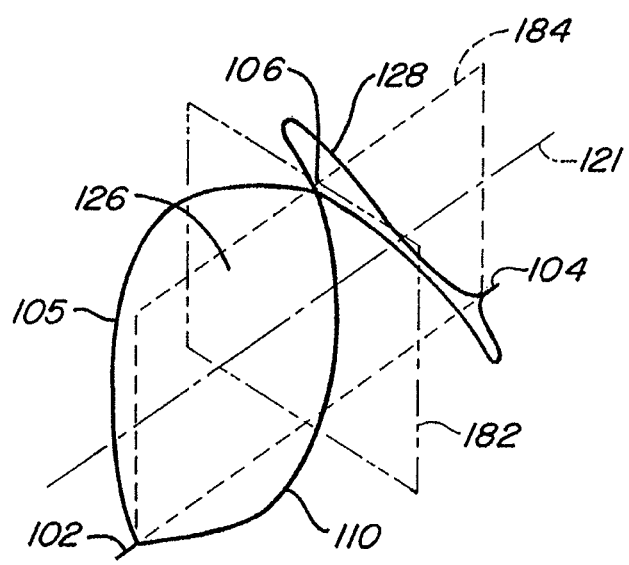
FIG. 15 illustrates planes of symmetry for filtering devices.

FIG. 15 illustrates the planes of symmetry found in some filter device embodiments of the present invention. The filtering structure that would be supported by one or both of the support frames is omitted for clarity. In one aspect, FIG. 15 illustrates an embodiment of an endoluminal filter of the present invention having a support structure that is generally symmetrical about a plane 182 that is orthogonal to the flow direction of the filter or filter axis 121 and contains a crossover point 106 between two structural elements of the support structure 105, 110. In another aspect, FIG. 15 illustrates an embodiment of an endoluminal filter of the present invention having a support structure that is generally symmetrical about a plane 184 that is parallel to the flow direction of the filter (i.e., axis 121) and contains both ends of the support structure 102, 104. It is to be appreciated that some filter device embodiments of the present invention may have either or both of the above described symmetrical attributes. It is to be appreciated that the above described symmetrical attributes are also applicable to the construction of embodiments of the material capture structures alone or as installed in a filter.

Figure 16A:
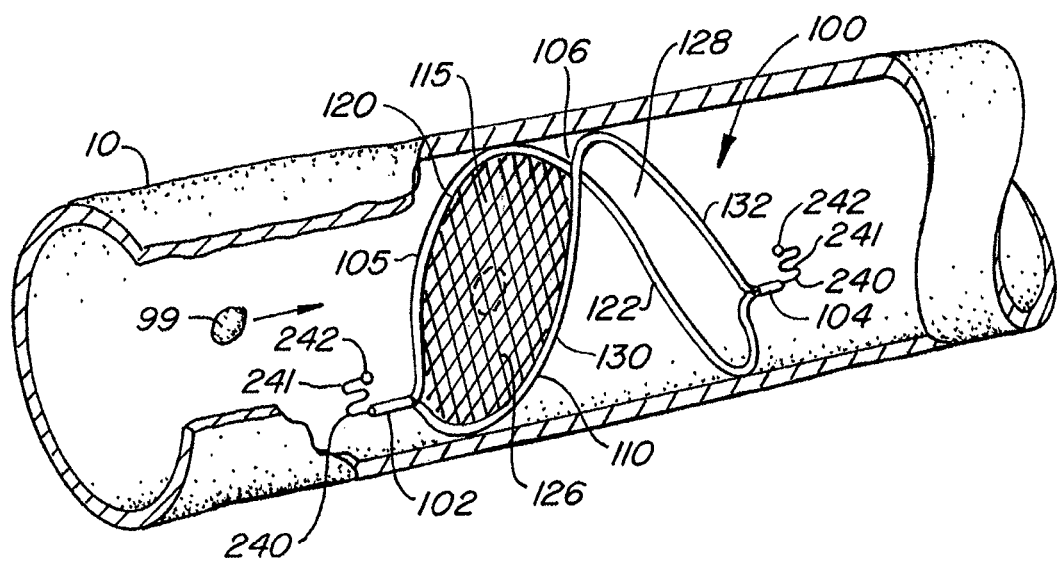
FIGS. 16A and 16B illustrate the response of a filtering device when contacted by debris flowing in a lumen.
Figure 16B:
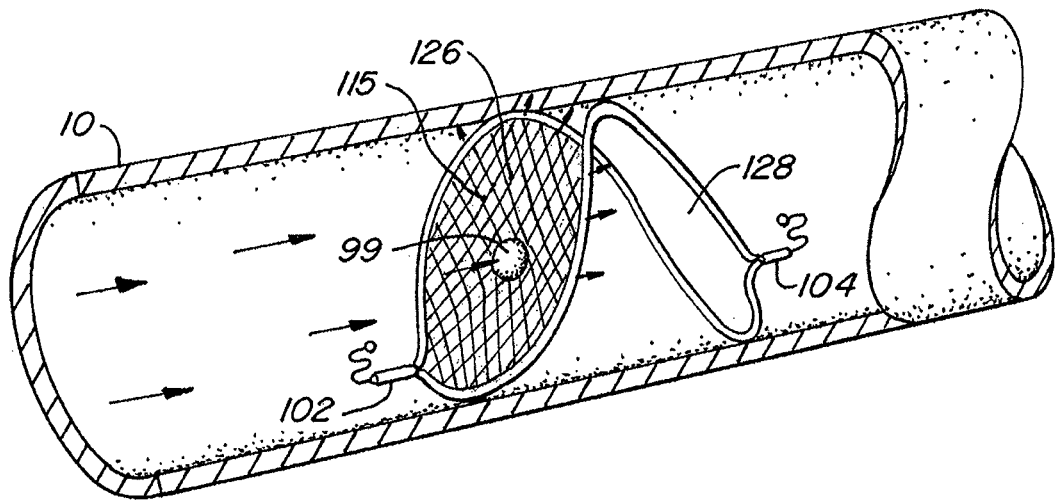

FIGS. 16A and 16B illustrate the response of a filter device 200 in response to a piece of clot material 99 contacting the material capture structure 115. The direction of flow and movement of the clot material 99 within lumen 10 is indicated by the arrows. The filter device 200 is similar to the embodiments described above with regard to FIGS. 6A-7G with the addition of the retrieval features 240 added to the ends 102, 104. The retrieval feature 240 has a curved section with multiple curves 141 that terminate with an atraumatic end 242. The multiple curves 141 are advantageously configured to collapse about a retrieval device (i.e., a snare in FIGS. 71A, 71B) to facilitate device 100 capture during retrieval. In this illustrative embodiment the multiple curves are generally shaped like a sinusoid and the end 242 is shaped like a ball or a rounded tip.

It is believed that upon embolic entrapment, the force fluid flow acting on clot material 99 is transmitted from the capture structure 115 to support frame 126 securing the capture structure 115. The force acting on the support frame 126 and in turn the support members 105, 110 urges the end 104 into the lumen wall. This action effectively fixes the second support frame 128. The force acting on the support frame 126 causes the angle β associated with the support frame 126 to increase the support frame 126 wedges further into the lumen wall.

Figure 17:
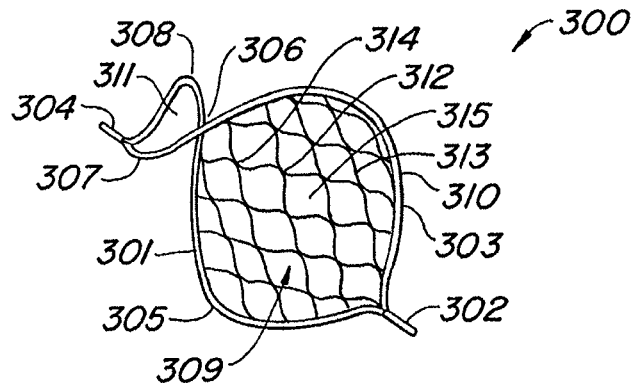
FIGS. 17-19 illustrate alternative filtering device aspects having different sized support frames and structural member lengths.
Figure 18:
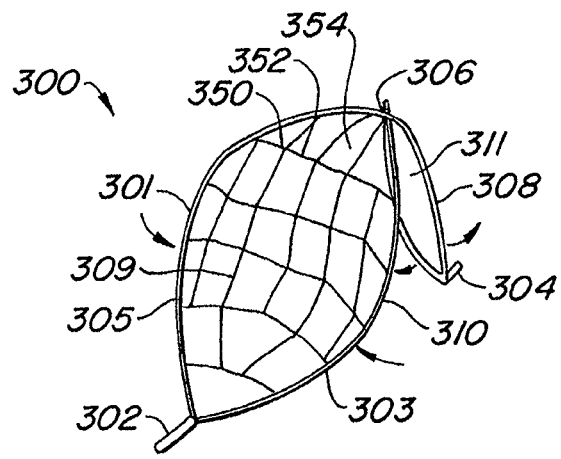
Figure 19:
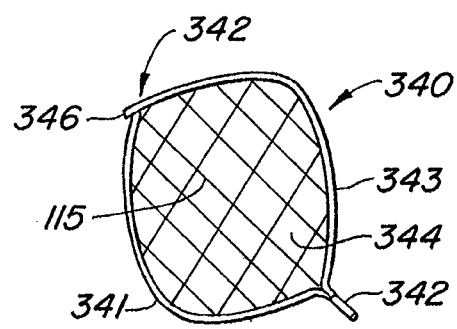

FIGS. 17, 18, and 19 illustrate various alternative filter device embodiments with support structures of different size and that may not be in contact with the lumen wall. FIG. 17 illustrates a perspective view of a filter device 300 according to one embodiment of the present invention. In this embodiment, elongate members 305, 310 are joined at ends 302, 304, to form frame 309 from end 302, sections 301, 303 and crossover 306 and frame 311 from end 304, sections 307, 308 and cross over 306. The frame 309 supports another embodiment of a material capture according to the present invention. The illustrated material capture structure 312 includes a plurality of strands 313 joined 314 to form a plurality of filter cells 315. The strands 313 may be joined using processes described below (e.g., FIG. 53A-53D) or may be formed by extruding the desired shape and size filter cell 315 from a material (e.g., FIG. 56).

FIG. 17 illustrates a so-called capacitor design because the elongate members that form frame 311 are configured to expand and contract the size and shape of frame 311 in response to changes in frame 309. This design feature allows an embodiment of the present invention to accommodate a large range of sizing and diameter changes. FIG. 18 illustrates an embodiment of the filter device 300 having a capture structure 350 having filter cells 354 formed by intersecting strands 352. FIG. 18 illustrates how inward movement of the frame 309 (indicated by the arrows) is corresponds to outward movement (indicated by the arrows) in the frame 308.

FIG. 19 illustrates an alternative filter device embodiment where the second frame is not closed. The filter device 340 includes support members 341, 343 that form a rounded support frame 344 to support the material capture device 115. The support members 341, 343 extend some distance beyond the cross over 342 but are not joined to form another end. A portion 346 of the support member 343 is shown extending beyond the cross over 342. The support members 341, 343 may extend for some distance along the device axis after the cross over 342 and may follow the same or a different shape as the shape of the support members in frame 309. The support members may extend along the device axis similar to earlier described two loop embodiments but stop short of being joined at a second end (e.g., FIG. 87).

Figure 20:
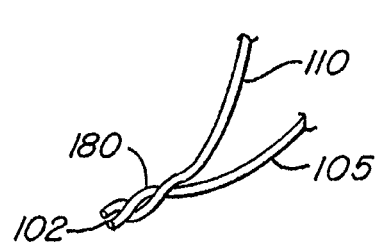
FIGS. 20-24 illustrate various alternative filtering device ends and structural member joining techniques.
Figure 21:
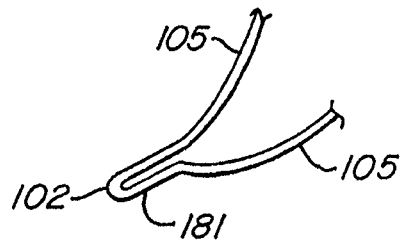
Figure 22:
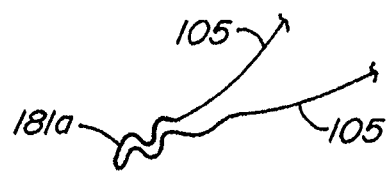
Figure 23:
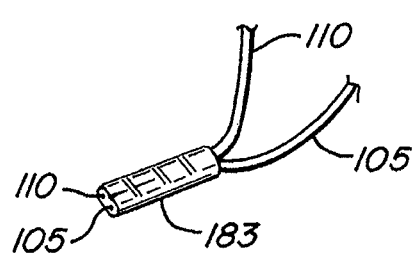
Figure 24:
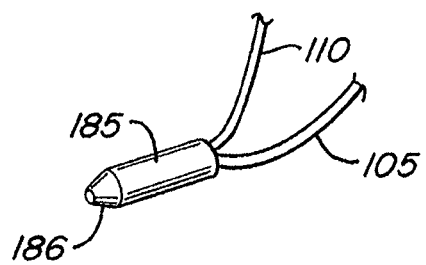

The ends of the filter devices of the present invention may be formed in a number of ways. A portion of the support structures 105, 110 may be wound 180 around one another (FIG. 20). In the illustrated embodiment, the wound portion 180 is used to form the end 102. In another alternative, the filtering device is formed from a single support member 105 that loops back on itself. In the illustrative embodiment of FIG. 21, support member 105 is formed into loop 181 to form the end 102. In an alternative to loop 181, the loop may contain a plurality of undulations (i.e., loop 181a in FIG. 22) or be formed into the shape of a retrieval feature or other component of the filter device. In yet another alternative, a cover is used to clamp, to join or otherwise bond the structural members together. In the illustrative example of FIG. 23, a generally cylindrical cover 183 is used to join together members 105, 110. The cover 183 may use any conventional joining method to secure the support members together such as adhesive, welding, crimping and the like. An alternative tapered cover 185 is illustrated in the embodiment of FIG. 24. The tapered cover 185 has a cylindrical shape and a tapered end 186. The tapered end 186 around the end having the tapered cover 185 and facilitates deployment and retrieval of the device. In one embodiment, the cover 185 is made of the same material as the structural member and/or the retrieval feature.

Some filter device embodiments of the present invention may include one or more retrieval features to assist recapturing and partially or fully recovering a deployed filter device. Retrieval features may be placed in any of a number of positions on the device depending upon the specific filter device design. In one embodiment, the retrieval device is positioned not only for ease of device recovery but also attached to the device in such a way that pulling on the retrieval device actually facilities removal of the device. In one embodiment, pulling on the retrieval device pulls the structural members away from the lumen wall. These and other aspects of the cooperative operation of the retrieval features during deployment and recapture will be described below with regard to FIGS. 72A-73D.

Figure 25:
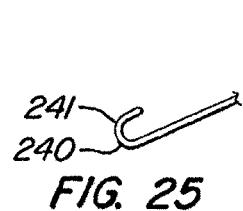
FIGS. 25-27C illustrate various alternative retrieval features.
Figure 26:
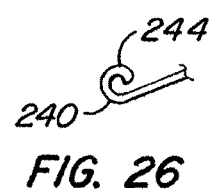
Figure 27A:
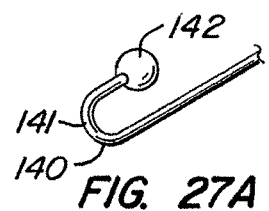
Figure 27B:
Figure 27C:
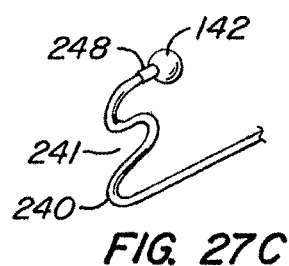

Several alternative embodiments of retrieval devices of the present invention are illustrated in FIGS. 25-27C. FIG. 25 illustrates a retrieval device 240 with a simple curve 241 formed in the end. FIG. 26 illustrates a retrieval device 240 with a curve 244 that is has a sharper radius of curvature than the curve 241 in FIG. 25. FIG. 27A illustrates a retrieval feature 140 having a curved section 141 with an atraumatic end 142. In the illustrative embodiment, the atraumatic end 142 is a ball than may be added to the end of curve 141 or formed on the end of the member used to form the feature 140. A ball 142 may be formed by exposing the end of the curved section 141 to a laser to melt the end into a ball. FIG. 27B illustrates a retrieval feature with a plurality of curved sections 241. In one embodiment, the curved sections 241 have a generally sinusoidal shape. In another embodiment, the curved sections 241 are configured to collapse when pulled on by a retrieval device like a snare (i.e., FIGS. 71A, 71B) FIG. 27C illustrates a retrieval feature 240 having a plurality of curved sections 241 and a ball 142 formed on the end. In additional embodiments, retrieval features of the present invention may include markers or other features to help increase the visibility or image quality of the filter device using medical imaging. In the illustrative embodiment of FIG. 27C, a radio opaque marker 248 is placed on the curved section 241. The marker 248 may be made from any suitable material such as platinum, tantalum or gold.

Figure 28A:
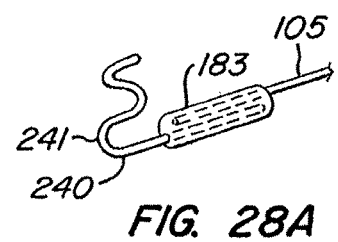
FIGS. 28A-28C illustrate various techniques of joining or forming retrieval features.
Figure 28B:
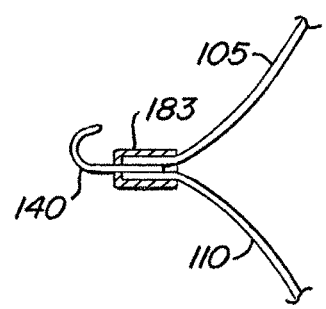
Figure 28C:
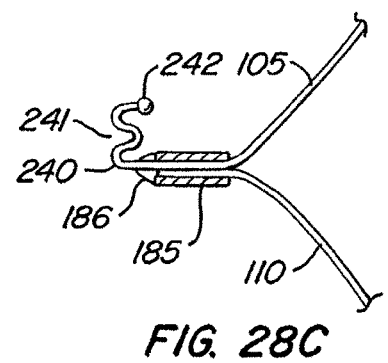

A cover placed about the ends may also be used to join a retrieval feature to an end or two support members. A cover 183 may be used to join a retrieval feature 240 to a support member 105 (FIG. 28A). In this illustrative embodiment, the support structure 105 and the retrieval feature 240 are separate pieces. A cover 183 may also be used to join together two members 110, 105 to a retrieval feature 140 (FIG. 28B). In another alternative embodiment, the retrieval feature is formed from a support member that is joined to the other support member. In the illustrative embodiment of FIG. 28C, the support member 105 extends through the tapered cover 185 and is used to form a retrieval feature 240. The tapered cover 185 is used to join the first support member and second support member 105, 110. In one alternative of the embodiment illustrated in FIG. 28C, the diameter of the support member 105 is greater than the diameter of the retrieval feature 240. In another embodiment, the diameter of the retrieval feature 240 is less than diameter of the support member 105 and is formed by processing the end of the support member down to a smaller diameter and is then shaped to form the retrieval feature 240. In another embodiment, the ball 242 or other atraumatic end is formed on the end of the retrieval feature.

Figure 29:
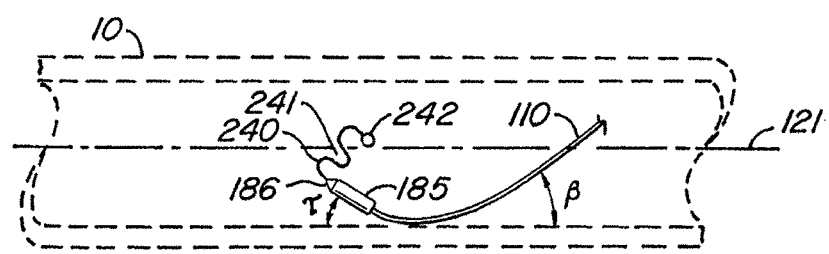
FIG. 29 illustrates a filtering device with a retrieval feature positioned within a lumen.

FIG. 29 illustrates a partial side view of a filter device in a lumen 10. This figure illustrates the retrieval feature angle τ formed by the retrieval feature and the interior lumen wall. The retrieval feature angle τ is useful in adjusting the height and orientation of the retrieval curves 214 and ball 242 within the lumen to improve the retrievably of the device. Generally, retrievably improves as the retrieval feature moves closer to the device axis 121 (i.e., central to the lumen axis as well). Additional curves may be added to the support members 110, 105 as needed to provide the desired range of retrieval feature angles. In one embodiment, τ ranges from −20 degrees to 90 degrees. In another embodiment, τ ranges from 0 degrees to 30 degrees.

Attachment of Material Capture and Other Filtering Structures to Support Structures A number of different techniques may be used to attach material capture structures to support members. For clarity, the material capture structure has been omitted from the illustrations that follow but would be suitably secured using the line 351 or a loop. In FIG. 30 illustrates a line 351 with a number of turns 353 about a support member 105. The line 351 is secured back onto itself using a clip 351a. FIG. 31 illustrates a line 351 with a number of turns 353 about the support member 105 to secure a loop 353a that may be used to tie off or otherwise secure a material capture structure. A line 351 may also be glued 355 to a support 105 (FIG. 32). In another alternative embodiment, holes 356 formed in the support member are used to secure one or more lines 351 that are used in turn to secure a material capture structure. In an alternative to the linear arrangement of holes 356, FIG. 36 illustrates how holes 356 may be provided in a number of different orientations to assist in securing a material capture to the support structure 105. Alternatively, the line 351 may be glued 355 into the hole 356 (FIG. 34A and in section view 34B).

In other alternative embodiments, the holes 356 are used to secure lines 351 as well as provide a cavity for another material to be incorporated into the support structure 105. Other materials that may be incorporated into the support structure 105 include, for example, a pharmacological agent or a radio opaque material. The use of a radio opaque marker may be useful, for example, when the support structure is formed from a material with low imaging visibility such as, for example, shape memory polymers or biodegradable polymers. FIG. 34C illustrates an embodiment where one hole 356 is used to secure a line 351 and the other is filled with material or compound 357. In another alternative, some or all of the holes 356 may be filled with another material as in FIG. 35. In yet another alternative, the holes 356 are filled with small barbs 358 that may be used to secure the device to the lumen wall. The illustrative embodiment of FIG. 37 the barbs 358 are only long enough to break the surface of the lumen interior wall and not pierce through the lumen wall. While each of the above has been described with regard to the support member 105, it is to be appreciated that these same techniques could be applied to the support member 110 or other structure used to support a material capture structure. Additional alternative embodiments of hooks, barbs or other fixation devices or elements are described below with regard to FIGS. 88-126D.

Figure 38A:
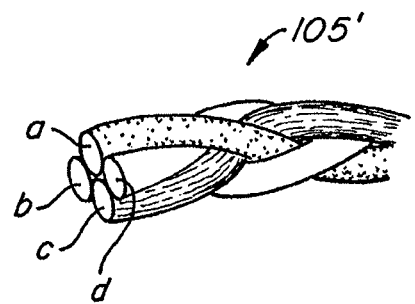
Figure 38B:
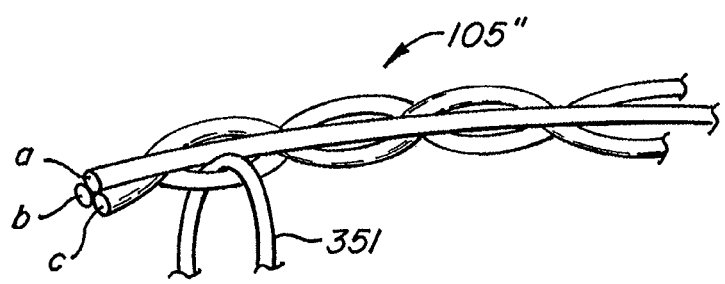

It is to be appreciated that the support structure embodiments are not limited to single member constructions. FIG. 38A illustrates an alternative braided support member 105'. Braided support structure 105' is formed by 4 strands a, b, c, and d. FIG. 38B illustrates another alternative braided support member 105". Braided support structure 105" is formed by 3 strands a, b, and c. FIG. 38B also illustrates how the braid structure may be used to secure a line 351. As can be seen in this embodiment, by using the line 351a material capture structure (not shown) is secured to at least one strand within the braided structure 105".

Figure 39:
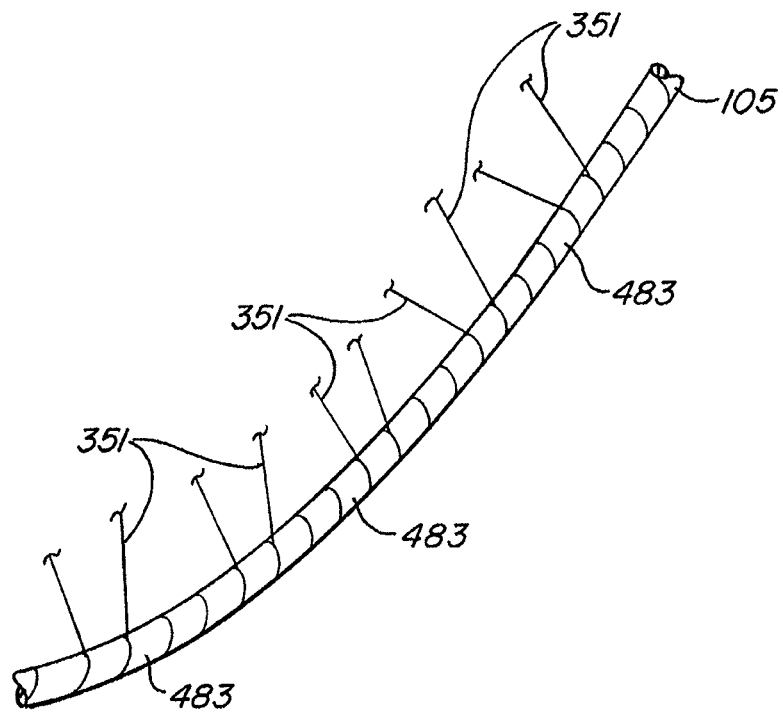
Figure 40:
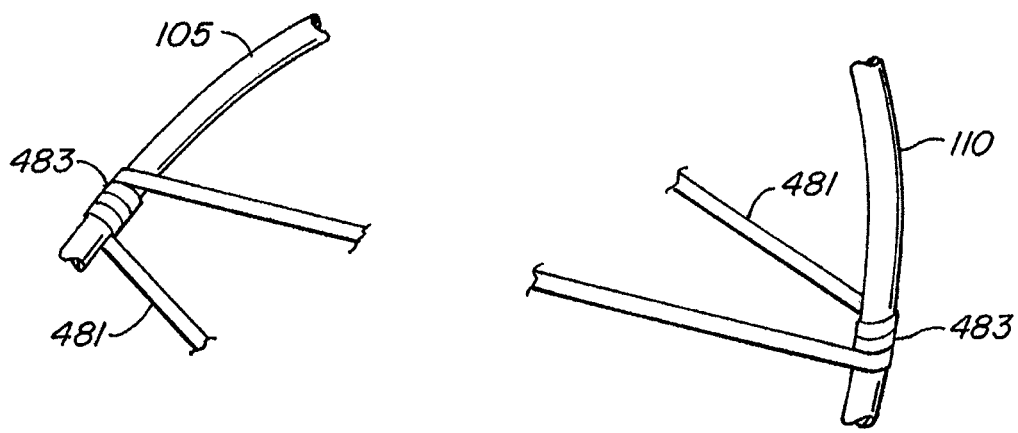

FIGS. 39 and 40 illustrate additional alternative techniques to secure a filter support structure to a support member. As illustrated in FIG. 39, there is illustrated a technique to secure a material capture structure securing line 351 to a support frame 105 using a material 481 wrapped around the support frame 105. In this manner, the material capture structure (not shown but attached to the lines 351) is attached to a material 481 that at least partially covers the first support structure 105. The lines 351 are passed between the material 481 and the support structure 105 as the material 481 as wraps 483 are formed along the support structure 105. The lines 351 are omitted in the embodiment illustrated in FIG. 40 as the material 481 forms wraps 483 and is used to secure the material capture structure (not shown). In one embodiment, the material 481 forms a tissue ingrowth minimizing coating over at least a portion of support structure. Alternatively, the filtering structure (not shown) is attached to the support structure 105 using a tissue ingrowth minimizing coating 481.

Figure 41:
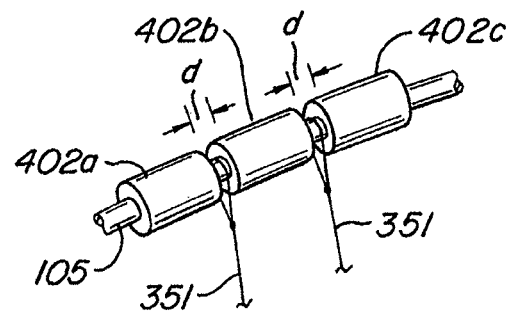
Figure 42:
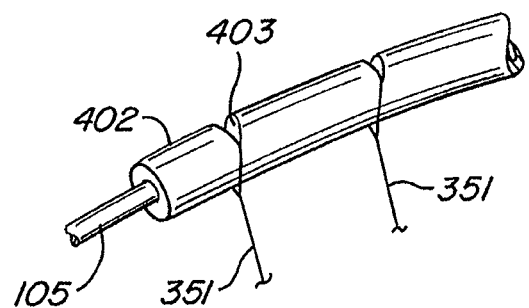
Figure 43:
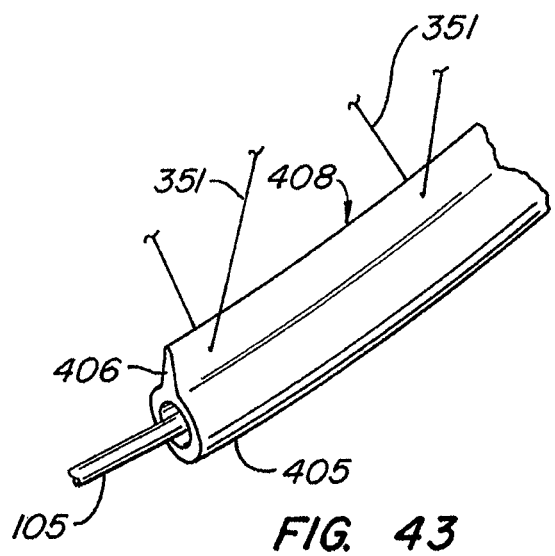

FIGS. 41, 42 and 43 relate to securing the material capture structure to a lumen disposed around the support member. FIG. 41 illustrates a lumen 402 that has been cut into segments 402a, 402b, 402c that are spaced by a distance "d." Lines 351 are attached around the support member and in the space "d" between adjacent segments. The segments may remain apart or be pushed together to reduce or eliminated the spacing "d." In contrast the segments in FIG. 41, the lumen 402 in FIG. 42 provides notches 403 for securing line 351. FIG. 43 illustrates a lumen 405 having a tissue growth inhibiting feature 408 extending away from the support member 105. As seen in section view 406 the inhibiting feature 408 has a different cross section shape than the support member 105. In addition, in some embodiments, the lumen 405 is selected from a suitable tissue ingrowth minimizing material so that is acts like a tissue ingrowth minimizing coating on the support structure. In other embodiments, the cross section shape 406 is configured to inhibit tissue growth over the tissue ingrowth minimizing coating.

Figure 44:
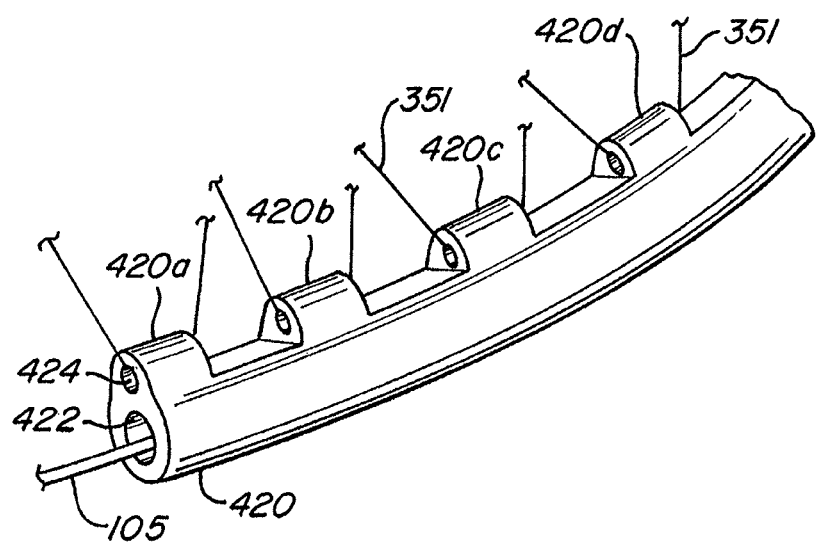
Figure 45:
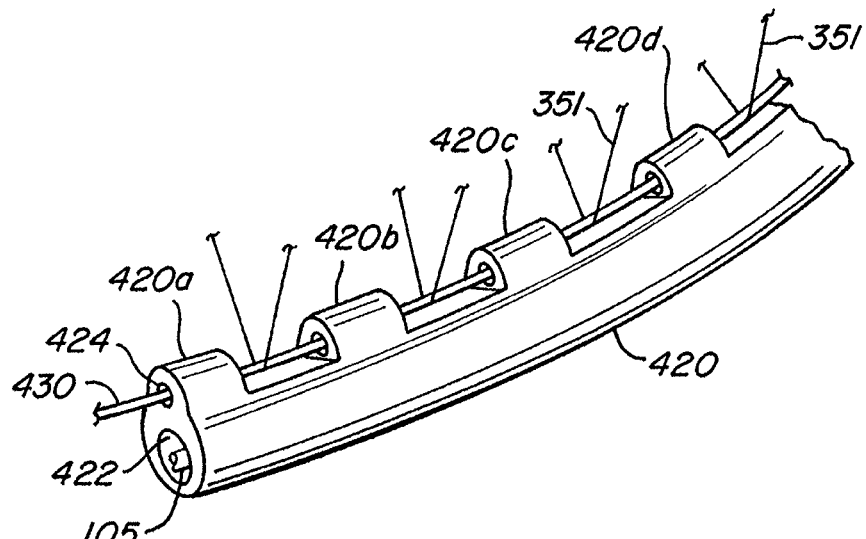

FIGS. 44 and 45 illustrate filter device embodiments utilizing dual lumen structures. The dual lumen structure 420 includes a lumen 422 and a lumen 424 and has a generally teardrop shaped cross section area. In this illustrative embodiment, the support structure 105 is disposed in the lumen 422 and the second lumen 424 is used to hold lines 351 and secure a material capture device (not shown). In the illustrative embodiment, the lumen structure 420 has been cut to form a number of segments 420a, b, c and d in the lumen 424. The connection rings formed by the segments 420a-d are used to secure lines 351 as needed. FIG. 45 illustrates an alternative configuration for the lumen structure 420. In this alternative configuration, a release line 430 extends through the notched lumen 424. The lines 351 extend about the release line 430 and hence to secure the material capture structure (not shown). Since the lines 351 are connected using the release line, removal of the release line from lumen 424 will allow the material capture structure secured using the lines 351 to be released from the support structure and removed from the lumen. A configuration such as that shown in FIG. 45 provides a filtering structure that would be releasably attached to an open loop (i.e., an open loop frame formed by the support structure). The embodiment illustrated in FIG. 45 provides a release line 430 positioned along the open loop (formed by member 105) and a filtering structure (not shown) is attached to the open loop using the release line.

In another embodiment, a filter device of the present invention is configured to be a coated endoluminal filter. In addition to coating all or a portion of the support structures or filter elements of this device, the coating on the support members may also be used to secure a filtering structure to the support structure. In one embodiment, a coated endoluminal filter has a support structure, a filtering structure attached to the support structure and a coating over at least a portion of support structure. In one aspect, the coated support structure may form a rounded support frame, an open loop or other structure to support a filtering structure described herein. In one embodiment, the coating over at least a portion of support structure is used to secure a plurality of loops (i.e., flexible form or rigid form) to the support structure. The plurality of loops are then used to secure a filtering structure such as a material capture structure, for example, within the coated endoluminal filter. In one embodiment, the coating is a tissue ingrowth minimizing coating.

It is to be appreciated that a filtering structure may also be attached to the support structure using the tissue ingrowth minimizing coating. In some embodiments, the tissue ingrowth minimizing coating is wrapped around the support structure or, alternatively, it may take the form of a tube. If a tube is used, the tube may be a continuous tube or comprise a plurality of tube segments. The tube segments may be in contact or spaced apart. The tube may have the same or different cross section shape than the support member. In another embodiment, the tissue ingrowth minimizing coating is in the shape of a tube and the support structure is in the interior of the tube.

In some other embodiments, a bonding material is provided between the tissue ingrowth minimizing coating and the support structure. The bonding material may be wrapped around the support structure or may take the form of a tube. If a tube is used, the tube may be a continuous tube or comprise a plurality of tube segments. The tube segments may be in contact or spaced apart. The bonding material tube may have the same or different cross section shape than the support member or the coating about the bonding material. In one embodiment, the bonding material is in the shape of a tube with the support member extending through the bonding material tube lumen. In one embodiment, a plurality of loops (i.e., flexible form or rigid form) are secured to the support structure by sandwiching the line used to form the loops between a bonding material around the support member and a coating around the bonding material. In one embodiment, the bonding material has a lower reflow temperature than the coating around the boding material. In this embodiment, the line used to form the loops is secured at least in part by reflowing the bonding material to secure the line between the coating around the bonding material and the support structure. In another alternative, the coating around the bonding material is a shrink fit coating that also shrinks around the bonding structure and the support member during or after a process that reflows the bonding material. In any of the above alternatives, the plurality of loops may be used to secure a filtering structure such as a material capture structure, for example, within the coated endoluminal filter.

Some embodiments of the coated endoluminal filter include some or all of the other features described herein such as, for example, a retrieval feature on the support structure, a retrieval feature on each end of the support structure, a support structure having two elongate bodies that are joined together to form a rounded frame, and a support structure having two spiral shaped elongate bodies. In addition, some coated endoluminal filters have a support structure that is generally symmetrical about a plane that is orthogonal to the flow direction of the filter and contains a crossover point. In another alternative coated endoluminal filter embodiment, the support structure of the coated endoluminal filter is generally symmetrical about a plane that is parallel to the flow direction of the filter and contains both ends of the support structure.

Figure 46:
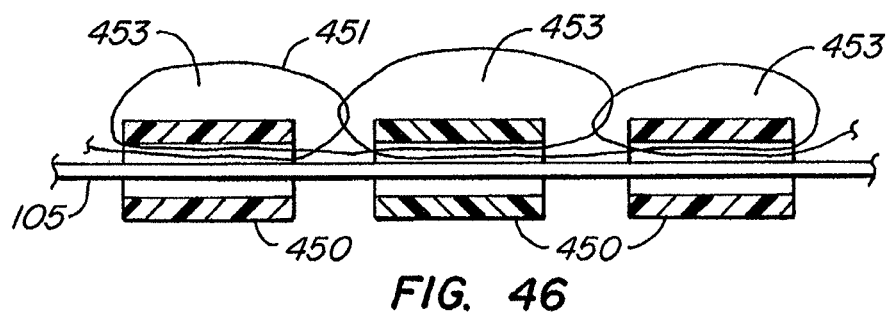
Figure 47:
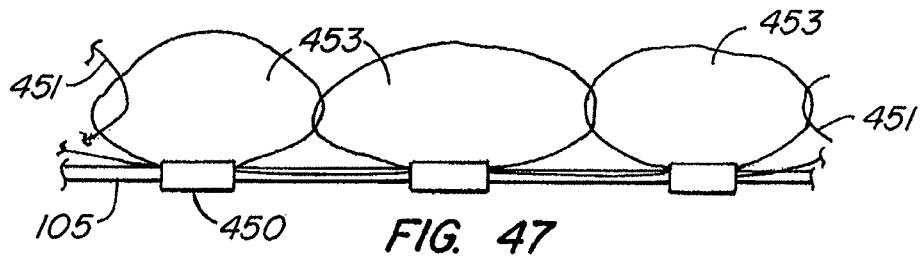

FIGS. 46-51B illustrate several aspects of coated endoluminal filter embodiments. These figures are not to scale and have exaggerated dimensions to make clear certain details. FIG. 46 illustrates a number of segments 450 of a coating placed about the support member 105. One or more lines 451 extend between the segment 450 and the support member 105 and form a plurality of loops 453. In one embodiment, the line 451 is a single continuous line. Once formed, the segments 450 undergo suitable processing to shrink the segment diameter around the line 451 and the support member 105 thereby securing the line 451 and loops 453 against the support structure (FIG. 47). The segment 450 is secured about the support member 105 as illustrated in the end view of FIG. 51A. The segments 450 in the embodiment shown in FIG. 47 are spaced apart. In other embodiments, the segments 450 may be in contact or have spacing different from that illustrated in FIG. 47. The sizes of the various components illustrated in FIGS. 46, 47 and 51A are exaggerated to show detail. The dimensions of one specific embodiment are: the support member 105 is a NiTi wire having an outside diameter of between 0.011" and 0.015"; the segments 450 are 0.2" long cut from a PTFE heat-shrink tubing having and a pre-shrunk outside diameter of 0.018" and a wall thickness of 0.002"; the line 451 is monofilament ePTFE of an outer diameter of 0.003" and the loops 453 have a nominal diameter of between about 0.1" to about 0.4".

Figure 48:
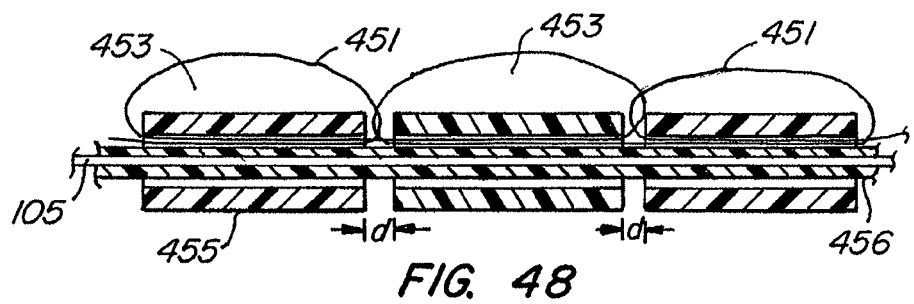
Figure 49:
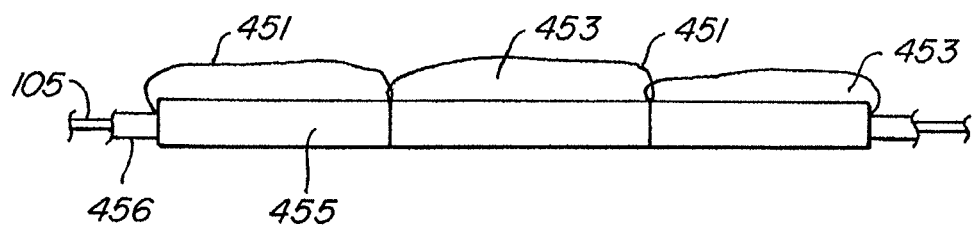

FIGS. 48, 49 and 51B illustrate a bonding material 456 about the support member 105 and a number of segments 455 about the bonding material 456. One or more lines 451 extend between the segments 455 and the bonding material 456 and form a plurality of loops 453. In one embodiment, the line 451 is a single continuous line. Once formed, bonding material 456 and/or the segments 450 undergo suitable processing to secure the line 451 between the bonding material 456 and the coating 455 thereby securing the line 451 and loops 453 against the support structure (FIG. 49). The coating segment 450 and the bonding material 456 is secured about the support member 105 as illustrated in the end view of FIG. 51B. The segments 455 in the embodiment shown in FIG. 48 are spaced apart by spacing "d." In other embodiments, the segments 455 may be in contact after processing (FIG. 49) or have spacing different from that illustrated in FIG. 48. In a preferred embodiment, the spacing between the segments 455 is removed by a portion of the boding material 456 flowing between and securing adjacent segments 455. The sizes of the various components illustrated in FIGS. 48, 49 and 51B are exaggerated to show detail. The dimensions of one specific embodiment are: the support member 105 is a NiTi wire having an outside diameter of between 0.011" and 0.016"; the segments 455 are 0.3" long cut from a PTFE heat-shrink tubing having a pre-shrunk outside diameter of 0.022" and a wall thickness of 0.002"; the bonding material is a tube of FEP heat shrink tubing having a pre-shrunk outside diameter of 0.018" and a wall thickness of 0.001"; line 451 is 0.002" outer diameter PET monofilament and the loops 453 have a nominal diameter of between about 0.1" to about 0.4". It is to be appreciated that the segments 450, 455 and bonding material 456 may be formed, for example, from: ePTFE, PTFE, PET, PVDF, PFA, FEP and other suitable polymers. Moreover, embodiments of strands, lines, fibers and filaments described herein may also be formed from ePTFE, PTFE, PET, PVDF, PFA, FEP and other suitable polymers.

FIG. 50 illustrates the use of a continuous flexible line 452 passed through a continuous coating segment 450 forming loops 454. The loops 454 are disposed along the length of the coating 450 at regular intervals; the continuous coating segment 450 are uniform in length to the support members 105 using a PTFE heat shrink tubing having pre-shrunk diameter of 0.018" and a wall thickness of 0.002". The line 452 is monofilament ePTFE of an outer diameter of 0.003" and the loops 454 have a nominal diameter of between about 0.1" to about 0.4".

Figure 58:
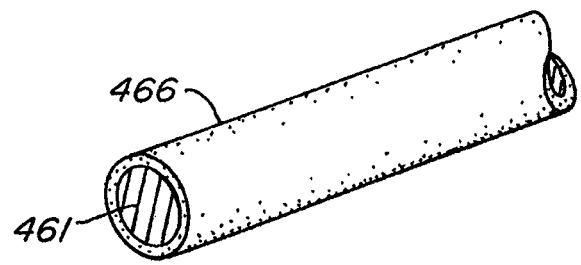

FIGS. 52A-53D illustrate alternative techniques for forming and/or attaching a filtering structure to a support structure. FIG. 52A illustrates an embodiment of a support frame 126 formed by support members 105, 110 between the end 102 and crossover 106 as described above. Loops 453/454 are formed using lines 451/452 as described above with regard to FIGS. 46-51B. Thereafter, a filament 461 is suitably attached 462 to a line 451/452 by tying, welding, gluing or by incorporating the filament 461 during the processing steps described with regard to FIGS. 46-51B. Next, the filament is traverses across the frame 126 and about the loops 453/454. In this embodiment, the lacing pattern between loops crosses a line extending between the end 102 and the crossover 106. The general pattern is that the filament extends across the frame 126 and around one right side loop (1) and back across the frame 126 (2) and around (3) a left side loop 453/454. The lacing process continues as shown in FIGS. 52B and 52C. When completed, the lacing process produces a filtering structure 465 from one or more filaments secured to loops 451/452 that are secured to the support members 105/110. The filament in the filtering structure 465 may be taut between the loops 451/452 or have some degree of sag (as illustrated in FIG. 52D). Filament 461 or other material used to form material capture structure may be coated with a pharmacological agent (coating 466 in FIG. 58). The pharmacological agent may be any of a wide variety of compounds, drugs and the like useful in the procedures performed using or the operation of various filtering device embodiments of the present invention. The pharmacological agent coating 466 may include pharmacological agents useful in preventing or reducing thrombus formation on the filtering structure, chemically lysing debris captured in the filtering structure and the like.

Figure 53A:
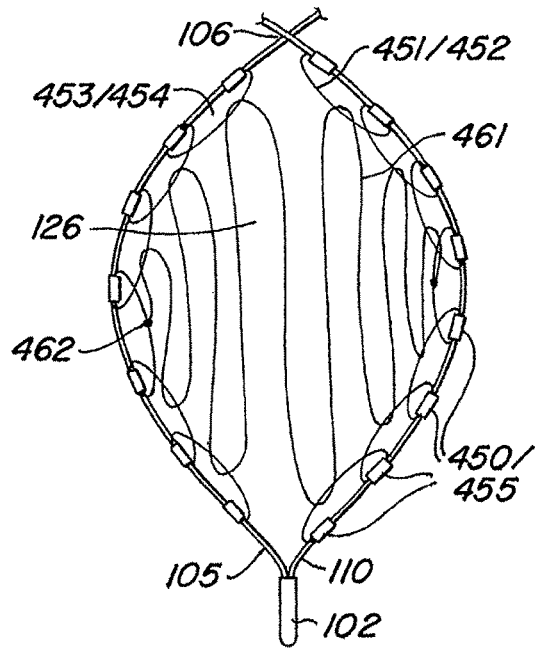
Figure 53B:
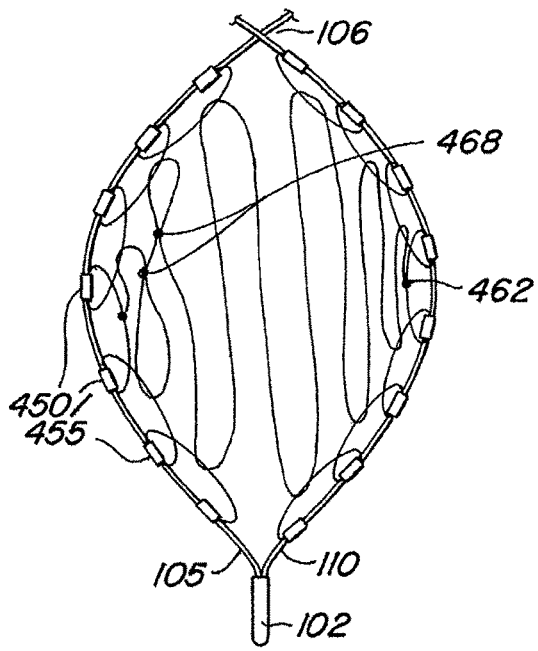
Figure 53C:
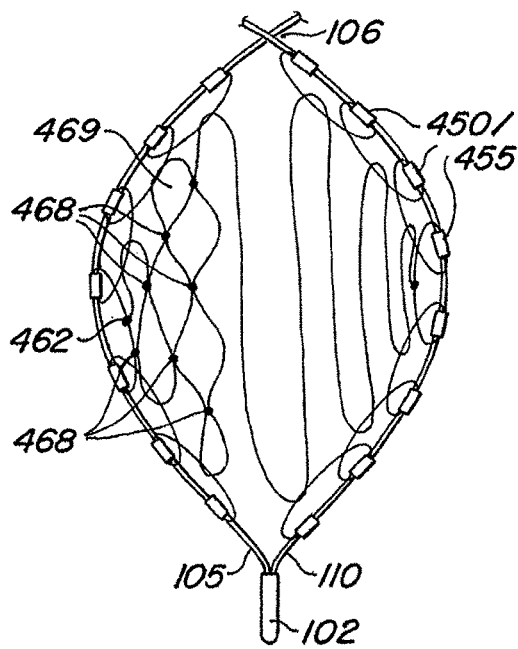
Figure 53D:
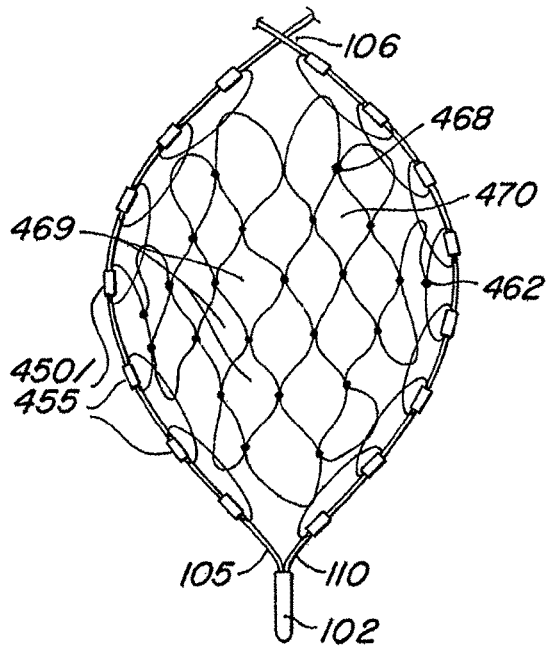

FIG. 53A illustrates an embodiment of a support frame 126 formed by support members 105, 110 between the end 102 and crossover 106 as described above. Loops 453/454 are formed using lines 451/452 as described above with regard to FIGS. 46-51B. Thereafter, a filament 461 is suitably joined 462 to a line 451/452 by tying, welding, gluing or by incorporating the filament 461 during the processing steps described with regard to FIGS. 46-51B. Next, the filament 461 was laced as described above with regard to FIG. 52A about the loops 453/454. In this embodiment, however, the lacing pattern between loops remains generally parallel to a line extending between the end 102 and the crossover 106. When completed, the lacing process produces a filtering structure from one or more filaments 461 that extend parallel to a line between the end 102 and crossover 106 and are secured to loops 451/452 secured to the support members 105/110. This filtering structure (FIG. 53A) may be used within a filter device of the present invention. In addition, the filtering structure in FIG. 53A (as well as the structure in FIG. 52D) may be further processed to join 468 adjacent filaments 461 to form filter cells 469 as part of a filtering structure 470. The process used to join 468 adjacent filaments 461 may include any conventional joining technique such as tying, welding, bonding, gluing, and the like. In addition, segments of tubing (i.e., segments 450, 455 456 described above) could be used to join 468 portions of adjacent filaments 461. In one specific embodiment, the filament 461 is ePTFE monofilament with an outer diameter of 0.003" joined 468 using a piece of FEP heat shrink tubing having a pre-shrunk outer diameter of 0.008" and a wall thickness of 0.001". The filtering structure 470 may be taut between the loops 451/452 or have some degree of sag (as illustrated in by the filtering structure in FIG. 52D). The filter cells 469 may be formed in numerous sizes and shapes as described in greater detail below.

Figure 57A:
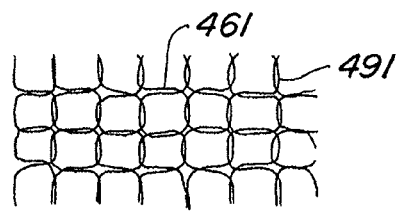

Alternatively, the filtering structures in FIG. 53A and FIG. 52D may incorporate additional loops 491 formed by looping the filament 461 as illustrated in FIG. 57A.

Alternative Filtering and/or Material Capture Structures

In some embodiments, the material capture structure contains a number of filter cells. Filter cells may be formed in a number of different ways and have a number of different shapes and sizes. The shape, size and number of filter cells in a specific filter may be selected based on the use of a particular filter. For example, a filter device of the present invention configured for distal protection may have a filter cell size on the order of tens to hundreds of microns to less than 5 millimeters formed by a selecting a filter material with a pore size (FIG. 63A, 63B) suited to the desired filtration level. In other applications, the filter cell may be formed by overlapping (i.e., joined or crossed without joining) filaments to form cells that will filter out debris in a lumen above a size of 2 mm. Various other filter sizes and filtration capacities are possible as described herein.

Figure 57B:
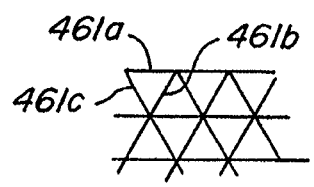

Intersecting filaments (FIG. 54C) may be used to form diamond shaped filter cells (FIG. 54A), as well as rectangular shaped filter cells (FIGS. 54B, 2A and 9B). Multiple strand patterns may also be used such as the three strand 461a, 461b and 461c array illustrated in FIG. 57B. Intersecting filaments may also be knotted, tied or otherwise joined 468 (FIGS. 55A and 55E). Intersecting filaments may form the same or different filter cell shapes such as, for example, an elongated oval in FIG. 55C, one or more joined diamonds as in FIG. 55B and an array of joined polygons as in FIG. 55D. Cells may also be formed using the techniques described above in FIGS. 52A-53D. In one embodiment, a filter cell is defined by at least three intersecting filaments 461. The filter element 461 may be formed from any of a wide variety of acceptable materials that are biocompatible and will filter debris. For example, filaments, lines and strands described herein may be in the form of a multifilament suture, a monofilament suture a ribbon, a polymer strand, a metallic strand or a composite strand. Additionally, filaments, lines and strands described herein may be formed from expanded polytetrafluoroethylene (ePTFE), polytetrafluoroethylene (PTFE), Poly(ethylene terephthalate) (PET), Polyvinylidene fluoride (PVDF), tetrafluoroethylene-co-hexafluoropropylene (FEP), or poly(fluoroalkoxy) (PFA), other suitable medical grade polymers, other biocompatible polymers and the like.

The joined polygons may have any of the shapes illustrated in FIGS. 60A-60F. It is to be appreciated that filter cells may have any, one or more, or hybrid combinations of shapes such as, for example, circular (FIG. 60A), polygonal (FIG. 60B), oval (FIG. 60C), triangular (FIG. 60D), trapezoidal or truncated conical (FIG. 60E).

Figure 56:
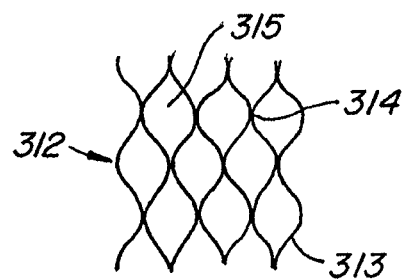

In addition, the material capture structure may have filter cells formed by extruding a material into a material capture structure. FIG. 56 illustrates an exemplary filtering structure 312 where a material is extruded into strands 313 that are joined 314 and spaced apart for form one of more filter cells 315. In one embodiment, the strands are extruded from Polypropylene material, forming diamond shaped filter cells approximately 4 mm in height and 3 mm in width.

Figure 59A:
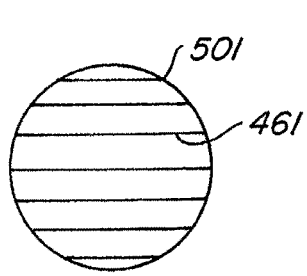
Figure 59B:
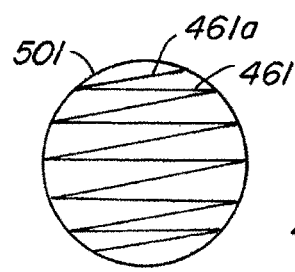
Figure 59C:
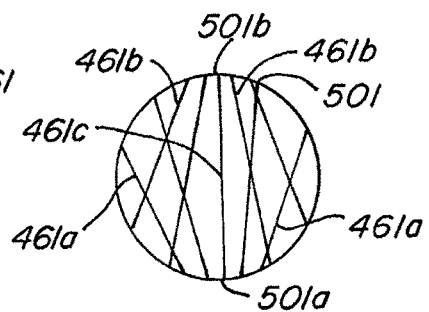
Figure 59D:
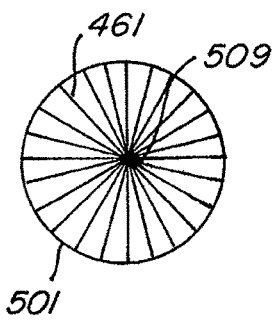
Figure 59E:
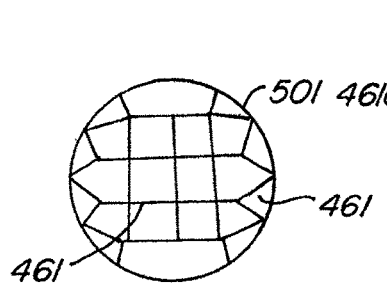

FIGS. 59A-63B illustrate several different filtering structure configurations. For simplicity of illustration, the filtering material is shown attached to a circular frame 501. It is to be appreciated that the circular frame 501 represents any of the various open loop, rounded frame or other support frames described herein. FIG. 59A illustrates a frame pattern similar to FIG. 52D. FIG. 59B adds an additional transverse filaments 461a at an angle to the filaments 461. FIG. 59C illustrates a plurality of filaments 461a extending up from the frame bottom 501a about a central filament 461c and a plurality of filaments 461b extending down from the frame top 501b about a central filament 461c. In this illustrative embodiment, the filaments 461a,b are arranged symmetrically about the central filament 461c. Other non-symmetrical configurations are possible. More than one central filament 461c may be used to form a variety of different size and shaped polygonal filter cells (e.g., FIG. 59E).

Figure 59F:
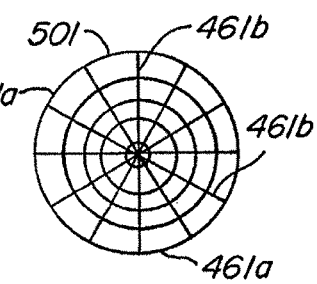
Figure 59G:
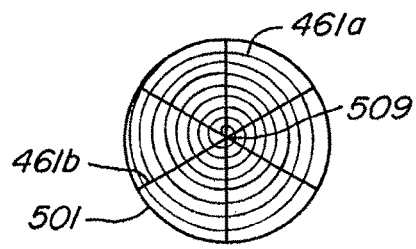

Filaments may also be arranged using a variety of radial patterns. Fr example, multiple filaments 461 may from a common point 509 out the edge of frame 501. In some embodiments, the common point is central to the frame 501 (FIG. 59D) and in other embodiments the common point 509 is in a different, non-central location. The sectors formed by the multiple filaments (FIG. 59D) may be further divided into multiple filter cell segments by winding a filament 461a about and across segment filaments 461b. In contrast to a single filament spirally out from the point 509 as in FIG. 59G, the segmented filter cells in FIG. 59F are formed by attaching single filament 461a to the segment filaments 461b.

Figure 61A:
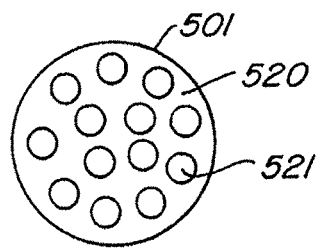
Figure 61B:
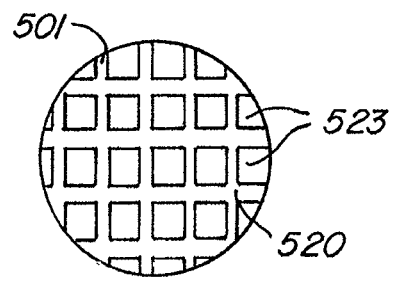
Figure 61C:
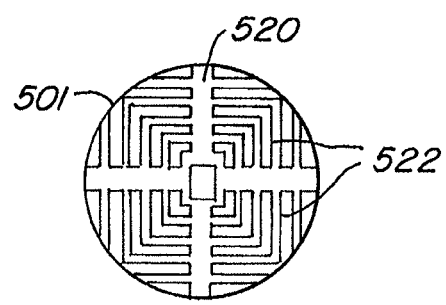
Figure 62:
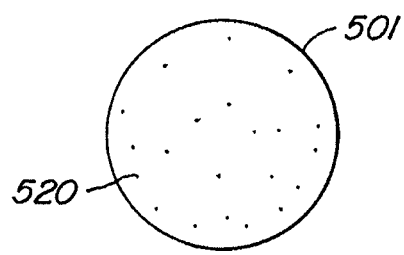
Figure 63A:
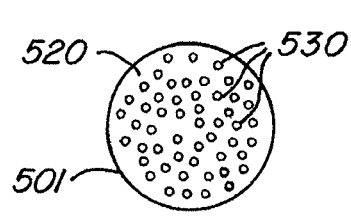
Figure 63B:
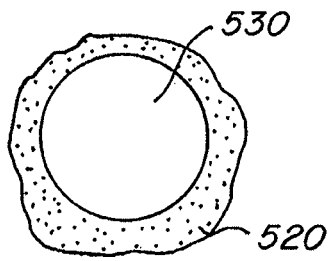

FIGS. 61A-C and FIG. 62 illustrate the use of a sheet of material 520 to form a filter structure. The material 520 may have any of a variety of shapes formed in it using any suitable process such as punching, piercing, laser cutting and the like. FIG. 61A illustrates a circular pattern 521 formed in material 520. FIG. 61B illustrates a rectangular pattern 523 formed in material 520. FIG. 61C illustrates a complex pattern 522 cut into material 522. It is to be appreciated that the material 520 may also be placed in the frame 501 without any pattern (FIG. 62). The illustrative embodiment of FIG. 62 may be useful for occluding the flow within a lumen. Suitable materials 520 for an occlusion application include for example, wool, silk polymer sheets, other material suited to prevent blood flow in a lumen when extended across a lumen and the like. Additionally, the filter material 520 may be a porous material having pores 530 (FIG. 63A). The material 520 may be selected based on the average size of individual pores 530 (FIG. 63B) depending upon the procedure or use of the filter device. For example, the material 520 may be any of the porous materials using in existing distal protection and embolic protection devices. In general, a wide variety of pore 530 sizes are available and may range from 0.010" to 0.3". Other pore sizes are also available depending upon the material 520 selected.

Figure 64A:
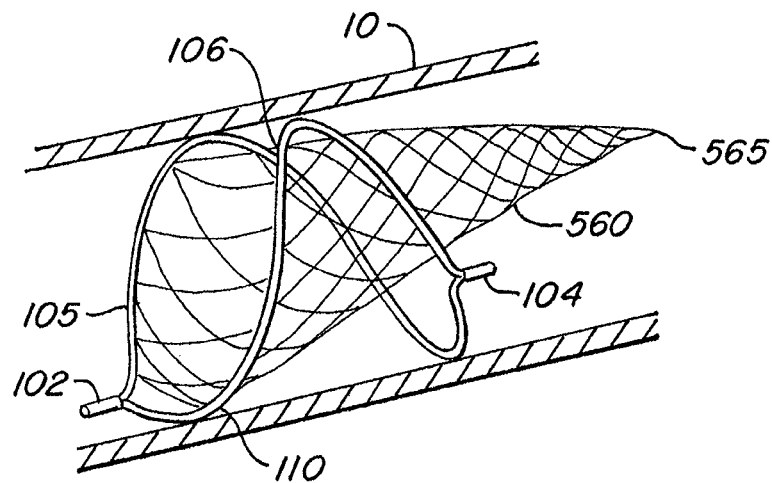
Figure 64B:
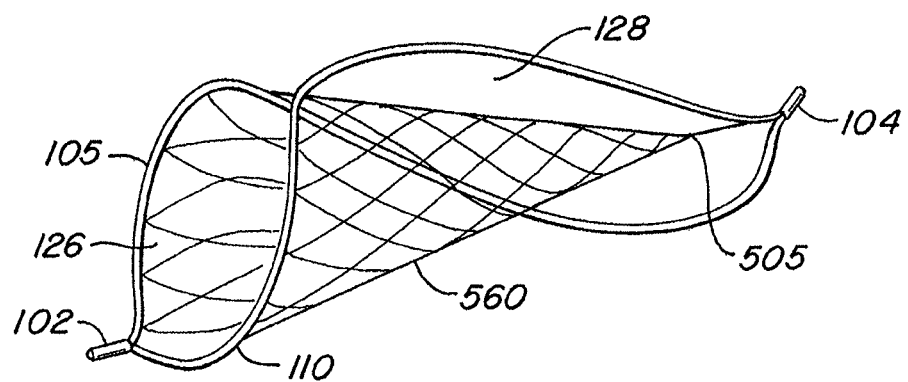
Figure 65A:
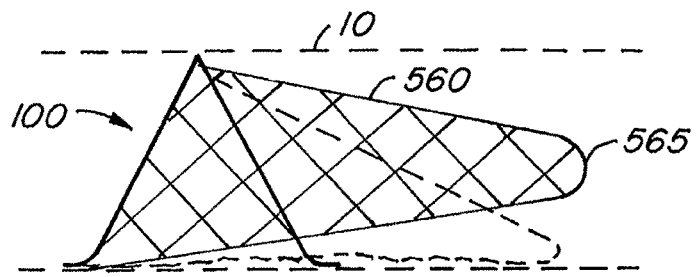
Figure 65B:
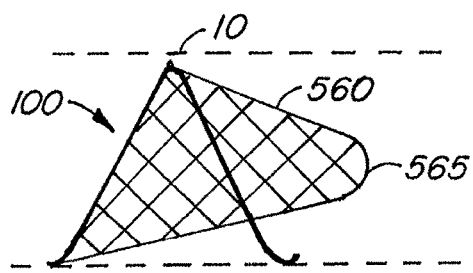
Figure 65C:
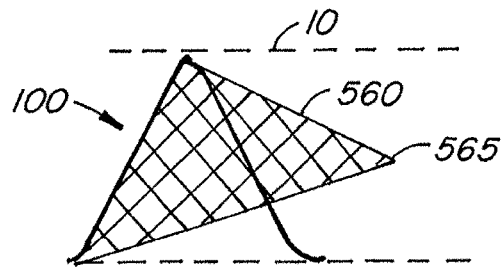
Figure 65D:
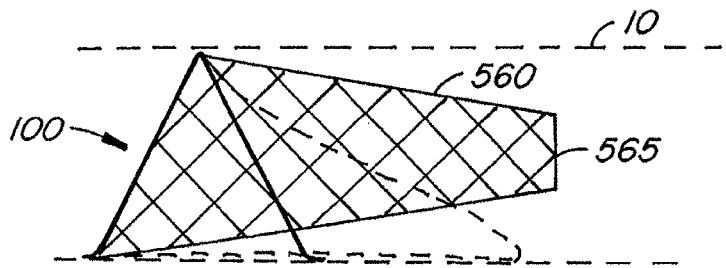
Figure 65E:
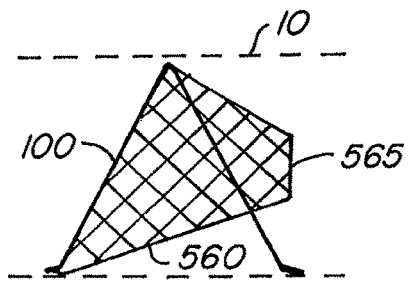
Figure 65F:
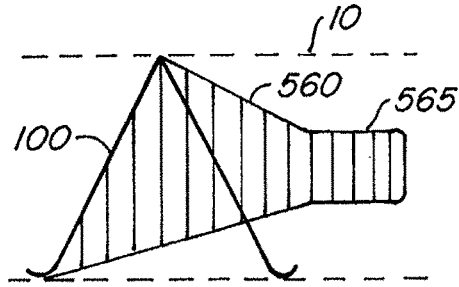

FIGS. 64-65F illustrate the use of nets or other web structures within the filtering device. The various net structure embodiments described herein are used as material capture structures within filter device embodiments of the present invention. Each of these alternative is illustrated in a support structure similar to that of device 100 in FIG. 2A and elsewhere. When deployed within the lumen 10, the material capture structure 560 has a defined shape such as a cone with a discrete apex 565 (FIG. 64A). In this embodiment, the net structure is long enough to contact the sidewall of the lumen 10 when deployed in the lumen 10. Alternatively, the apex 565 may be attached to the end 104 to keep the net 560 in the lumen flow path and out of contact with the lumen sidewall (FIG. 64B). The net 565 may also have a rounded apex 565 (FIG. 65A) or a truncated cone (flat bottom) (FIG. 65D). Alternatively, the net 560 may a discrete apex 565 so short that it will not contact the lumen sidewall when deployed (FIG. 65B). The short net may also have a rounded apex 565 (FIG. 65B), a flat apex (FIG. 65E) or a sharp apex (FIG. 65C). In addition, the net 560 may have a compound apex 565 (FIG. 65F).

Figure 66:
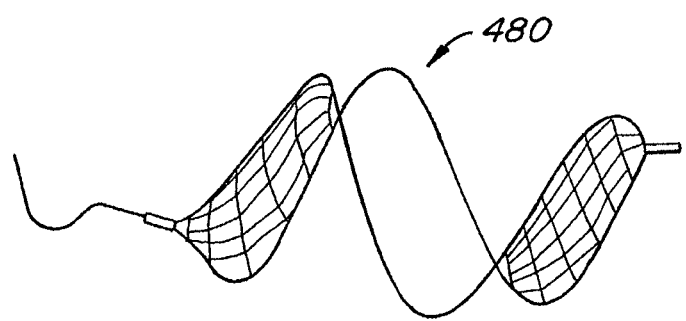
FIGS. 66 and 67 illustrate various filtering device configurations.
Figure 67:
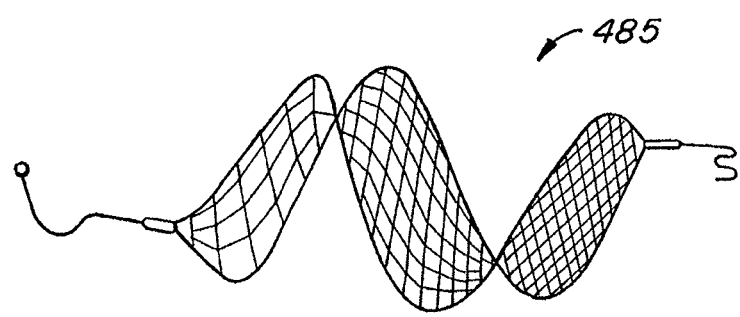

FIGS. 66 and 67 illustrate how various different features described above can be combined. For example, FIG. 66 illustrates a multi-support frame device 480 having a retrieval feature on only one end and an open frame (i.e., no filter structure). FIG. 67 illustrates an alternative multi-support frame device 485 having different retrieval features on each end, filter structures in each of the support structures and each of the filter structures having a different filter capacity. It is to be appreciated that the above described details of the construction, components, sizes, and other details of the various filter device embodiments described herein may be combined in a number of different ways to produce a wide array of alternative filter device embodiments.

Delivery, Recovery and Repositioning of a Filtering Device

Figure 68A:
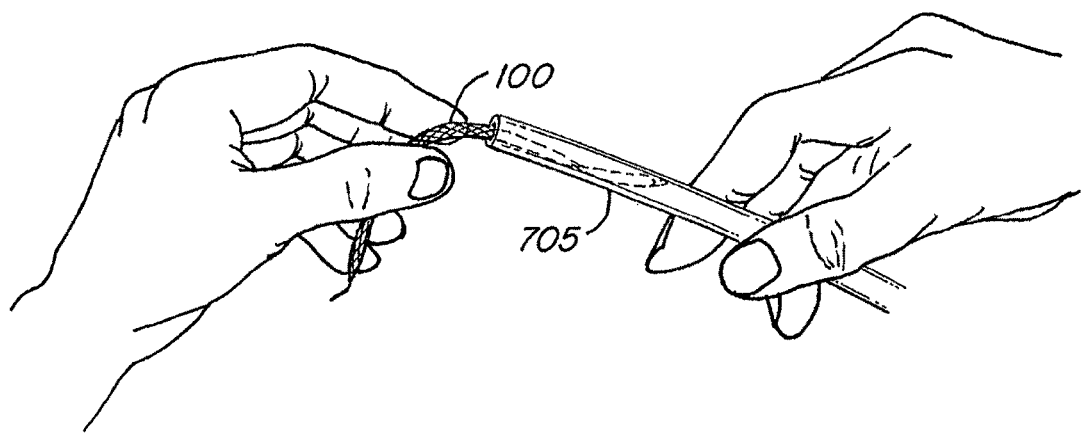
FIGS. 68A-74D illustrate various techniques related to the delivery, recovery and repositioning of filtering devices.
Figure 68B:
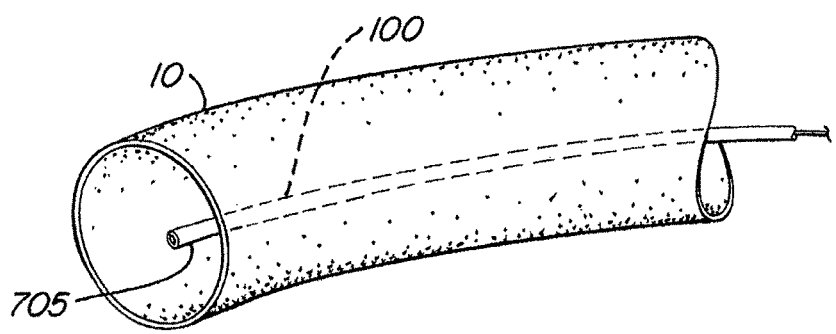

FIG. 68A illustrates an embodiment of the filter device 100 of the present invention loaded into an intravascular delivery sheath 705. The device 100 is illustrated and described above, for example, in relation to FIG. 16A. Using conventional endoluminal and minimally invasive surgical techniques, the device can be loaded into the proximal end of the sheath 705, before or after advancing the sheath 705 into the vasculature, and then advanced through the sheath using a conventional push rod. The push rod is used to advance the device 100 through the delivery sheath lumen as well as fix the position of the device (relative to the sheath 705) for device deployment. In one preferred technique, the device is loaded into the proximal end of a delivery sheath that has already been advanced into a desired position within the vasculature (FIG. 68B). The device 100 may be preloaded into a short segment of polymeric tubing or other suitable cartridge that allows the device 100 to be more readily advanced through a hemostasis valve.

Figure 69A:
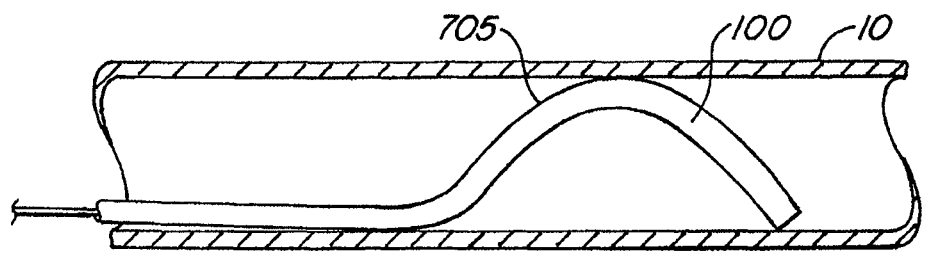
Figure 69B:
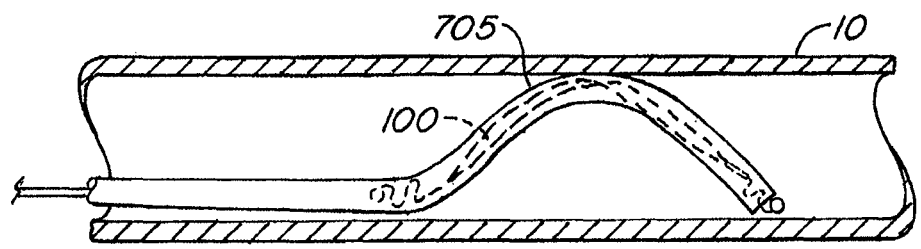
Figure 69C:
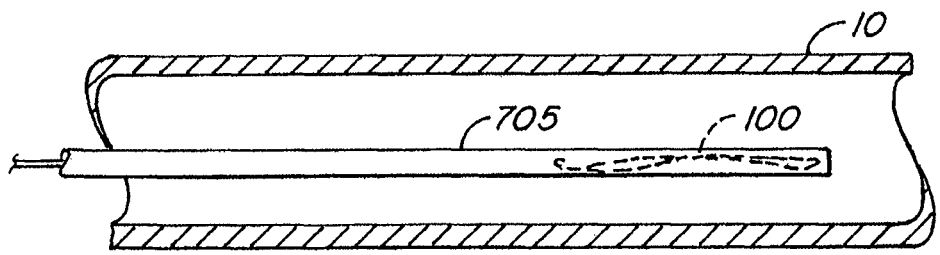
Figure 69D:
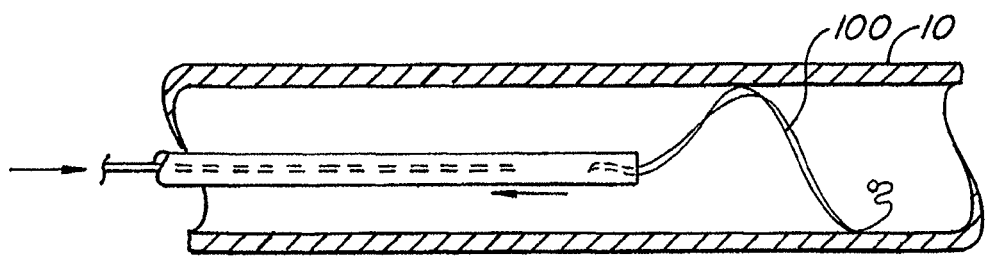

When used with a compliant delivery sheath 705, the pre-formed shape of the device 100 deforms the sheath to conform to the device shape (FIG. 69A, 69B). Accordingly, a flexible, compliant sheath 705 assumes the curvature of the stowed device. The deformation of the delivery sheath 705 helps stabilize the position of the sheath 705 in the vasculature and facilitates accurate deployment of the device 100 to the intended delivery site. In contrast, a non-compliant delivery sheath 705 (i.e., a sheath that is not deformed to conform to the preformed shape of the device 100) maintains a generally cylindrical appearance even through the device 100 is stowed within it (FIG. 69C). Regardless of the type of sheath used, device delivery is accomplished by using the push rod on the proximal side of the device to fix the position of the device within the sheath 705 and then withdrawing the sheath 705 proximally. As the device 100 exits the distal end of sheath 705, it assumes the pre-formed device shape (FIG. 69D).

Figure 70:
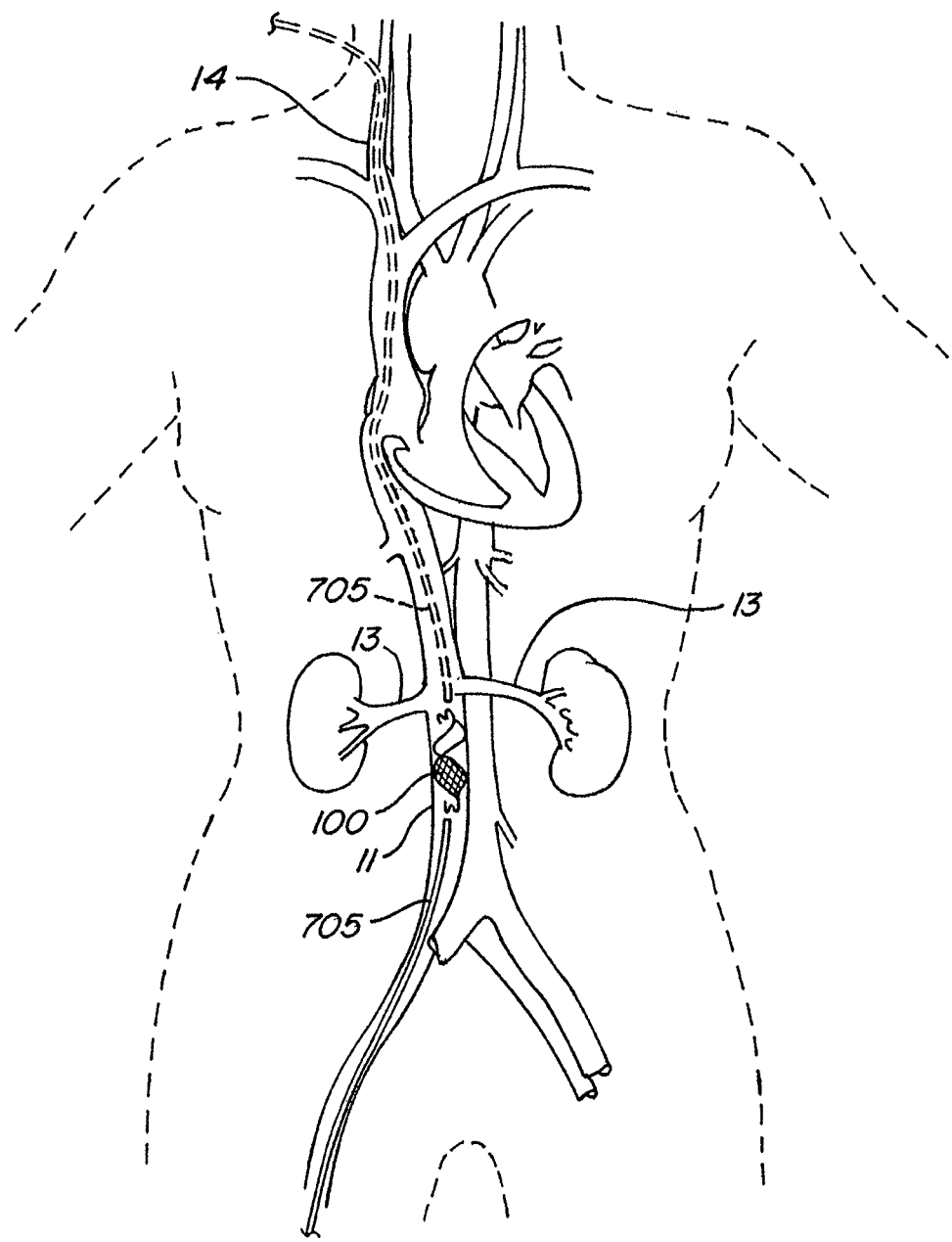

The symmetrical device shape (see e.g., devices in FIGS. 15 and 16A), facilitates the deployment and retrieval of the device from multiple access points in the vasculature. A device 100 is shown positioned in the vasculature within the inferior vena cava 11 immediately below the renal veins 13 (FIG. 70). A femoral access path (solid) and a jugular 14 access path (phantom) are illustrated. The femoral access path (solid) and a jugular access path may each be used for device deployment, repositioning and retrieval. Alternatively, the vena cava could be accessed via brachial or antecubital access for device deployment, repositioning and retrieval.

Figure 71A:
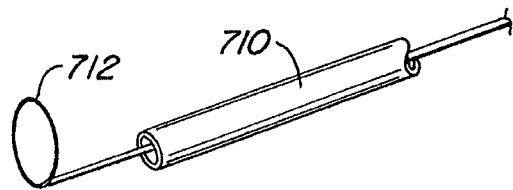
Figure 71B:
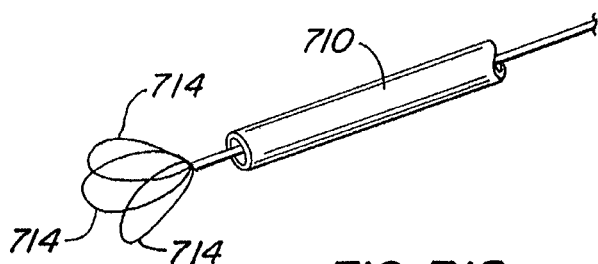

Retrieval of the devices is most preferably accomplished by endoluminal capture using one of the retrieval features described herein. (i.e., FIGS. 27A-E) The retrieval features described herein have been designed to work well using a commercially available snares two of which are illustrated in FIG. 71A and FIG. 71B. The single loop Gooseneck snare 712 is illustrated in FIG. 71 inside of a recovery sheath 710. The multiple loop Ensnare 714 is illustrated in FIG. 71B inside of a recovery sheath 710. These conventional snares are controlled by a physician using a flexible, integral wire.

Figure 72A:
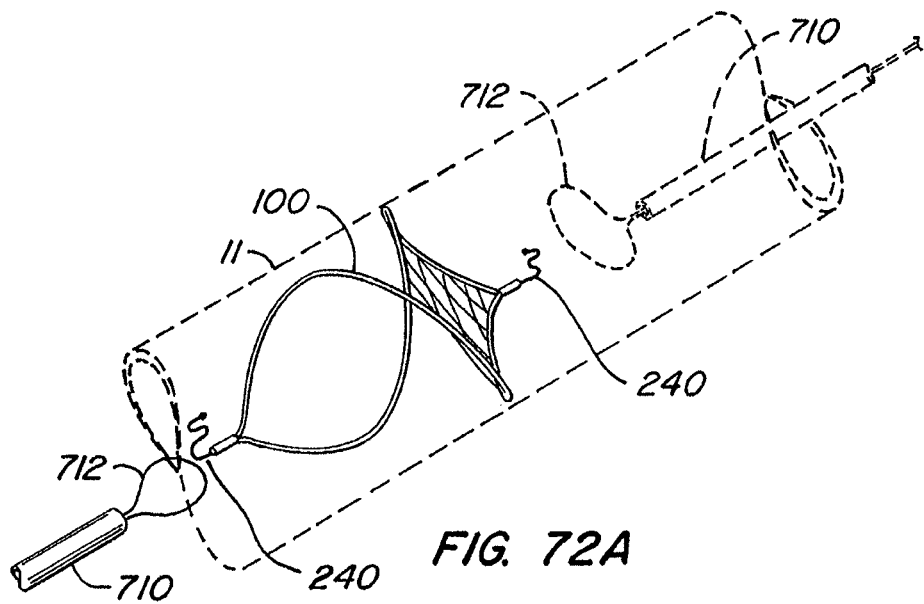
Figure 72B:
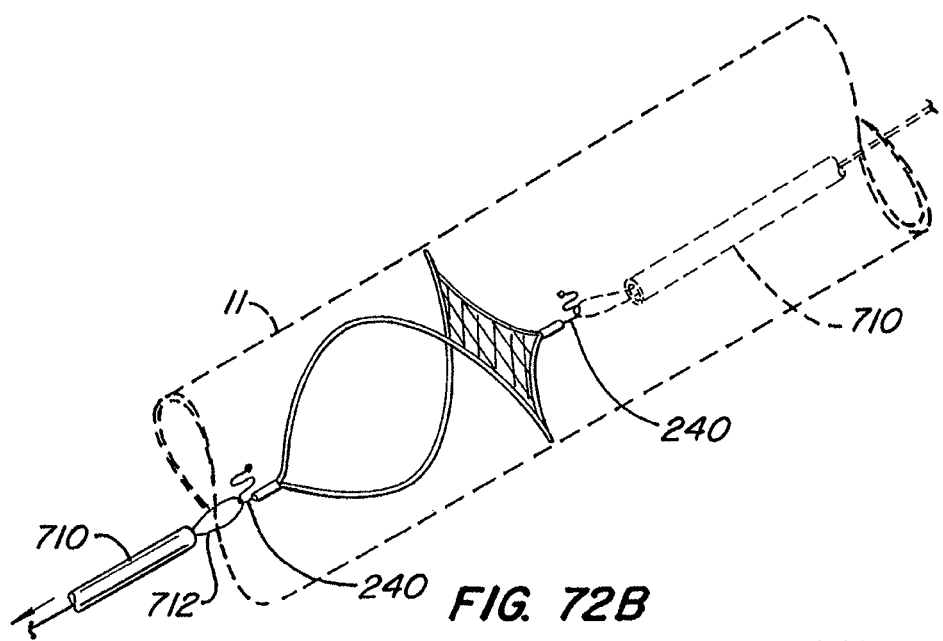
Figure 72C:
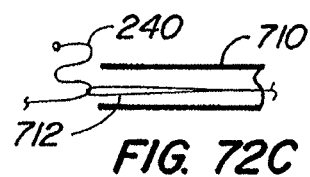
Figure 72D:
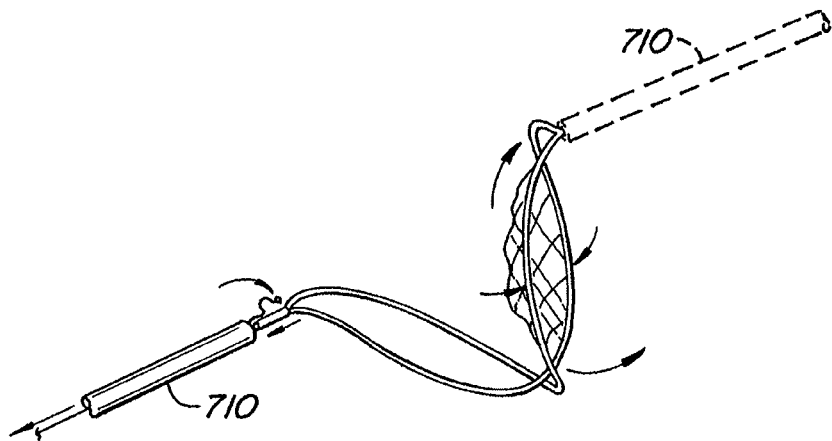

The sequence of device recapture and removal from a body lumen (here the vena caval 1) is illustrated in FIGS. 72A-C. In these figures, the solid lines are for a femoral recovery and the phantom lines are for a jugular recovery (e.g., FIG. 70). A collapsed snare is advanced via a delivery sheath to the proximity of the retrieval feature 240 (FIG. 72A). Once in place, the snare 712 is exposed and assumes a pre-defined expanded loop shape which is looped over the retrieval feature 240 as illustrated from either end in FIG. 72B.

The snared device 100 can then be either pulled into the sheath 710, or alternatively and more preferably, the recovery sheath 710 is advanced over the device 100 while maintaining positive control of the snare 712 as the sheath 710 advances over the device 100. Advancing the recovery sheath 710 over the device 100 facilitates atraumatic removal of the device 100 from any tissue that has grown in or around the device 100. The retrieval action, which tends to collapse the device radially inward (FIG. 72D), also facilitates removal from any tissue layer formed on the device. Recovering the filtering device by pulling on a flexible retrieval feature attached to the filtering device. Moreover, pulling on a portion of the filter structure (i.e., a retrieval feature) removes the opposing spiral elements from the lumen wall.

As the device is drawn into the sheath 710, the pre-formed shape of the device also urges the support members away from the lumen wall which also assists in atraumatic device removal.

Figure 72E:
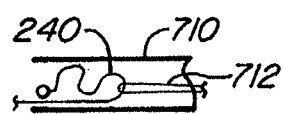
Figure 72F:
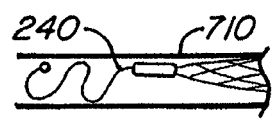
Figure 73A:
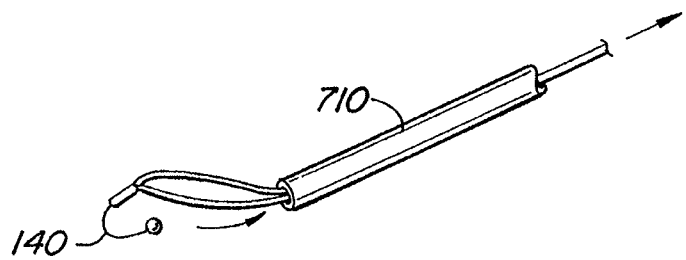
Figure 73B:
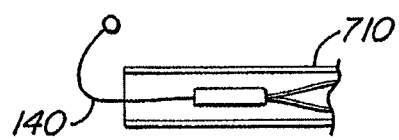
Figure 73C:
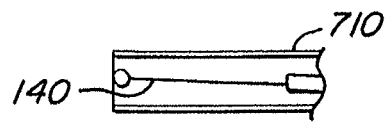
Figure 73D:
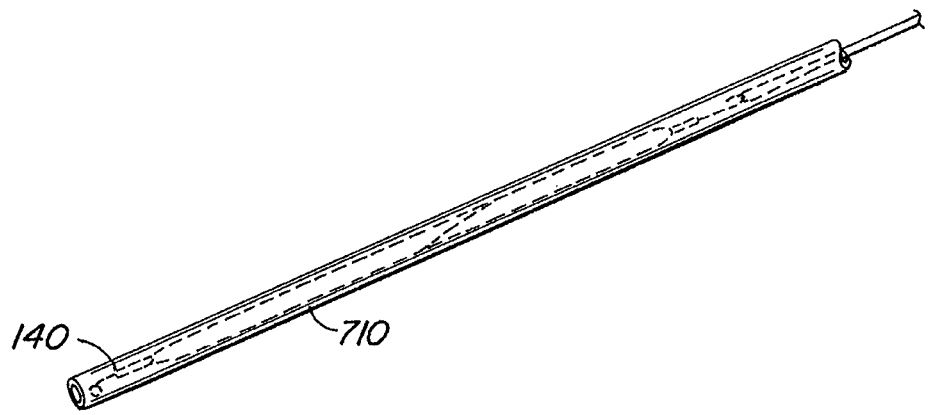

The flexible retrieval element 240 assumes a collapsed configuration as it is being drawn into the recovery sheath as illustrated in FIG. 72C and FIG. 72E. Note that the retrieval feature 240 on the opposite end of the device assumes a straightened configuration as is drawn into the recovery sheath (FIG. 72F). An additional embodiment, in which a single curved retrieval feature 140 (FIG. 27A) is withdrawn into the delivery sheath 710 as shown in FIG. 73A. The distal retrieval feature (relative to the snare) assumes a straightened configuration FIG. 73C from a curved configuration FIG. 73B as is completely withdrawn into the sheath FIG. 73D.

Additionally, repositioning the filter 100 from one lumen position to another is illustrated in FIGS. 74A-74D. Because of the atraumatic design of filter devices of the present invention, repositioning of the filter device 100 may be accomplished by fully recapturing (FIG. 74C) or only partially recapturing (FIG. 74B) the device 100 into a recovery sheath 710. The atraumatic design of the device 100 allows the device to simply secured by one end (FIG. 74B) and pulled along the lumen wall into the desired position and then released. The delivery sheath and recovery sheath are provided with the same reference numbers since filter devices of the present invention may be deployed into and recovered from the vasculature using sheaths that are about the same size. As such, devices of the present invention may be deployed into the vasculature from a delivery sheath having a first diameter. Then, the device may be retrieved from the vasculature using a recovery sheath having a second diameter no more than 2 Fr larger than the first diameter (1 Fr=0.013"=⅓ mm). Alternatively, the second diameter may be no more than 1 Fr larger than the first diameter or, alternatively, the first diameter is about the same as the second diameter.

Figure 74A:
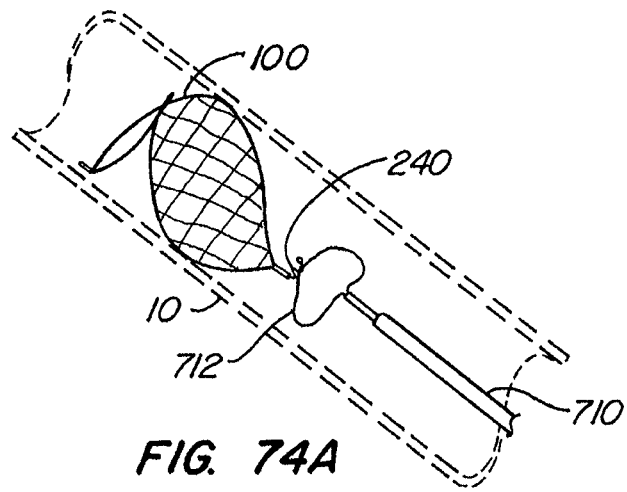
Figure 74B:
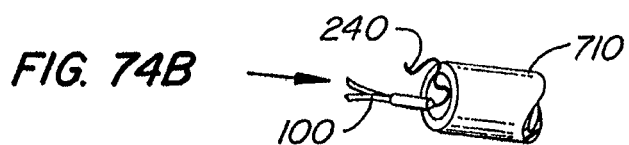
Figure 74C:
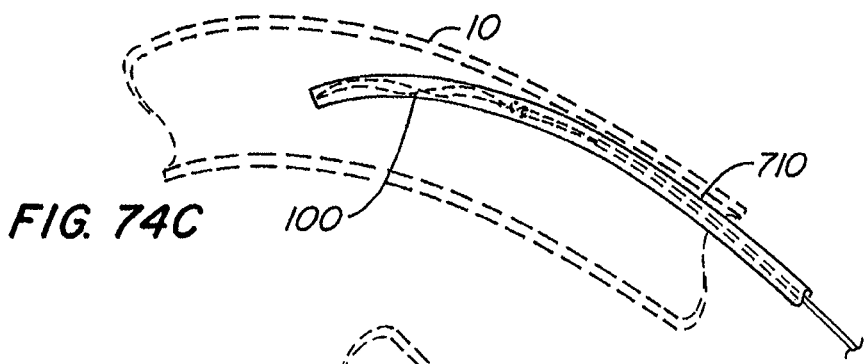
Figure 74D:
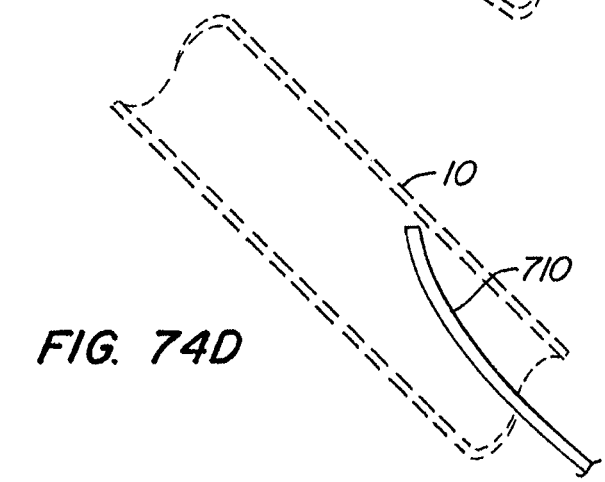

In a full recovery, the device is pulled completely into a recovery sheath (FIG. 74A), the sheath is repositioned from the original position (FIGS. 74A, 74C) to a second position (FIG. 74D) and deployed into the vasculature again (FIG. 69D). In the case where the snare wire columnar strength is insufficient to redeploy the device, the snare can be delivered within a secondary inner sheath within the retrieval sheath. This allows the positive control of the retrieval feature to be obtained, such as illustrated in FIG. 74B, the device withdrawn into the retrieval sheath and then redeployed with the inner sheath acting as a push rod.

Various Methods of Using Filtering Devices

Embodiments of filter devices of the present invention may be used in methods of providing distal protection in procedures such as, for example, thrombectomy, arthrectomy, stenting, angioplasty and stent grafting. It is to be appreciated that embodiments of filter devices of the present invention may be used in veins and arteries. An exemplary procedure is illustrated in FIGS. 75A-I and FIGS. 76A-E. In each procedure, the device 100 is positioned in an un-tethered fashion adjacent to the treatment region 730. The sequence FIGS. 75A-I illustrate the delivery sheath 710 positioning FIG. 75A, complete deployment FIG. 75B into the lumen 10. A conventional treatment device 750 using mechanical, electrical energy or other suitable method is used to clear the undesired material 732 from the lumen wall (FIG. 75C). Some debris 734 removed from the lumen wall through the use of treatment device 750 is subsequently embolized into the blood stream (FIG. 75C) and trapped by the filter 100 (FIG. 75D). The conventional treatment device 750 is removed (FIG. 75E) and thereafter the advancement of recapture sheath 710 is advanced into recovery position (FIG. 75F).

The entrapped debris 734 is then removed prior to recapturing the device with methods such as, for example, aspiration, delivery of therapeutic agents or maceration. Additionally, the device and entrapped debris can be recaptured in whole and removed via the same sheath used to recapture the device as illustrated in FIG. 75G. The device 100 and debris 734 are then withdrawn into the sheath 710 (FIG. 75H), and the sheath withdrawn from the vasculature (FIG. 75I).

Figure 76A:
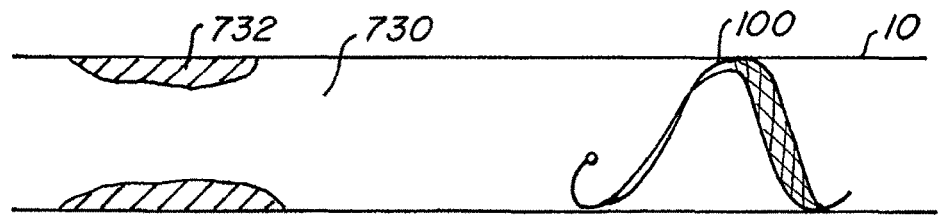
Figure 76B:
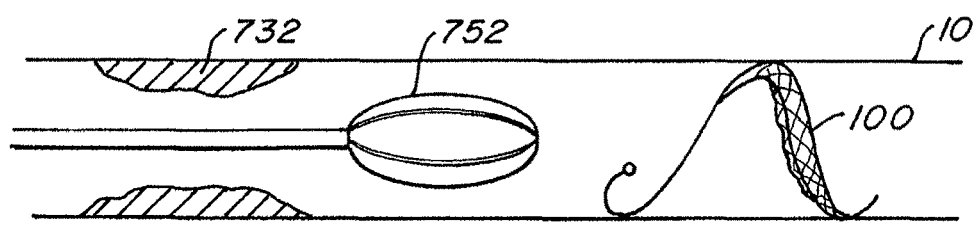
Figure 76C:
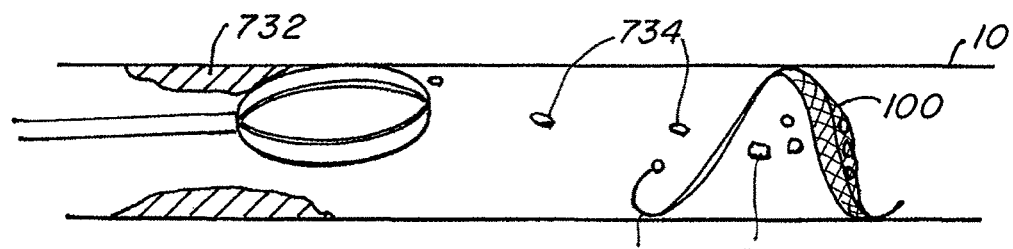
Figure 76D:
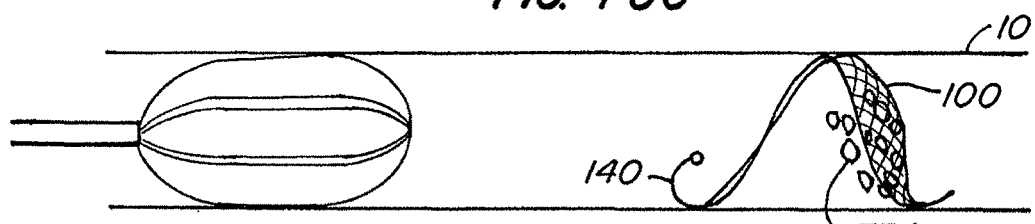
Figure 76E:
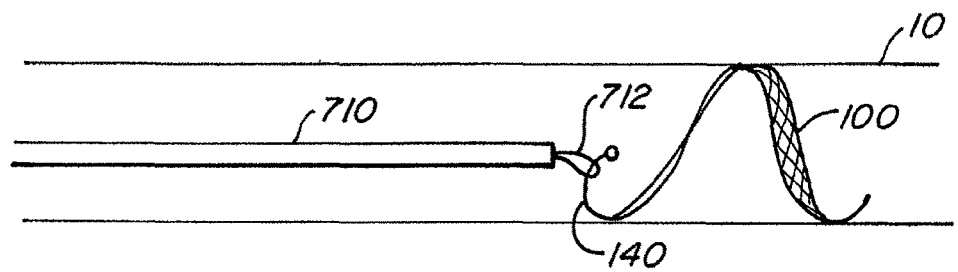

Similarly, an additional use of the invention as un-tethered distal protection is illustrated in FIGS. 76A-E, in which a balloon 751 is used to expand the lesion 732 such as in the case of balloon angioplasty, often performed prior to stenting a vessel to keep it open. For this procedure a balloon catheter is advanced to the lesion site and inflated FIG. 76 B, plaque 732 is pushed outward by the balloon (FIG. 76C), thus reestablishing normal blood flow. Any particulate matter 734 embolized by the procedure is trapped by the filter (FIG. 76D). The debris 734 can then be removed prior to filter retrieval as previously described or the device with trapped debris can be removed together.

Figure 77A:
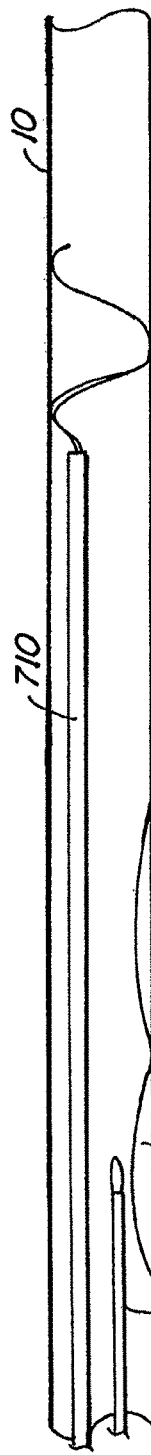
Figure 77B:
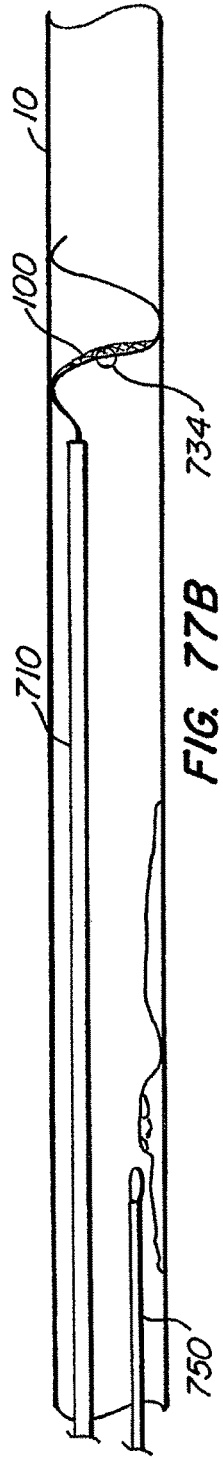

An additional method practiced widely in the art is the use of tethered distal protection adjunctive to the previously described procedures (i.e., the device 100 remains tethered during the procedure). Embodiments of the filtering device of the present invention may also be used for this purpose as illustrated in FIGS. 77A-77E. Positive control of the filter 100 is maintained via an integral wire or snare connected to the device 100. The connection between the integral wire or snare to the device 100 is maintained during the procedure and may be, in some embodiments, used as a guidewire. As illustrated in FIG. 77B, connection to the device 100 is maintained a while performing a procedure to treat the vasculature in proximity to the location (i.e., treat the lesion 732).

Figure 77C:
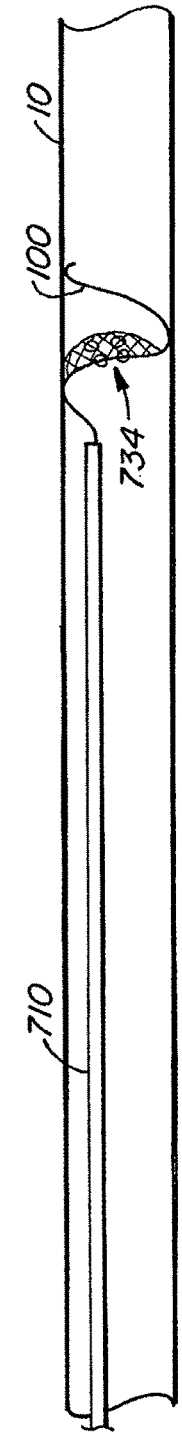
Figure 77D:
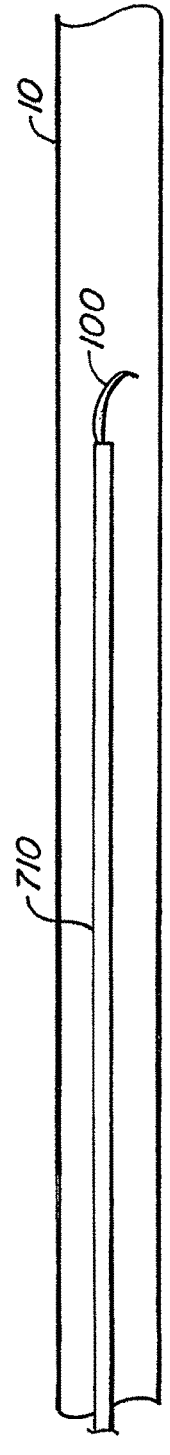
Figure 77E:
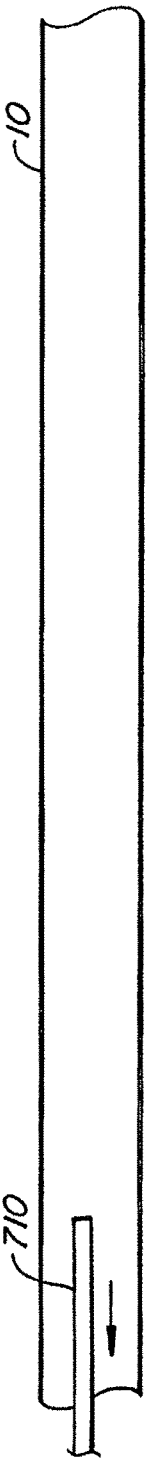

An example of a tethered distal protection method is illustrated in FIGS. 77A-77E. An embodiment of a filter device 100 is deployed distal to the lesion 732 to be treated (FIG. 77A), the treatment is initiated (FIG. 77B), and embolized material 734 is captured in the filter 100 (FIG. 77C). Thereafter, the debris 734 is removed prior to filter recapture or, alternatively, with treatment in the filter 100 via a sheath as previously described. The device 100 is recovered into the sheath (FIG. 77D) and removed from the lumen 10 (FIG. 77E).

Figure 78A:
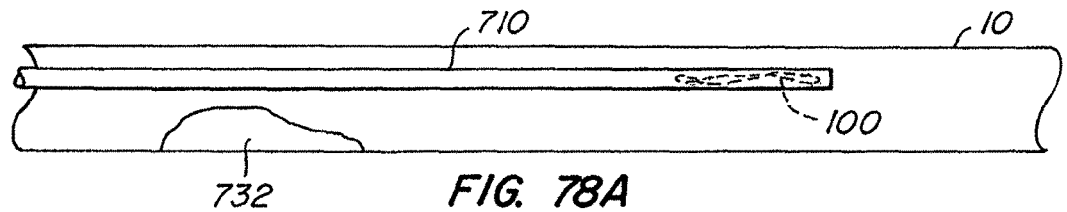
Figure 78B:
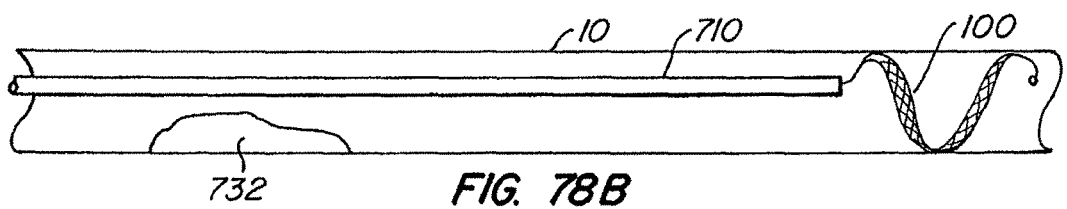
Figure 78C:
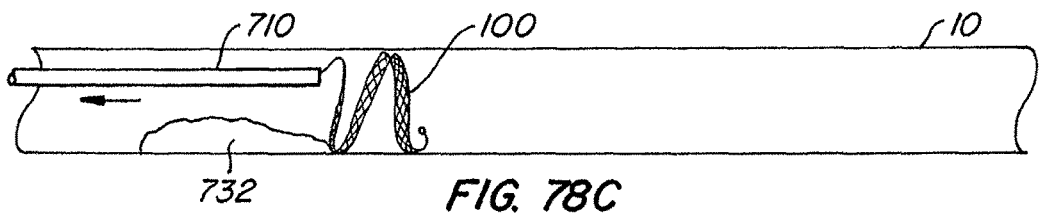
Figure 78D:
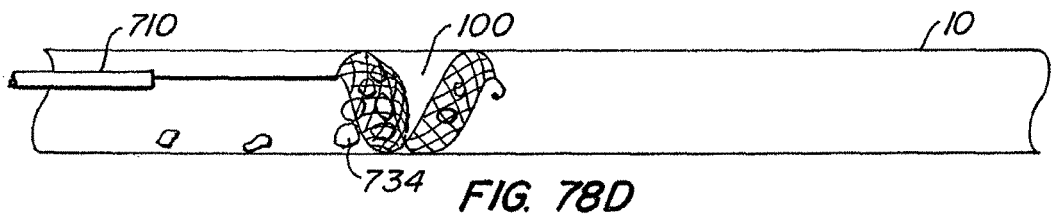
Figure 78E:
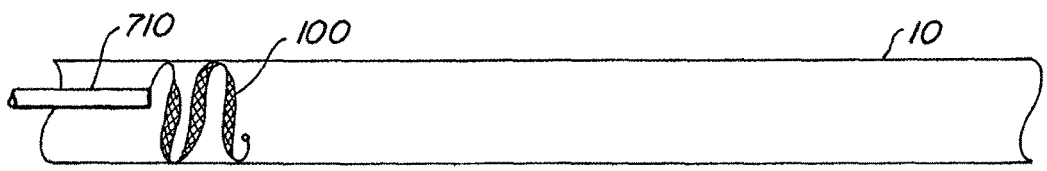
Figure 78F:
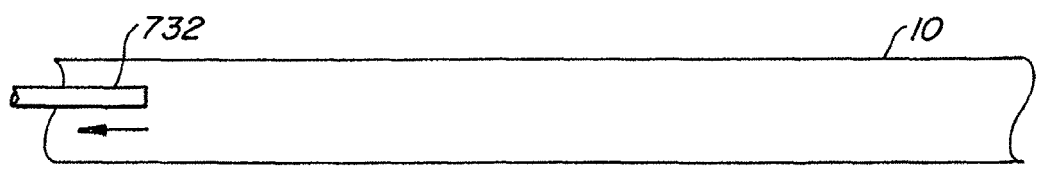

A tethered device (FIG. 77A, 78A) can also be employed to mechanically dislodge and remove embolic material 732 from a vessel 10, such as in the case of a thrombectomy. This offers a simple means of removing and trapping debris without requiring multiple devices to achieve the same goal. For this method, the tethered device is advanced downstream of the lesion site (FIG. 78A), and deployed (FIG. 78B). The tethered, deployed filter 100 is then drawn across the lesion 732 (FIG. 78C) to pull the thrombus from the vessel wall and into the filter 100 (FIG. 78D). The embolized material 734 is then removed via the methods previously described (FIG. 78E), tethered device is drawn into the sheath and removed from the lumen (FIG. 78F).

Delivery of Pharmacological Agents Using Filtering Devices

Embodiments of the filter device of the present invention may also be used for delivering a pharmacological agent within a lumen. Delivery of a pharmacological agent within a lumen may be accomplished using any component of the filtering device. For example, the filter support structure may deliver a pharmacological agent. In one alternative, the support structure is covered by a multi-lumen structure and the multi-lumen structure is configured to release a pharmacological agent. In one alternative, a lumen of the multi-lumen structure is at least partially filled with a pharmacological agent. In another aspect, a lumen in a multi-lumen structure has ports that allow for the release of a pharmacological agent stored within the lumen. In one alternative, a cavity formed in a support member is filled with a material. In one aspect, the material in the cavity is a pharmacological agent. The filter may deliver a pharmacological agent. In one aspect the material capture structure is coated with a pharmacological agent.

Figures 79, 80:
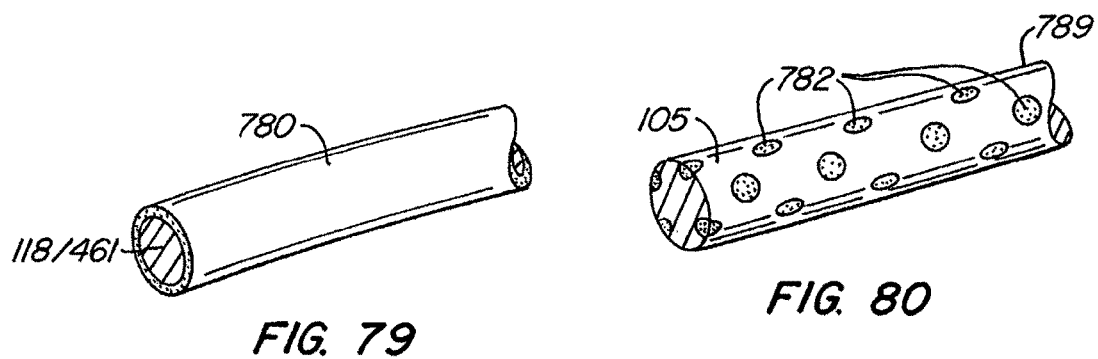
FIGS. 79-82 illustrate several alternative filtering device configurations adapted for the delivery of pharmacological agents.

Additional embodiments of the invention provide for the ability to deliver therapeutic agents via the material capture structure as well as the support structure covering. FIG. 79 illustrates a therapeutic agent coating 780 attached to a filament 118/461. FIG. 80 illustrates a composite structure 789 formed by having one or more cavities formed in a support structure 105 filled with one or more therapeutic agents or other material. The cavities may be formed as described above with regard to FIGS. 33, 35 and 36. These composite structures can be designed to elute a therapeutic agent via a specific elution curve by varying thickness, density as well as location of the therapeutic agent on the filter device component. This therapeutic agent could be, for example, any pharmacological agent used in the treatment of the body, an anti-coagulant coating (i.e., Heparin), an anti-proliferative agent prevent or slow fibrous tissue growth, other agents selected from those used in vascular stents including drug eluting stents.

Figure 81:
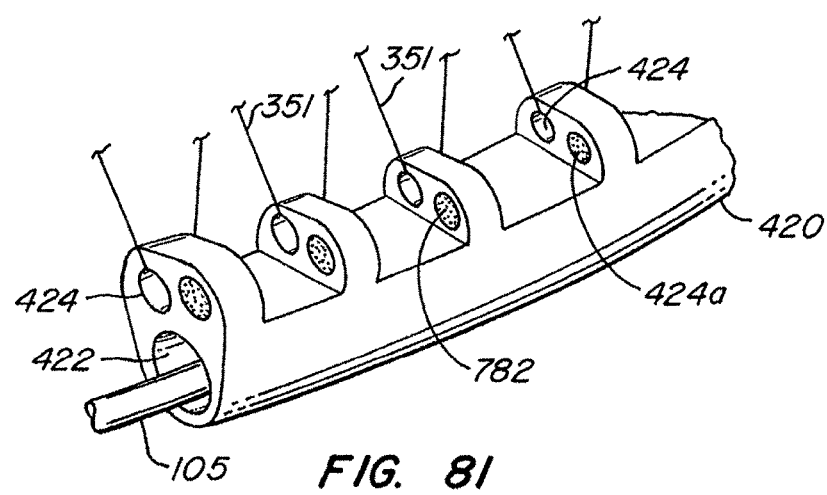
Figure 82:
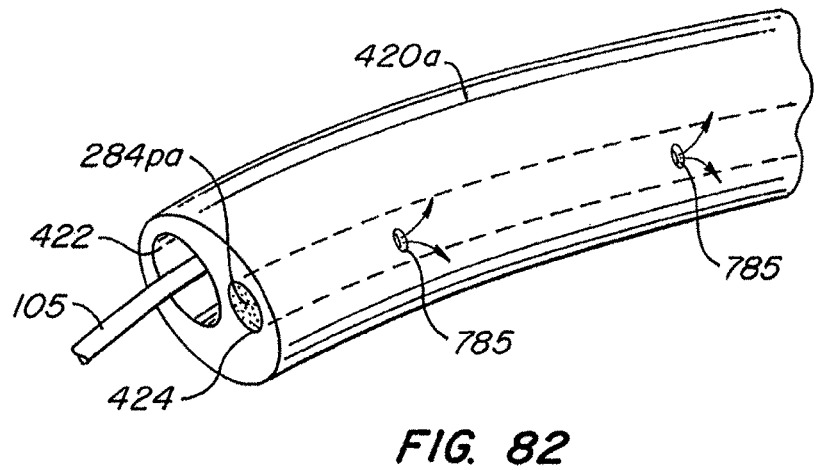
Figure 83A:
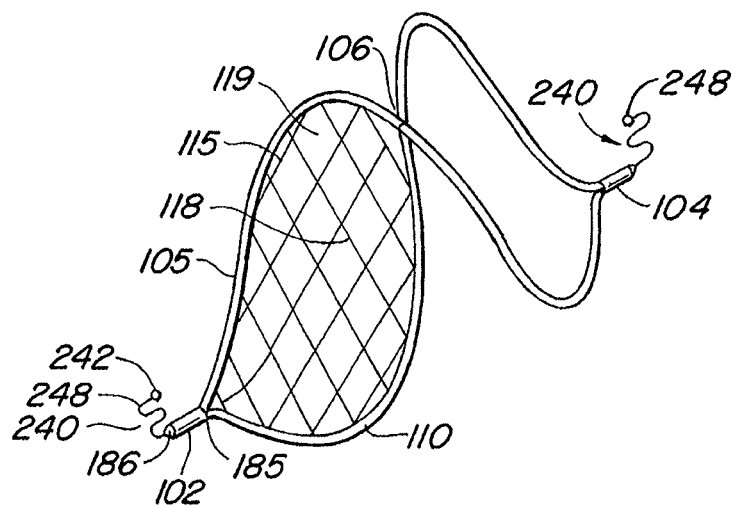
FIGS. 83A-87 illustrate several filtering device prototypes.
Figure 83B:
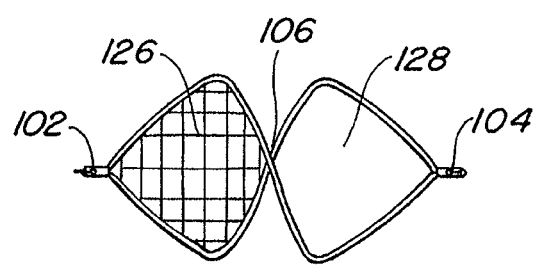
Figure 83C:
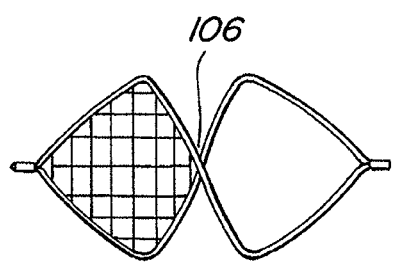
Figure 83D:
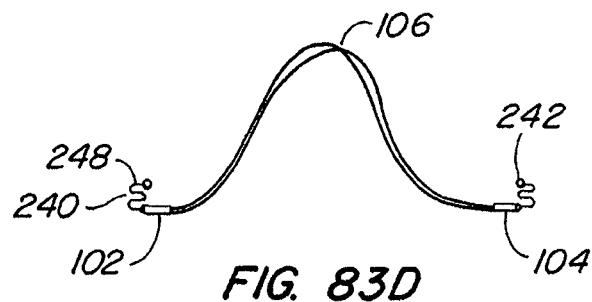
Figure 83E:
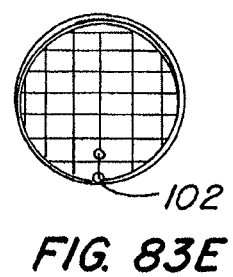
Figure 84A:
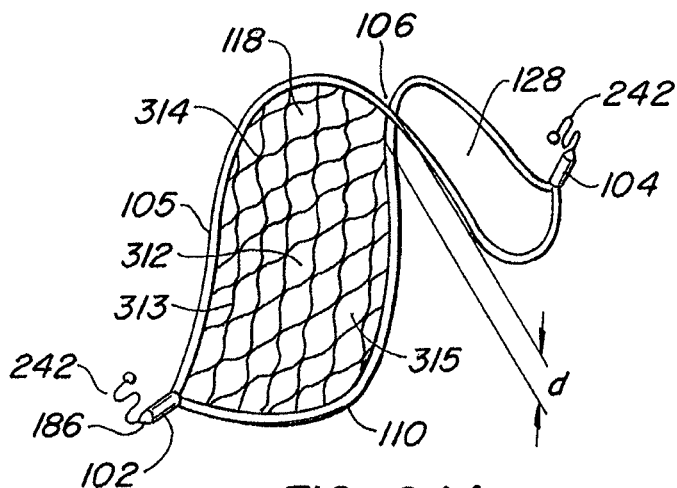
Figure 84B:
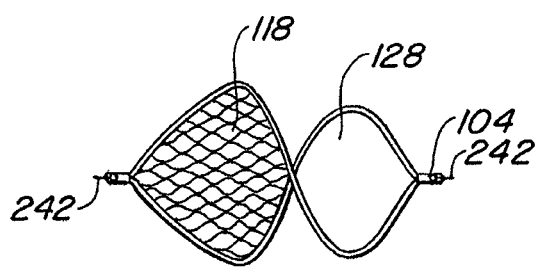
Figure 84C:
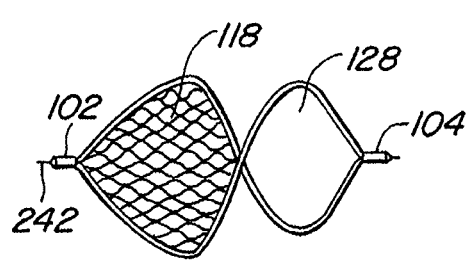
Figure 84D:
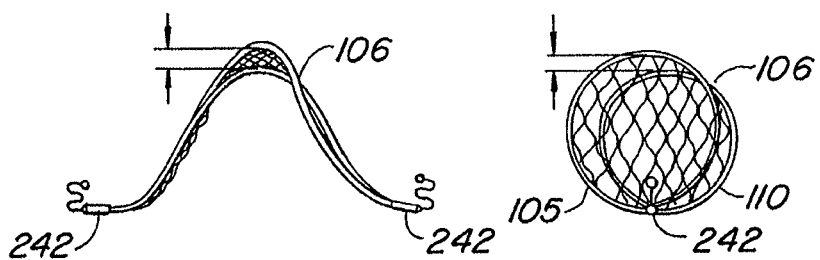
Figure 84E:
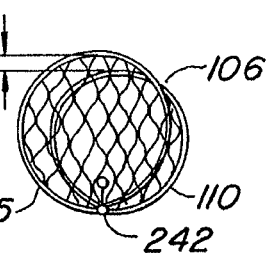
Figure 85A:
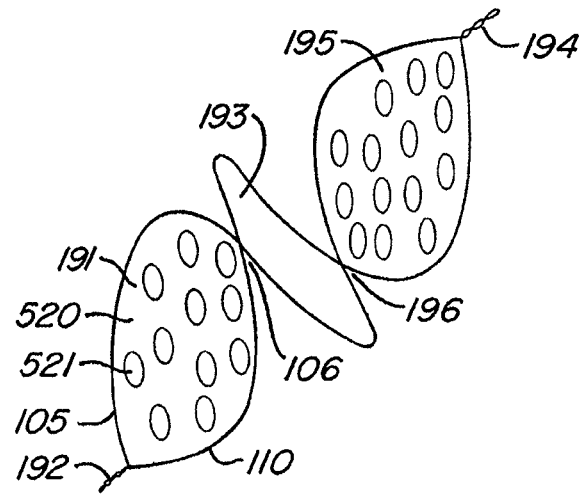
Figure 85B:
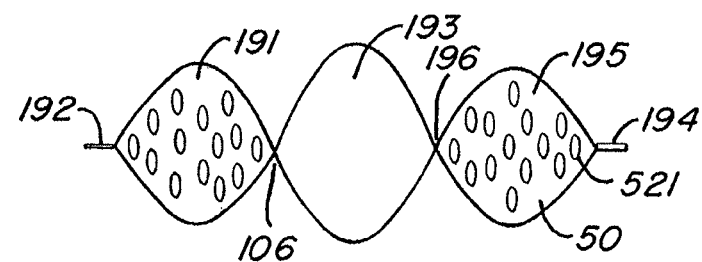
Figure 85C:
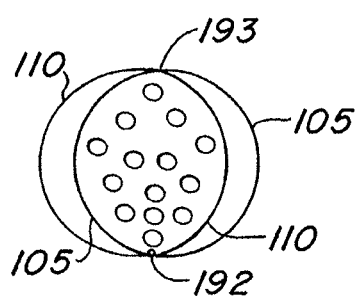
Figure 85D:
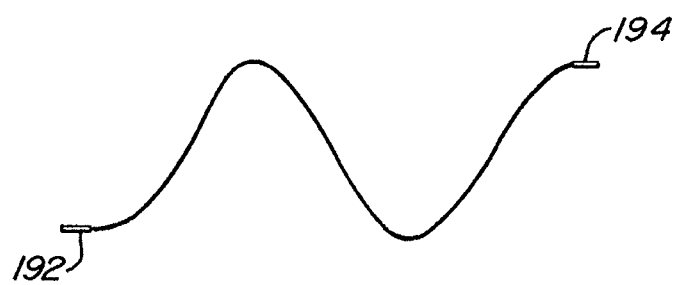
Figure 86A:
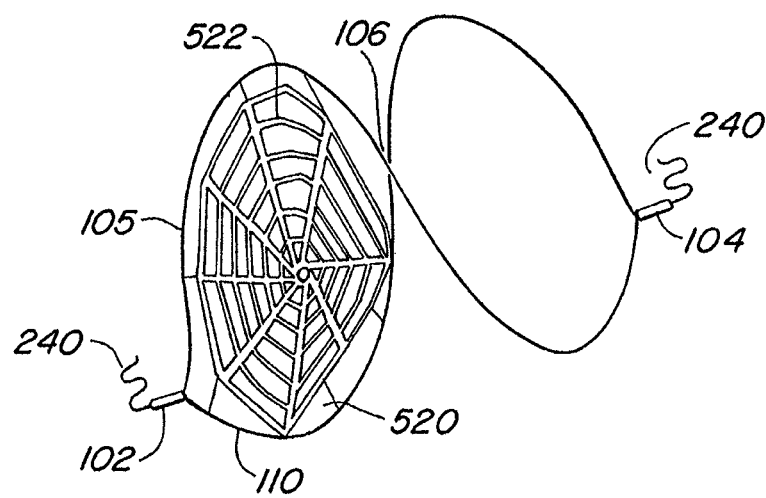
Figure 86B:
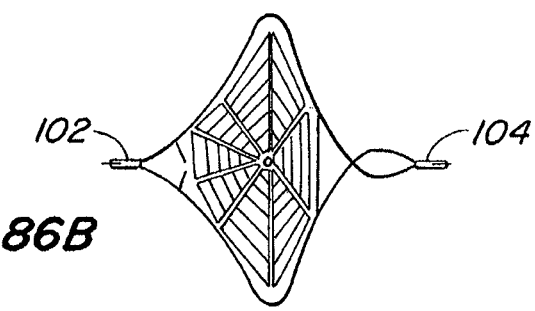
Figure 86C:
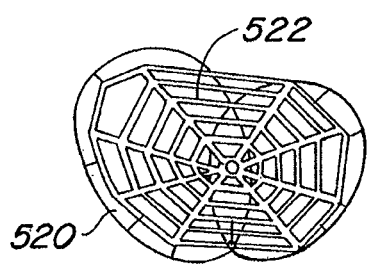
Figure 86D:
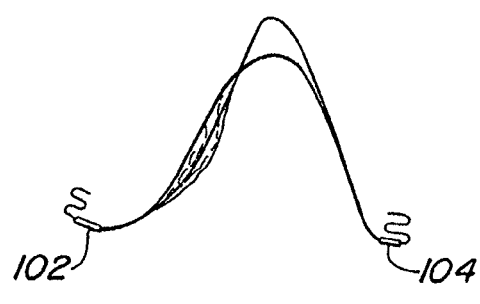

FIG. 81 and FIG. 82 illustrate the use of the covering 420, 420a positioned over a support structure as the delivery means for providing pharmacological agents into a lumen. FIG. 81 illustrates a pharmacological agent 782 in a lumen 424a of a multi-lumen structure such as described above with regard to FIGS. 44, 45. As illustrated in FIG. 82, the therapeutic agent 784 fills a lumen 424 in a multi-lumen covering 420a over the support structure 105. Release ports 785 formed in the side of lumen 424 allow delivery of the agent to the blood or tissue. Control of the therapeutic agent elution parameters could be controlled via the size or spacing of the release ports 785 and/or through the use of controlled release pharmacological agents.

Prototype Filtering Devices

FIGS. 83A-83E illustrate perspective (FIG. 83A), plan (FIG. 83B), bottom (FIG. 83C), side (FIG. 83D) and end (FIG. 83E) views of a prototype filter according to an embodiment of the present invention. The prototype has previously described features and common elements have the same reference numbers have been incorporated into these illustrations. The support structure 105, 110 was formed with electropolished 0.015" OD Nitinol wires, shape set to form two substantially equal open loops 126, 128 of approximately 1" diameter. The support structure wire used for support structure 105 was ground down to a wire diameter of 0.010" and used to form flexible retrieval feature 240 on each end (i.e., FIG. 28C). An atraumatic feature (here ball 242) is created on the end of the wire by exposing the wire to plasma. A radio opaque marker, here a Tantalum marker band 248 attached below the ball 242. The material capture structure 115 has filter cells 119 constructed with filaments 118. The filaments 118 are ePTFE monofilament. The filaments are attached to the support structure using method shown in FIG. 47. The cover 185 used to join the ends is a tapered Nitinol tube 186 that is crimped around the support structures, as illustrated in FIG. 24.

FIGS. 84A-84E illustrate perspective (FIG. 84A), plan (FIG. 84B), bottom (FIG. 84C), side (FIG. 84D) and end (FIG. 84E) views of a prototype filter according to an embodiment of the present invention. This embodiment is similar to the embodiment of FIG. 83A. In this embodiment, the material capture structure 115 is replaced with material capture structure 312 made of an extruded polymeric netting as described above with regard to FIG. 56. This embodiment also illustrates how the support structures 105, 110 are not in contact (i.e., separated by a distance "d") at the crossover 106.

FIGS. 85A-85E illustrate perspective (FIG. 85A), plan (FIG. 85B), side (FIG. 85D) and end (FIG. 85C) views of a prototype filter according to an embodiment of the present invention. This embodiment is similar to the filter device described in FIG. 14A and common reference numbers are used. In this embodiment, a material capture structure is constructed from a continuous sheet of polymeric material 520 into which circular holes 521 are created via mechanical or laser cutting (as described above with regard to FIG. 61A).

FIGS. 86A-86D illustrate perspective (FIG. 86A), plan (FIG. 86B), side (FIG. 86D) and end (FIG. 85C) views of a prototype filter according to another embodiment of the present invention. In this prototype filter, a material capture structure constructed from a continuous sheet of polymeric material 520 into which a pattern 522 voids are created via mechanical or laser cutting to create a net-like structure (FIG. 61C).

Figure 87:
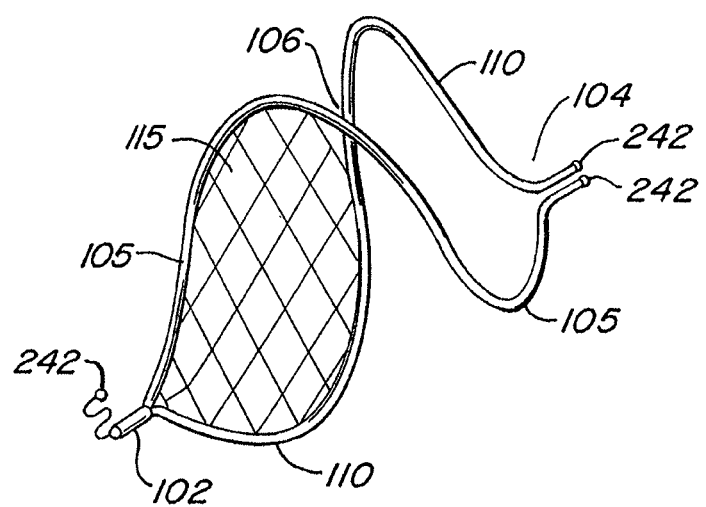

FIG. 87 is a perspective view of a prototype filter according to an embodiment of the present invention similar to the embodiment described in FIGS. 83A-83E above. In this embodiment the elongate structural members 105, 110 are joined at only one end (i.e., end 102). The support structure elements on the unconnected end are finished with plasma balls 242 to prevent vessel perforation and facilitate deployment and retrieval.

Figure 88:
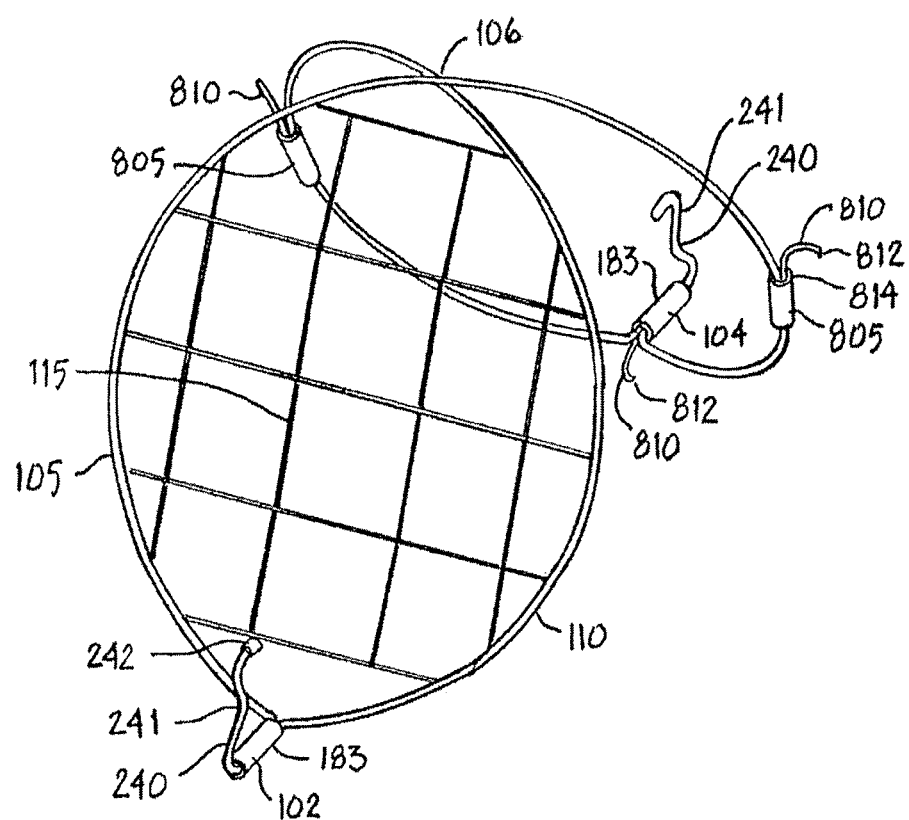
FIG. 88 is a perspective view of an endoluminal filter having three tissue anchors.
Figure 91:
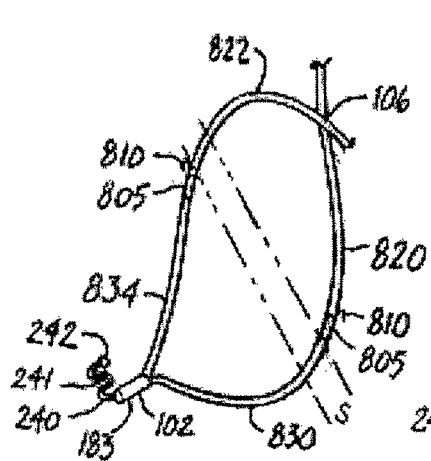
FIG. 91 is a perspective view of a filter device performed by joining the device illustrated in FIG. 90A with the device illustrated in FIG. 90B.
Figure 99:
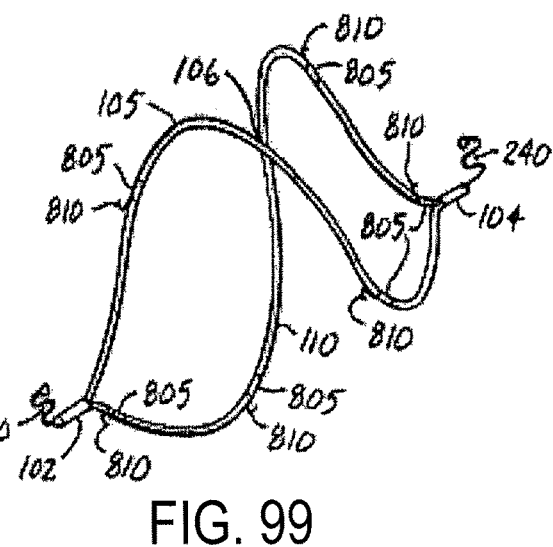
FIG. 99 illustrates a support frame without a material capture structure showing the placement and orientation of various fixation elements.

Some filter embodiments may include one or more fixation elements, tissue anchors or tissue engagement structures to aid in maintaining the position of the filter once deployed. The various alternative fixation elements, tissue anchors or tissue engagement structures are described below and may be adapted into a variety of combinations and configurations. FIG. 88 is a perspective view of an endoluminal filter having a first support member 105 having a first end and a second end and a second support member 110 attached to the first end of the first support member 105 or the second end of the first support member 105. In the illustrated embodiment, the first support member 105 and the second support member 110 are each formed from a single wire that extends from at least the first end 102 to the second end 104. The support members may extend beyond the end 102, 104 and be used to form retrieval features 240 or other elements of the filter as described below. In one illustrative example, the first support member 105 may be formed into a tissue anchor and the second support member 105 may be formed into a retrieval feature. The illustrative embodiment has a retrieval feature 240 on the first end 102 and a retrieval feature 240 on the second end 104. The second support member 110 forms a crossover 106 with the first support member 105. In one embodiment, the second support member 110 is attached to the first end of the first support member 102 and the second end of the first support member 104. A material capture structure 115 extends between the first and second support members 105, 110, the crossover 106 the first end or the second end of the first support member 105. In the illustrated embodiment, the material capture structure extends between the first and second support structures 105, 110, the first end 102 and the cross over 106. At least one tissue anchor 810 is on the first support member 105 or the second support member 110. In the illustrated embodiment, tissue anchors are provided on body supports 105, 110. In this embodiment, the fixation element 810 is a separate structure having a body 814 and a tip 812 suited for penetrating into or through the walls of lumen 10. The fixation element or tissue anchor 810 is attached to the elongate body using a suitable attachment 805. The attachment 805 may be a crimp (as illustrated) or any other suitable technique for joining the fixation element 810 to the elongate body. Suitable techniques include, by way of non-limiting example, a crimp or other joining technique with a discrete detent, a swage or other joining technique with circumferential constriction, soldering, welding, brazing, shrink fit tubing, epoxy, multi-lumen collar where one wire is placed in each lumen and then bonded or melted together. FIGS. 91 and 99 also illustrate possible configurations for filter structures formed from two elongate support members that are joined at the ends.

Figure 89A:
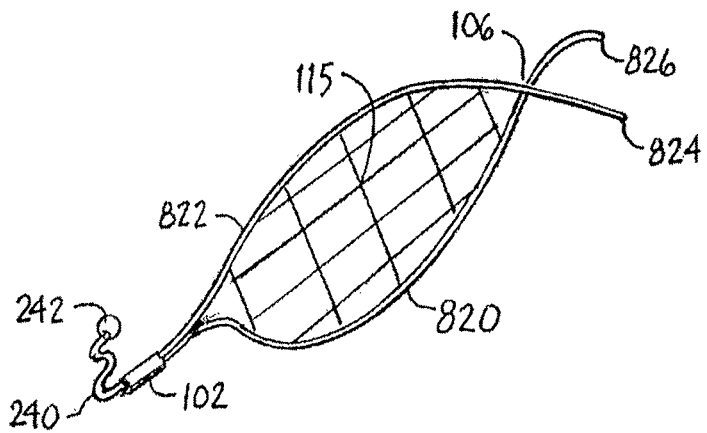
FIGS. 89A and 89B illustrate individual filter components that may be assembled into the final version illustrated in FIG. 89C.
Figure 89B:
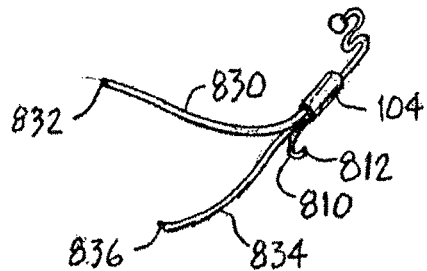
Figure 89C:
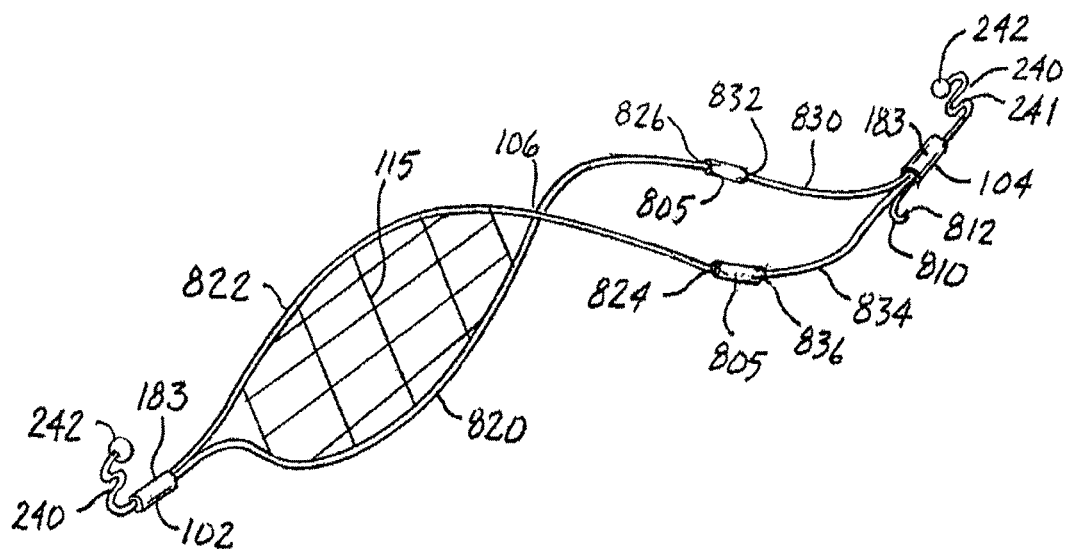
FIG. 89C is a perspective view of a final assembled filter.

FIGS. 89A and 89B illustrate individual filter components that may be assembled into the final version illustrated in FIG. 89C. FIG. 89A illustrates the proximal end of the filter. The elongate bodies 820, 822 are used to secure a filter structure 115 between a cross over 106 and the end 102. The elongate bodies 820, 822 extend some length beyond the crossover 106 to ends 826, 824. A retrieval feature 240 is attached to end 240 and may be formed, in one exemplary embodiment; from either elongate body 820, 822. FIG. 89B illustrates the distal end of the filter. The distal end of the filter is formed by elongate bodies 834, 830 joined by end 104. The length of elongate bodies 830, 834 may be adjusted to join with the elongate bodies 820, 822 in FIG. 89A to form an appropriately sized filter. The distal end also includes a retrieval feature 240 and a fixation element 810. The final assembled filter is illustrated in FIG. 89C where the proximal and distal filter ends are joined at suitable joining connectors 805. It is believed that the manufacturing procedure used for constructing a filter is simplified through the use of proximal and distal ends. Each of the ends may be fabricated separately in relatively fewer and easier steps than when fabricating a filter from two elongate bodies of nearly equal length as described elsewhere in this application. Additionally, suitable joining connectors 805 used to couple the proximal and distal ends may also be used to attach a fixation element to the filter frame as illustrated, for example, in FIG. 91, 95 or 99.

Figure 90A:
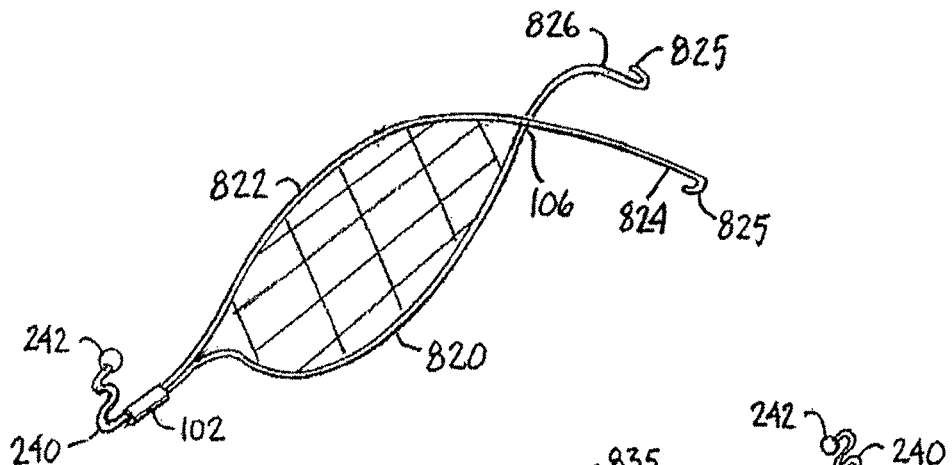
FIGS. 90A and 90B illustrate proximal and distal filter ends with the tips of the elongated members modified to form fixation elements.
Figure 90B:
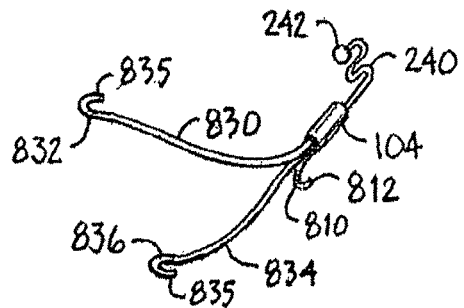

Alternatively, the ends of the elongate bodies could be used to form the fixation elements. FIGS. 90A and 90B illustrate proximal and distal filter ends with the tips of the elongate members modified to form fixation elements. The proximal filter end embodiment illustrated in FIG. 90A has hooks 825 formed on ends 824, 826. The distal filter end embodiment illustrated in FIG. 90B has hooks 835 formed on ends 832, 836.

Figure 90C:
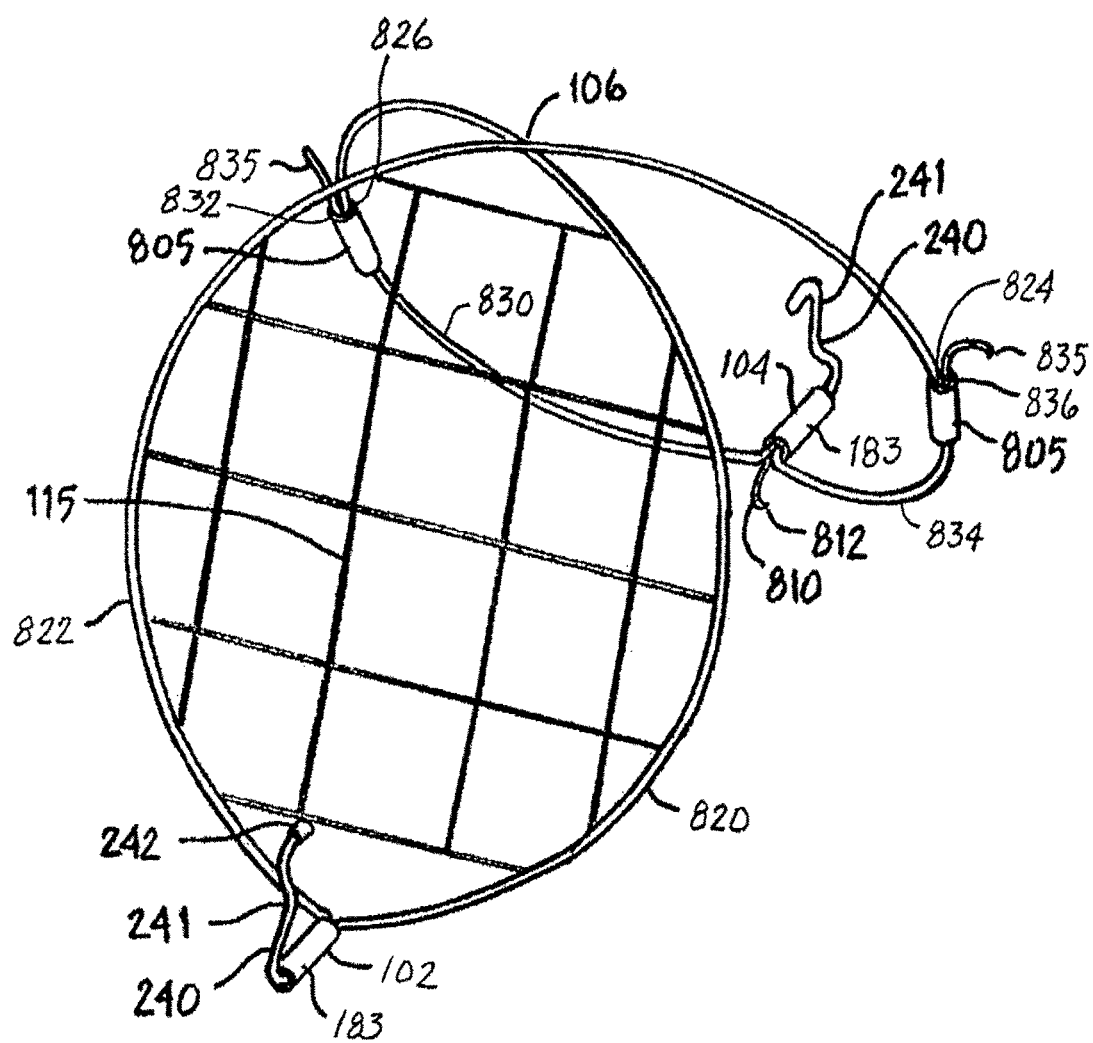
FIG. 90C is a perspective view of a filter assembly using the proximal distal end of FIGS. 90A and 90B.

FIGS. 90A and 90B may be combined using a suitable joining connector(s) 805 to form a double hook fixation element such as illustrated in FIGS. 95, 104A, 104B, and 104C. Alternatively, the modified distal and proximal ends in FIGS. 90A and 90B may be combined in any combination to the unmodified distal and proximal filter ends illustrated in FIGS. 89A and 89B. FIG. 90C illustrates an embodiment of one combination that joins the proximal end in FIG. 89A with the distal end in FIG. 90B. Other combinations are possible. For example, the tissue anchor is on the first or the second attachment means. Additionally or alternatively, there can be a retrieval feature on the end of the first support structure and a retrieval feature on the end of the second support structure.

These, along with other embodiments, illustrate a filter support structure having a first support member having an end, a first segment extending from the end and a second segment extending from the end. There is also a second support member having an end and a first segment extending from the end and a second segment extending from the end and crossing but not attaching to the first segment. There is a first attachment means for joining the first segment of the first support member to the first segment of the second support member and a second attachment means for joining the second segment of the first support member to the second segment of the second support member. A tissue anchor is provided on or with the first or the second support member. As described in further detail above, there is also a material capture structure attached to the first and second segments of the second support member and between the end of the second support member and the place where the first segment crosses the second segment.

Additionally, while FIGS. 89A-90B illustrate elongate body components having the same or nearly the same length, the design is not so limited. The use of elongate bodies of different length can be used to position the fixation elements in off set locations along the elongate body. The elongate body lengths 820, 822, 830, 834 may be of different lengths than in previous examples attached as shown in FIG. 91. The use of different elongate body lengths produces a spacing (indicated by "s" in the figure) between the attachments 805. The dashed lines indicate the position of each fixation element when the fixation elements are moved into a stowed condition. The offset spacing "s" reduces the likelihood that the fixation element 810 between elongate bodies 820, 830 will become entangled with the fixation element 810 between elongate bodies 822, 834 when the filter is stowed prior to delivery (see FIG. 123B). Alternatively or additionally, the offset spacing "s" may be achieved by placing fixation elements on the elongate bodies in positions that result in the desired amount of offset to prevent the fixation elements from getting tangled.

Figure 93A:
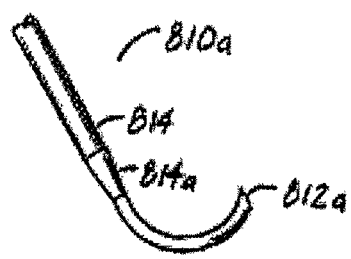
FIGS. 93A and 93B are perspective and cross section views respectively of a prior art fixation element having a transition section and a reduced diameter section.
Figure 93B:
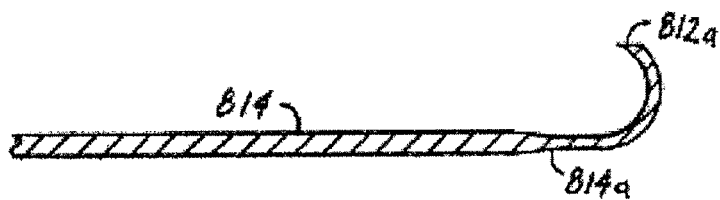
Figure 92:
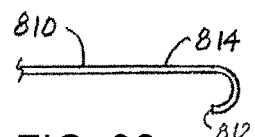
FIG. 92 illustrates a fixation element formed in the end of an elongate body.

There are a number of various fixation elements that may be used. The fixation elements 810 shown in FIG. 92 illustrates a fixation elements that may be formed on the ends of the elongate bodies (i.e., FIGS. 90A and 90B) using a number of bending and forming techniques. The end may remain at the same diameter as the rest of the elongate body as shown in FIG. 92. The end is shaped into the desired curve between the body 814 and the tip 812 for engagement with the surrounding lumen. In one alternative embodiment, the elongate body end is cut, ground or otherwise shaped into a sharpened point or beveled tip 812. Additionally or alternatively, the fixation element may have a smaller diameter than the remainder of the elongate body as illustrated in FIGS. 93A and 93B. Fixation element 810a has an elongate body diameter that is reduced in a transition section 814a down to the desired final diameter of the tip 812a. The now reduced diameter end is then shaped into the desired curvature depending upon how the fixation element is to engage with the surrounding tissue. In an alternative embodiment, the transition section 814a alone or in combination with the tip 812a may be formed from a different material that the body 814. The difference in the materials or different qualities of the same material may be used to provide a barb or tissue anchor with a flexible tip. For example, either or both the transition 814a and the tip 812a may be formed from a flexible biocompatible material such as polytetrafluoroethylene (ePTFE), polytetrafluoroethylene (PTFE), Poly(ethylene terephthalate) (PET), Polyvinylidene fluoride (PVDF), tetrafluoroethylene-co-hexafluoropropylene (FEP), or poly (fluoroalkoxy) (PFA), other suitable medical grade polymers, other biocompatible polymers and the like.

Figure 94:
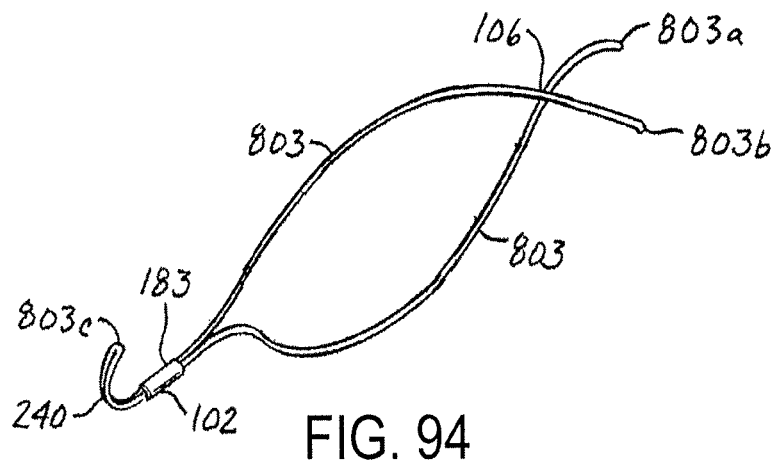
FIG. 94 illustrates an embodiment of a filter structure proximal end formed from a single wire.
Figure 95:
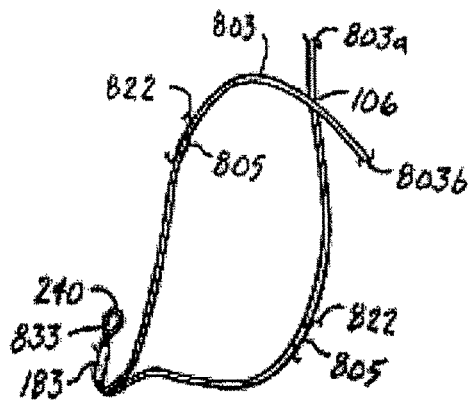
FIG. 95 illustrates an embodiment of a filter structure proximal end formed from a single wire with fixation elements from FIG. 104A.
Figure 104A:
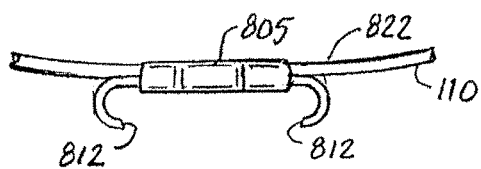
FIGS. 104A and 104B illustrate a double ended fixation element (FIG. 104A) and attachment of a double ended fixation element to an elongate body (FIG. 104B)
Figure 104B:
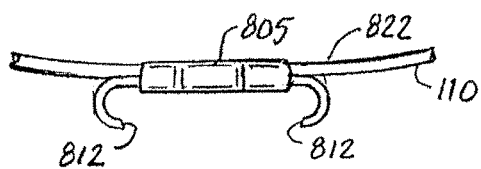

FIG. 94 illustrates an embodiment of a proximal end 102 of a filter structure that is formed from a single wire 803. The wire 803 begins at the end 803a is curved into one side of the support frame and then into the retrieval feature 240. The wire 803 is reversed 803c to form the other side of the retrieval feature 240 and then the other side of the support frame to the end 803b. A crimp 183 or other suitable fastener is used to maintain the shape and position of the retrieval feature 240. While this illustrative embodiment describes a single wire formation technique for a proximal end 102, this technique may also be applied to the formation of a distal end 104. The retrieval feature 240 may also take shapes other than the one in the illustrated embodiment and may, for example, be formed to resemble retrieval features illustrated in FIGS. 20-22 and 25-28C. As shown in FIG. 95, the single wire 803 may also used to form a loop 833 on the distal end 240. This illustrates a technique for forming both the first support member and the second support member from a single wire. This embodiment also shows the connector 183 in a position raised above the lumen wall. Additionally, a double ended fixation element 822 is shown. This is an example of a tissue anchor having a first barb with a proximal opening and a second barb with a distal opening. The double ended fixation element may be formed by curving the ends of proximal and distal ends (see FIGS. 90A, 90B). Alternatively as shown in FIG. 104A, the fixation element 822 may be a stand alone component with a body 814 curved into two tips 812. As shown in FIG. 104B, the fixation element 822 may be joined to any elongate body using a suitable fixation 805. In the illustrated embodiment, the fixation element 822 is attached to an elongate body 110. The ends 812 may also be curved in different directions or different angles as shown in FIG. 104C.

Any of a wide variety of bonding or joining techniques may be used to join the proximal and distal ends such as: soldering, welding, brazing, shrink fit tubing, epoxy, multi-lumen collar where one wire is placed in each lumen and then bonded or melted together, twisting wires together. Alternatively, one or more techniques could be used to join the elongate bodies with or without the addition of a fixation element. Then, in order to reduce surface defects to initiate tissue growth, the area where the joining occurred is covered by a smooth material. The joined area could be coated with an epoxy or medical grade silicone, or a shrink fit tube or slotted tube could be placed over the join and then melted into place. Consider FIGS. 89A and 89B in an illustrative example of an alternative technique to provide a smooth surface to a joined area. First, a segment of heat shrink tubing is sufficiently long to cover the length of the elongate body included in the joining process is placed on the elongate bodies 830, 834 over the ends 832, 836, respectively, of FIG. 89B. Next, the ends 832, 836 in FIG. 89B are joined to the ends 824, 826 in FIG. 89A. Thereafter, the heat shrink tubing segments are advanced over the joined area and heated. As the heat shrink tubing segment is heated, it melts around the joined area and provides a smooth surface that seals the area where the end 826 joins end 832 and end 824 joins end 836.

The joint 805 is an example of an attachment element that joins the first support member to the second support member. The joint 805 could be used to join elongate bodies together as suggested by the embodiments illustrated in FIGS. 88, 89A, 89B, 90A, 90B, 94 and 96. Alternatively, the joint could be used to secure a fixation element to the filter frame. In yet another alternative, the joint could provide means for both joining the elongate bodies together into a single frame as well as joining a fixation element to the filter frame at the same point that the elongate bodies are joined. Suitable means for attachment and attachment techniques used to create the joint 805 include, by way of non-limiting examples, a crimp or other joining technique with a discrete detent, a swage or other joining technique with circumferential constriction, soldering, welding, brazing, shrink fit tubing, epoxy, multi-lumen collar where one wire is placed in each lumen and then bonded or melted together.

The material capture structure 115 may be in any of a number of different positions and orientations. FIG. 96 illustrates an embodiment of a filter of the present invention having two open loop support frames formed by support members 105, 110. Flow within the lumen 10 is indicated by the arrow. In this embodiment, the material capture structure 115 is placed in the upstream open loop support structure. In contrast, the material capture structure may be positioned in the downstream open loop support structure (FIG. 97). In another alternative configuration, both the upstream and the downstream support frames contain material capture structures 115.

There are filter device embodiments having equal numbers of support frames with capture structures as support frames without capture structures (e.g., FIGS. 13A, 13B, 97A, and 97B). There are other embodiments having more support frames without capture structures than there are support frames with capture structures. For example FIG. 14 illustrates a filter embodiment 190 having more support frames without capture structures than support frames with captures structures. The filter device 190 has two support members 105, 110 that are positioned adjacent to one another to form a plurality of support frames that are presented to the flow within the lumen 10. These support frames could also be modified to include fixation elements in any combination or configuration described herein. Alternatively, the plurality of support frames positioned to support a material capture structure across the flow axis of the device 190 or the lumen 10. The support members are joined together at end 192 and have two inflection points before being joined at end 194. The support members 105, 110 cross over one another at crossovers 106 and 196. The support frame 191 is between end 192 and crossover 106. The support frame 193 is between the crossovers 106, 196. The support frame 195 is between the cross over 196 and the end 194. One or more fixation elements may be provided in any or all of the support frames 191, 193 and 195 as described herein.

FIG. 98 illustrates a fixation element 810 engaged within the side wall of lumen 10. In this embodiment, the length and curvature of the fixation element is selected to remain within the wall of the lumen 10. As shown, the tip 812 is within the sidewall of lumen 10. In other alternative configurations, the length and curvature of a fixation element is selected engage with the lumen 10 by piercing though the lumen wall.

Figure 100:
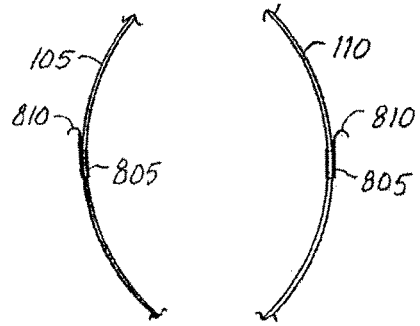
FIG. 100 illustrates the placement of the fixation elements about mid-distance between the ends and the crossover.
Figure 101:
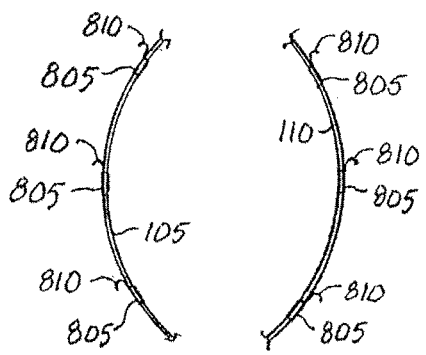
FIG. 101 illustrates the placement of fixation elements similar to FIG. 100 with additional of fixation elements positioned near the crossover and the ends.
Figure 102:
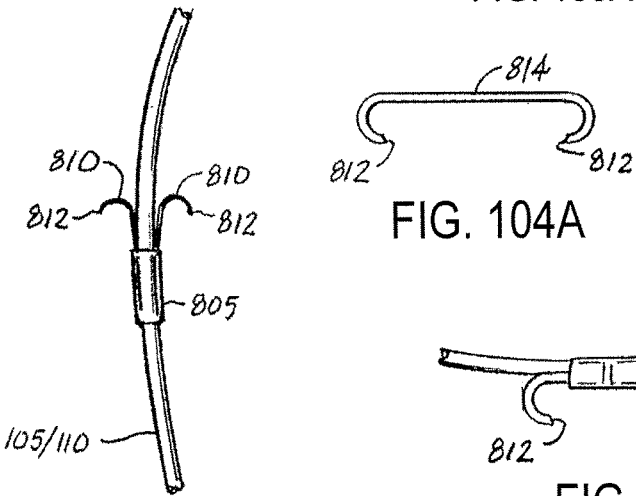
FIG. 102 illustrates more than one fixation element positioned at the same location along the filtering device.

The fixation element could be a separate element or formed from one of the elongate bodies. Additionally, fixation elements may be positioned in any of a number of different positions and orientations. FIG. 88 illustrates fixation elements positioned about half way between an end 102, 104 and the cross over 106. An additional fixation element is positioned on the end 104. Unlike the illustrative embodiment of FIG. 88 where the fixation elements are on a single support frame, FIG. 99 illustrates the location of additional fixation elements on both support frames as well as the ends 104, 102. FIG. 99 does not illustrate any material capture structure within the frame. In FIG. 99, the fixation elements 810 are positioned along both elongate bodies 105, 110 about mid-way up on the support frame between an end and the crossover. Alternative fixation element 810 spacing and orientation is illustrated in FIGS. 100 and 101. FIG. 100 illustrates placement of the fixation elements 810 about mid-distance between the ends 102, 104 and the cross over 106. FIG. 101 illustrates the placement of the fixation elements similar to FIG. 100 with additional elements positioned near the cross over 106 and an end 104, 104. As illustrated in FIG. 102, more than one fixation element or barb may be positioned at each location along the structure. FIG. 102 illustrates a fixation attachment point 805 that secures two fixation elements 810 to the elongate body 105, 110. The fixation elements 810 may be provided separately or, alternatively, one or both of the fixation elements 810 may be formed from the elongate bodies. More than one barb or fixation element on a single location along the filter structure is also illustrated in FIGS. 95, 104A, 104B and 104C, for example.

Figures 103A, 103B, 103C:
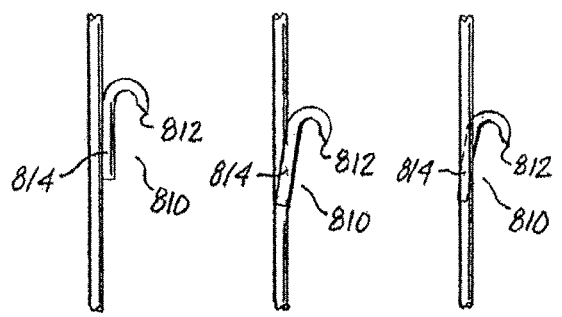
FIGS. 103A, 103B and 103C illustrate positioning of a fixation element on the elongate body (FIG. 103A) or to one side of the elongate body (FIGS. 103B and 103C)

Returning to FIG. 88, attachment portion 805 could also be used to mount or secure an individual fixation element 810 to an elongate body. FIGS. 103A, 103B and 103C for individual elements may be attached on (FIG. 103A) or on the sides (103A, 103B) to provide the desired orientation to the lumen wall as well as provide the desired device profile. Cover or joining structure 805 used to secure the fixation element to the elongate body has been removed to show detail.

Fixation elements may be designed to engage, pierce or otherwise attach to the lumen sidewall with more than one attachment point. FIG. 102 illustrates more than one fixation element 810 attached to an elongate body at a single attachment site or with a single cover or joint structure 805. FIG. 104A illustrates a double ended fixation element 822 having a body 814 with two fixation tips 812. FIG. 104B illustrates the double ended fixation element 822 attached to an elongate body 110. FIG. 104C illustrates how the tips 812 may be altered to adjust the manner by which the tips engage with the adjacent lumen wall. FIG. 104C illustrates one proximally opening tip 812 and one distal opening tip 812.

Different fixation element body orientation and fixation positions for the tips 812 are possible. In one embodiment, the tissue anchor comprises a coil wrapped around the first support member or the second support member and an end raised above the first support member or the second support member. An illustrative example of one such tissue engagement or anchor is illustrated in FIG. 105. FIG. 105 illustrates a curved wire 817 extending along and wrapped around the elongate body and then curling to place a curl between the fixation portion 105 and the tip 812. The degree of curvature of the curved wire 817 may be adjusted to control the force used to pierce the tissue or control the amount of fixation force applied to the lumen walls. Alternatively, as illustrated in FIG. 106, the fixation element body 817 may attach to the elongate body 110 by wrapping around a length of the elongate body. FIG. 105 also illustrates an example where the tissue anchor is a coil or open tube having a tissue engagement surface comprising a raised spiral form. FIG. 105 also illustrates a tissue anchor having an attachment section attached to the first support member or the second support member, an end adapted to pierce tissue and a coil 817 between the attachment section and the end 812. An optional covering (not shown) may also be placed over the coiled wire 817 to maintain a smooth device profile along the elongate body 110.

The filter structure may also be secured using alternative fixation elements illustrated in FIGS. 107A, 107B. In some embodiments, a tissue anchor or anchors are formed from or attached to a tube that is attached to the first support member or the second support member. FIGS. 107A and 107B illustrate a tube or support 821 adapted to fit over the elongate body 110. A feature 823 on the support 821 is used to engage with sidewall of the lumen. In the illustrated embodiment of FIG. 107A, the feature has a generally conical shape with a pointed tip, similar to a thorn. One of more of the supports 821 may be placed along the elongate body 810 as illustrated in FIG. 107B. Alternatively, the feature 823 may be formed from or as part of an integrated structure with the support 821. The feature 823 may be formed in a different shape than illustrated. The feature 823 may take the form of a circumferential rib, or a void/dentent. In another alternative embodiment, the support 821 is a continuous piece that extends along the length or most of the length of the elongate body 110 rather than in discrete segments 821 illustrated in FIG. 107B. In one embodiment the segment and features are formed from (Eric—please provide materials to make the segment and features from). The size, number and spacing of the feature 823 or features 823 may vary depending on application. For anchoring a material capture structure in the inferior vena cava, for example, a feature 823 may have a height of between about 0.5 mm to about 3 mm have spacing of about 0.1 mm to about 5 mm.

FIGS. 108 and 109 illustrate another alternative fixation element. In these alternative embodiments, a tissue anchor is formed from the first support member or the second support member (FIG. 109) or is attached to or formed from a structure or tube that is attached to the first support member or the second support member (FIG. 108). Additionally or alternatively, a tissue anchor can be formed from or attached to a tube that is attached to the first support member or the second support member. FIG. 108 illustrates a tissue anchor that is a tube 843 having a tissue engagement surface. In this illustrative embodiment, the tissue engagement surface includes triangular fixation elements 847. The triangular fixation elements 847 may be formed in the sidewall of a hollow tube 843 as shown in FIG. 108. Then, the hollow tube 843 is then placed over and secured to the elongate body 110. Suitable materials for tube 843 include, for example: Nitinol, stainless steel or previously described polymers and degradeable polymers. The cross section of the hollow tube 843 is illustrated as round but other cross sections are possible. In one embodiment, the cross section of the tube 843 is sized and shaped to conform to the size and cross section shape of the elongate body 110. Alternatively, instead of forming the triangular fixation element(s) 847 in a tube that is placed over the elongate body, the triangular fixation members 847 are formed in or using the surface of the elongate body 110 as shown in FIG. 109. In this illustrative embodiment, the tissue anchor(s) on the first or the second support member are formed from the first or the second support member. While the illustrated embodiments show fixation elements 847 having a generally triangular shape other shapes are possible. For example, the fixation elements 847 may be shaped as an elongate spike or in any other suitable shape for engaging the adjacent lumen or tissue.

Figure 110:
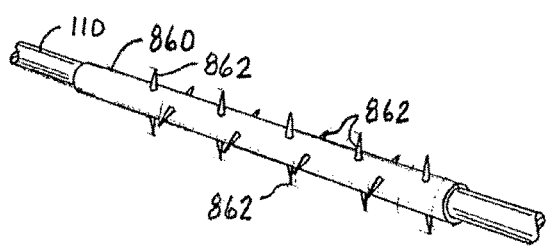
FIG. 110 illustrates a perspective view of tube with a surface modified to provide tissue engagement features.
Figures 111A, 111B:
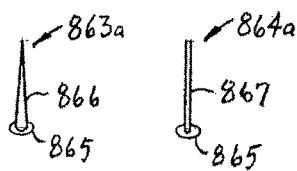
FIGS. 111A and 111B illustrate alternative fixation features that may be mounted on, in or through the wall of a tube.

In another alternative embodiment illustrated in FIG. 110, the tube 847 may be modified to form a tissue engagement surface. In this illustrative embodiment, the tissue engagement surface includes surface features 862 that are shaped like spikes or thorns. One method of making the features 862 is to heat a polymer tube until the surface of the tube becomes tacky. Next, the surface of the tube is wicked up into the shape of the feature 862. As illustrated, the tube 860 is segmented to cover only a portion of the elongate body 110. In another embodiment, the tube is the same length or about the same length as the elongate body 110. Instead of modifying the surface of the tube 860, tissue engagement features 862 may instead be formed by mounting a fixation feature on, in or through the wall of the tube 860. A tissue engagement feature may take any of a number of different shapes as illustrated in FIGS. 111A and 111B. FIG. 111A illustrates a tissue engagement feature 863a with a base 865 supporting a sloped body 866 that ends in a pointed tip. FIG. 111B illustrates a tissue engagement feature 864a with a base 865 supporting a generally cylindrical body 867 that ends in a flat tip. The tissue engagement features may be added to the tube 860 by pushing them through the sidewall such that, when installed, the base 865 is within the lumen of the tube 860 and the body 866, 867 extends through the sidewall as shown in FIG. 110.

Figure 112:
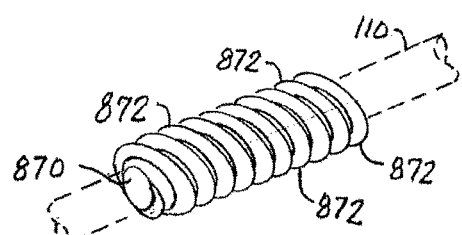
FIG. 112 is a perspective view of a tube based fixation element having a raised spiral form.

FIG. 112 includes another alternative embodiment of a tube based fixation element. In this embodiment, the tissue engagement surface comprises a raised form. In one embodiment, the tissue anchor is a tube having a tissue engagement surface comprising a raised spiral form. As shown in FIG. 112, the surface of the tube 870 has been modified into a raised spiral with ridges 872. The raised spiral 872 may be in a segment as shown. One or a plurality of segments may be attached along the length of the elongate body. Alternatively, instead of a segment, the tube 870 may be the same length as or about the same length as the elongate body 110 to which it is attached. In another alternative embodiment, the raised portion is formed by inserting a spring or other structure beneath the surface of the tube or segment 860. Additionally or alternatively, the tissue anchor comprises a coil wrapped around the first or the second support member. As illustrated in FIG. 106, this alternative can be formed by wrapping one wire (the elongate body 110) with another wire or a spring (wrapped wire 817). The wire 110 and wrapped wire 817 may then be coated by another material or placed into a suitable shrink tubing. Once the material or heat shrink is treated to conform to the wires, the resulting structure would resemble that shown in FIG. 112 with the addition that the tips 812 (see FIG. 106) would extend through the material to provide an additional attachment point to the lumen.

It is to be appreciated that the formation of tissue engagement structures may take any of a number of alternative forms alone or in any combination. As shown and described above in FIG. 109 features 847 may be cut into the surface of a elongate body. FIG. 108 illustrates how similar features may be cut into the walls of a tube 843. Additionally, the tissue engagement surface may take the form of a raised profile surface on the tube as shown in FIGS. 106, 112. Additionally or alternatively, the tissue engagement surface may be formed by roughening the surface of the tube or structure that engages the tissue, thereby increasing the coefficient of friction between the filter and the tissue it contacts. In some embodiments, the roughening may take the form of surface texturing by mechanical means (sanding, bead blasting knurling, cutting, scoring), chemical means (acid etching), laser cutting, or as an integral part of the extruding or molding process.

Figure 113:
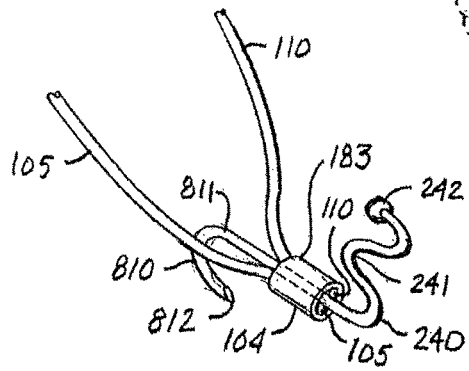
FIG. 113 illustrates a perspective view of one end of a filtering device where the retrieval feature includes a tissue engagement feature.

In addition to adding fixation or tissue engagement structures to the elongate bodies, the retrieval features may be attached to the elongate body or formed from the elongate body in a number of different ways that may also include a fixation element or elements. In one embodiment, there is a combined tissue anchor and retrieval feature joined to the first end or the second end of the first support member as shown in FIG. 113. FIG. 113 illustrates a distal end 104 where the elongate bodies 105, 110 terminate within the attachment element or securing feature 183. The securing feature may be a crimp 183 or any other suitable technique to join the elongate bodies together. Suitable means for attachment and attachment techniques used to create the attachment element or securing feature 183 include, by way of non-limiting examples, a crimp or other joining technique with a discrete detent, a swage or other joining technique with circumferential constriction, soldering, welding, brazing, shrink fit tubing, epoxy, multi-lumen collar where one wire is placed in each lumen and then bonded or melted together.

In this illustrative embodiment, the retrieval feature 240 is formed from a single wire 811 that is shaped into the curves 241 of the retrieval feature 240 as well as into a tissue engagement structure 810 having a tip 812 for engaging with tissue.

In this illustrative embodiment, the diameter of the wires used for the elongate bodies 105, 110 and the retrieval feature 240 are nearly the same so crimping the wires is suitable joining method. Other joining methods include, by way of non-limiting examples, a crimp or other joining technique with a discrete detent, a swage or other joining technique with circumferential constriction, soldering, welding, brazing, shrink fit tubing, epoxy, multi-lumen collar where one wire is placed in each lumen and then bonded or melted together.

Figure 114:
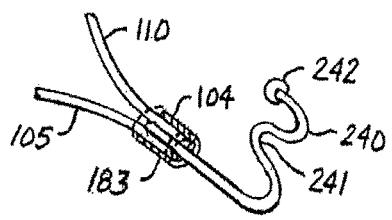
FIG. 114 illustrates a perspective view of one end of a filtering device where the retrieval feature terminates within the securing or attachment feature.
Figure 115:
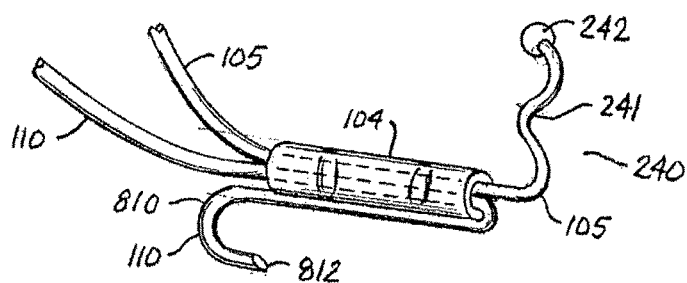
FIG. 115 illustrates a perspective view of one end of a filtering device where the retrieval feature terminates within the securing or attachment feature and the end of an elongate support structure is formed into a tissue engagement element.
Figure 116C:
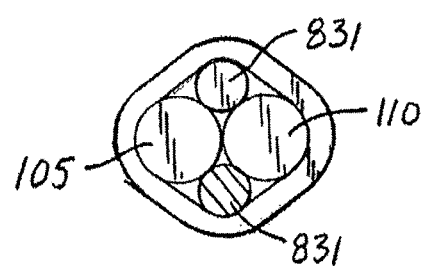
FIG. 116C is a section view through the securing or attachment feature of FIG. 16A where separate tissue engagement and retrieval features are provided rather than formed in the ends of the elongate support structures.

In the embodiment illustrated in FIG. 114, in contrast to the illustrated embodiment in FIG. 113, the wire used to form the retrieval feature 240 terminates within the securing feature or attachment element 183. Instead of using a separate wire as shown in FIGS. 113, 114, the ends of the elongate bodies 105, 110 may be used to form the retrieval feature 240 and a fixation element 810. This is an example of an end of the first support member forms a tissue anchor and an end of the second support member forms a retrieval feature. Additionally or alternatively, the retrieval feature formed on the end of the first support structure is formed from the first support structure or the retrieval feature formed on the end of the second support structure is formed from the second support structure. In some embodiments, a tissue anchor is on the end of the first support structure or the end of the second support structure. FIG. 115 illustrates the elongate body 105 passing through the crimp 183 and then being shaped into a retrieval feature 240. The elongate body 110 passes through the crimp 183 and then shaped into a distal opening fixation element 810 with tip 812. FIG. 116A is similar to FIG. 115 except that the elongate body 110 is used to form the retrieval feature 240 and the elongate body 105 passes through the crimp 183 and then being shaped into a proximal opening fixation element 810. FIG. 116B is a section view through the crimp 183. FIG. 116C is a section view of FIG. 116A with spacers 831 inserted into the crimp 183 to help distribute the crimp force and provide a more secure joint.

Figure 118:
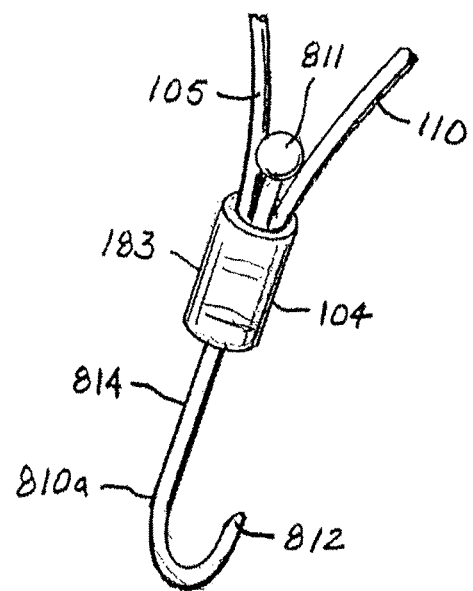
FIG. 118 is a perspective view of a separate tissue engagement feature that is joined to a filtering device using the securing or attachment feature.

Instead of adding a fixation element to an end, the end may be used to form a fixation or tissue engagement element. FIGS. 117A and 117B illustrate perspective and bottom views where a fixation element 852 is formed from the crimp 183 used to hold the elongate bodies 105, 110. Either elongate body 105, 110 may be used to form the retrieval feature 240. FIG. 118 illustrates an alternative embodiment having a wire 814 separate from the elongate bodies 105, 110. The wire 814 is formed into a fixation element 810a where a ball 811 prevents the wire 814 from pulling through the crimp 183. The fixation element 810a ends in a hook 812.

The modifications a retrieval feature to include a fixation element as described with regard to FIGS. 88, 89B, 90B, 96, 99, 113, 114, 115, 116-118 may also be used to provide one or more fixation elements to the retrieval feature embodiments described with regard to FIGS. 20-29. Additionally, while many of the illustrative embodiments have been described in conjunction with elongate bodies 105, 110 the invention is not so limited. Other elongate body and/or support structures described herein may also be used interchangeably with the elongate bodies 105, 110.

Figure 120:
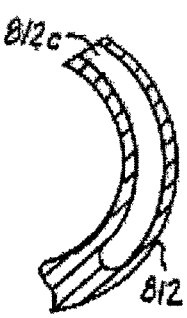
FIG. 120 illustrates an alternative embodiment of the tissue engagement element of FIGS. 93A and 93B with the addition of a hollowed tip portion.
Figures 121, 122:
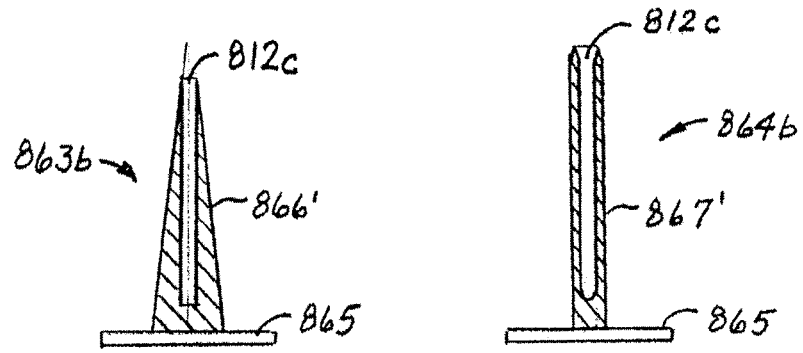
FIGS. 121 and 122 illustrate an alternative embodiments of the tissue engagement elements of FIGS. 111A and 111B with the addition of a hollowed tip portion.

In other alternative embodiments, all or a portion of the fixation element may be modified to include a pharmacological agent. The inclusion of a pharmacological agent may include coating all or a portion of the filter or tissue engagement structure with a pharmacological agent. Additionally or alternatively, the tissue engagement feature may be adapted and configured to contain a drug or combination of drugs or pharmacological agents that are released over time or after some initial time delay. FIG. 119 illustrates an alternative embodiment of the fixation element 812 in FIG. 98 with a hollowed end portion 812c. The drug eluting fixation element 814a may be formed using a hypodermic-like needle shaped into the desired curvature. Alternatively, the cavity 812c may be formed by hollowing out a portion of the interior a wire or by forming the fixation element 812 from a tube. Similarly, the tip of the fixation element in FIGS. 93A, 93B may be hollowed as shown in FIG. 120. FIG. 120 illustrates a cavity 812c in the distal end of the fixation element 812. The pins 867 and spikes 866 of FIGS. 110, 111A and 111B may also be modified to include a drug cavity as shown in FIGS. 121 and 122. FIG. 121 illustrates a tissue engagement feature 863b with a base 865 supporting a sloped body 866' that ends in a pointed tip. A cavity 812c extends from the tip into the body 866'. FIG. 122 illustrates a tissue engagement feature 864b with a base 865 supporting a generally cylindrical body 867' that ends in a flat tip. A cavity 812c extends from the flat tip into the body 867'. The cavities 812c may be filled with any of a wide variety of pharmacological agents. Examples include: anti-proliferative or anti-thrombogenic agents. Additionally, these or any other fixation element or tissue engagement structure embodiment may also be coated with a pharmacological agent.

FIGS. 123A, 123B and 124A-E illustrate the positioning and deployment of an embodiment of the filter device 900 of the present invention having one or more fixation or tissue engagement features 810. The filter device 900 is an exemplary embodiment of any one of the alternative filter structure embodiments described herein having tissue engagement or fixation elements.

Embodiments of the present invention may be partially deployed so that a user may confirm the position of the filter prior to completely deploying the device into the target lumen. Partial deployment involves the controlled and reversible deployment and engagement of one or more fixation elements. The engagement is reversible because after placing the filter into the lumen the filter may be pulled partially or completely into the sheath as described herein. The filter may be repositioned and then redeployed into the lumen so that the fixation elements engage the lumen walls. Additionally, the design of embodiments of the filter of the present invention allow the retrieval action to be accomplished by approaching the filter from the same direction used for deployment. All the steps of positioning, deployment and recovery may be performed from a single access site.

Figure 123A:
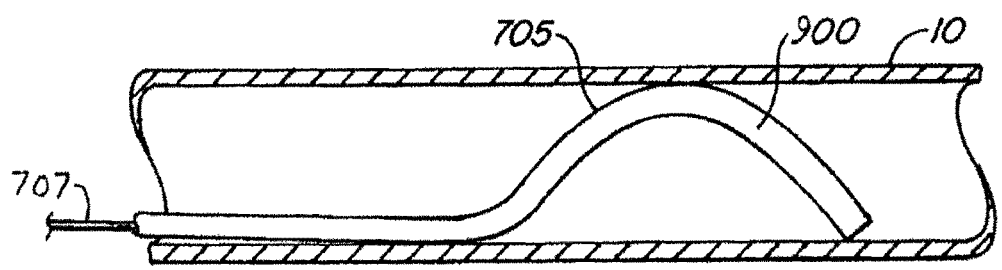
FIGS. 123A and 123B illustrate a perspective view of a filter device within a lumen and positioned for deployment where the filter device is stowed in a deployment sheath (FIG. 123A). The filter device is shown in phantom in the view illustrated in FIG. 123B.
Figure 123B:
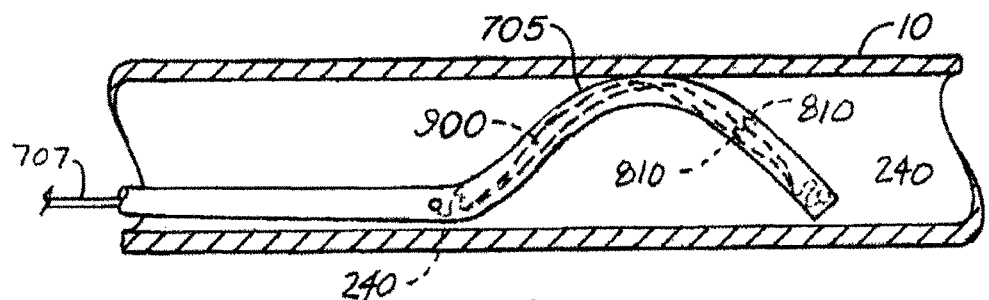

The device 900 may be loaded into an intravascular delivery sheath 705 as shown in FIGS. 123A, 123B and as described above with regard to FIG. 69. Using conventional endoluminal and minimally invasive surgical techniques, the device 900 can be loaded into the proximal end of the sheath 705, before or after advancing the sheath 705 into the vasculature, and then advanced through the sheath using a conventional push rod. The push rod 707 is used to advance the device 900 through the delivery sheath 705 lumen as well as fix the position of the device (relative to the sheath 705) for device deployment. In one preferred technique, the device 900 is loaded into the proximal end of a delivery sheath that has already been advanced into a desired position within the vasculature (FIG. 123B). The device 900 may be pre-loaded into a short segment of polymeric tubing or other suitable cartridge that allows the device 900 to be more readily advanced through a hemostasis valve.

When used with a compliant delivery sheath 705, the pre-formed shape of the device 900 deforms the sheath 705 to conform to the device shape (FIG. 123A, 123B). Accordingly, a flexible, compliant sheath 705 assumes the curvature of the stowed device 900. The deformation of the delivery sheath 705 helps stabilize the position of the sheath 705 in the vasculature and facilitates accurate deployment of the device 900 to the intended delivery site. In contrast, a non-compliant delivery sheath 705 (i.e., a sheath that is not deformed to conform to the preformed shape of the device 900) maintains a generally cylindrical appearance even through the device 900 is stowed within it (FIG. 69C). Regardless of the type of sheath used, device delivery is accomplished by using the push rod 707 on the proximal side of the device 900 to fix the position of the device within the sheath 705 and then withdrawing the sheath 705 proximally. As the device 900 exits the distal end of sheath 705, it assumes the pre-formed device shape.

The symmetrical device shape (see e.g., devices in FIGS. 15, 16A, 96, 97, 90C, 99, and 88), facilitates the deployment and retrieval of the device 900 from multiple access points in the vasculature. As with other non-fixation filter devices described herein, a device 900 may be positioned as shown in the vasculature within the inferior vena cava 11 immediately below the renal veins 13 (see FIG. 70). A femoral access path (FIG. 126A) and a jugular access path (FIG. 125A) are illustrated. The femoral access path and a jugular access path may each be used for device deployment, repositioning and retrieval. Alternatively, the vena cava could be accessed via brachial or antecubital access for device deployment, repositioning and retrieval. The placement and orientation of the fixation elements or tissue engagement structures may be modified as needed to facilitate the desired placement and retrieval technique.

Retrieval of the devices is most preferably accomplished by endoluminal capture using one of the retrieval features described herein. (i.e., FIGS. 27A-E) The retrieval features described herein have been designed to work well using a commercially available snares two of which are illustrated in FIG. 71A and FIG. 71B. The single loop gooseneck snare 712 is illustrated in FIG. 71 inside of a recovery sheath 710. The multiple loop Ensnare 714 is illustrated in FIG. 71B inside of a recovery sheath 710. These conventional snares are controlled by a physician using a flexible, integral wire.

Figure 125A:
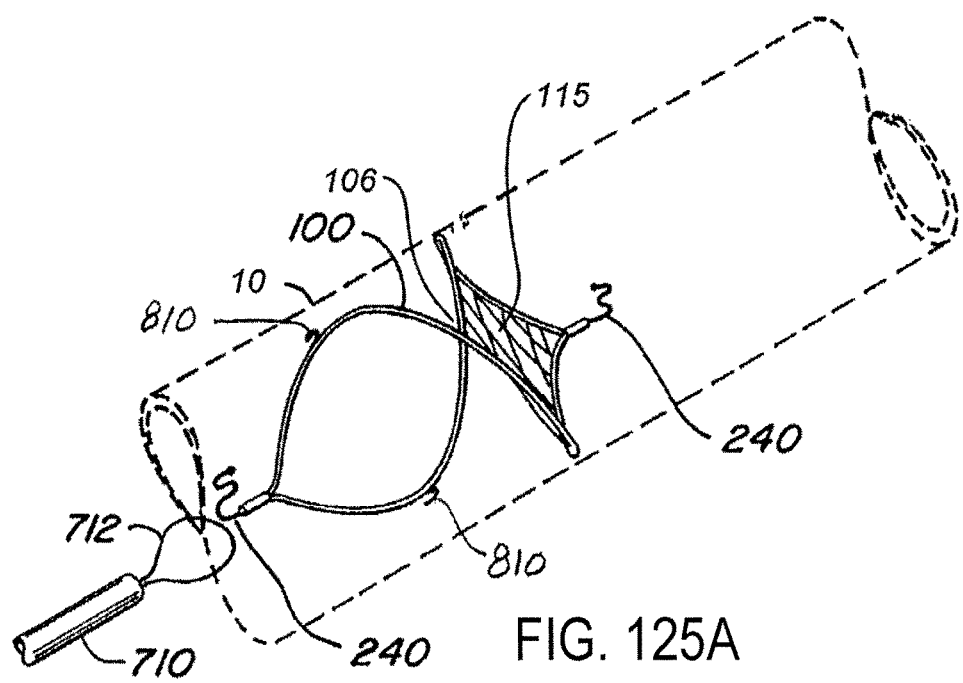
FIGS. 125A-C illustrate one approach and recovery sequence for retrieving a deployed filtering device.
Figure 125B:
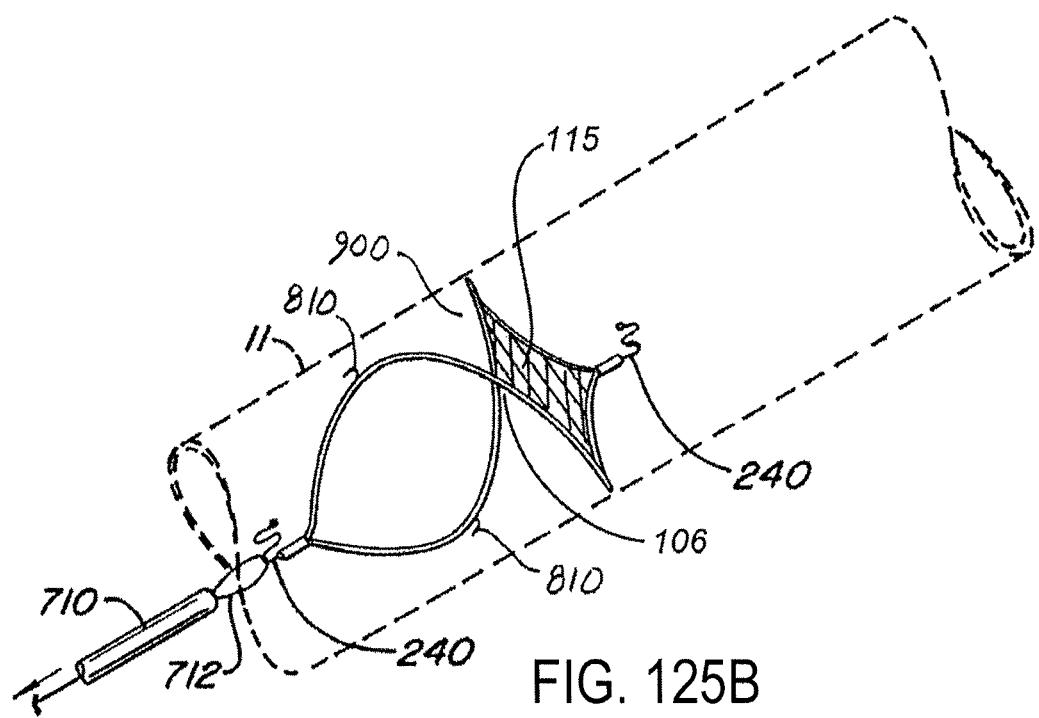
Figure 125C:
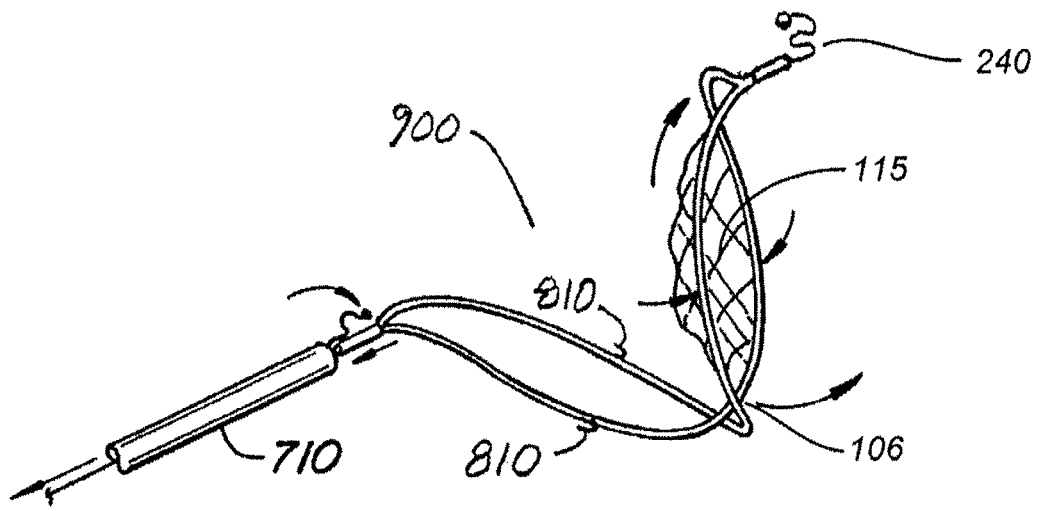
Figure 126A:
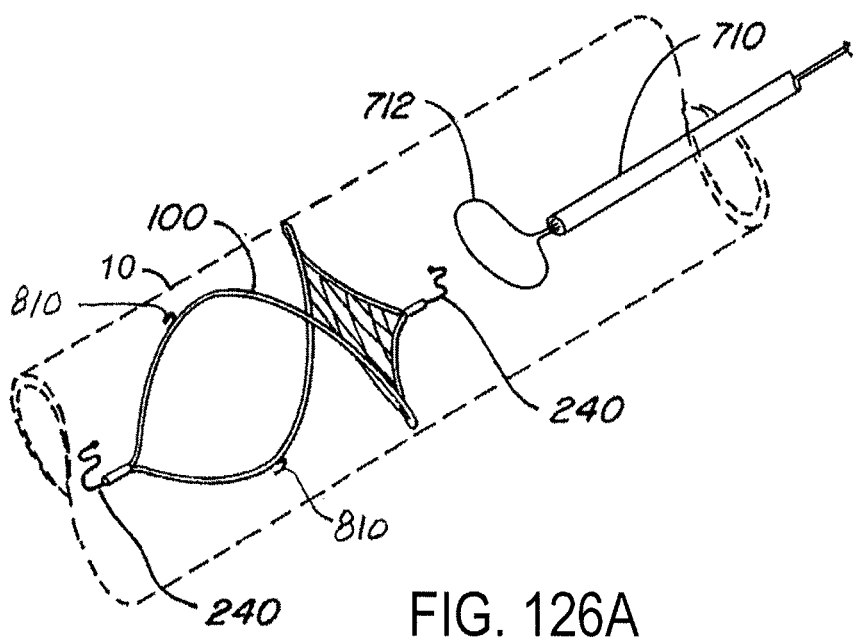
FIGS. 126A-D illustrate one approach and recovery sequence for retrieving a deployed filtering device.
Figure 126B:
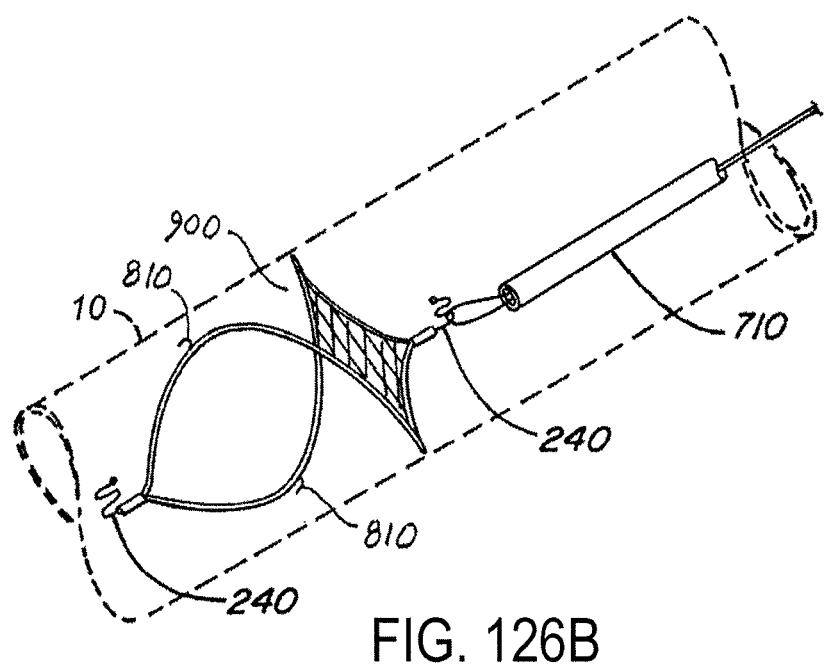
Figure 126C:
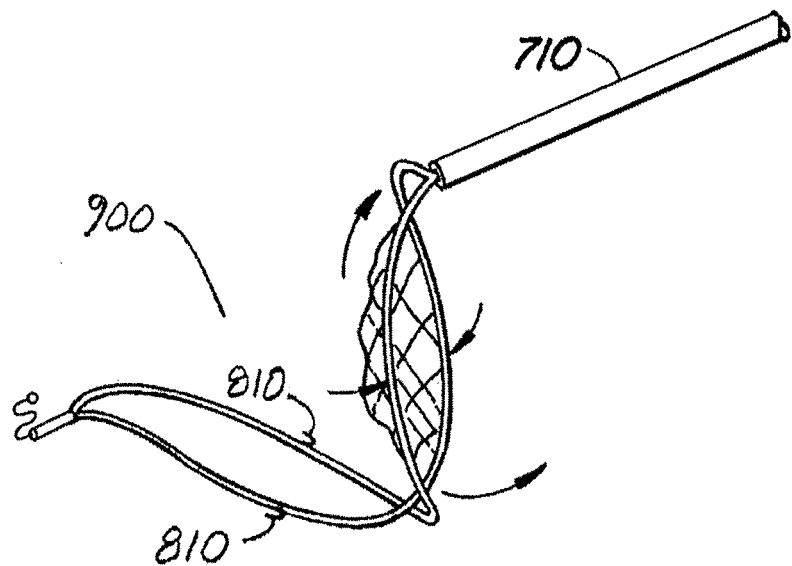

The sequence of device recapture and removal from a body lumen is illustrated and described above with reference to FIGS. 72A-C. A similar recovery sequence is used for embodiments of filter device 900 as illustrated in FIGS. 125A-125C. In this discussion, the device 900 is positioned in the vena cava. FIGS. 125A, 125B, and 125C illustrate an exemplary jugular recovery. The device 900 is illustrated within the vessel so that flow within the vessel initially passes through the material capture structure and then through the open support frame. FIGS. 126A-C illustrate an exemplary femoral recovery. The device 900 is illustrated within the lumen so that flow within the lumen initially passes through the material capture structure and then through the open support loop. A collapsed snare is advanced via a delivery sheath to the proximity of the retrieval feature 240. Once in place, the snare 712 is exposed and assumes a pre-defined expanded loop shape (FIGS. 125A and 126A). The loop shape is placed over the retrieval feature 240 as illustrated in FIGS. 125B and 126B. Advantageously, retrieval features of the present invention are positioned relative to and in contact with the luminal wall so that the feature may be more easily captured by a retrieval device such as a snare.

Figure 126D:
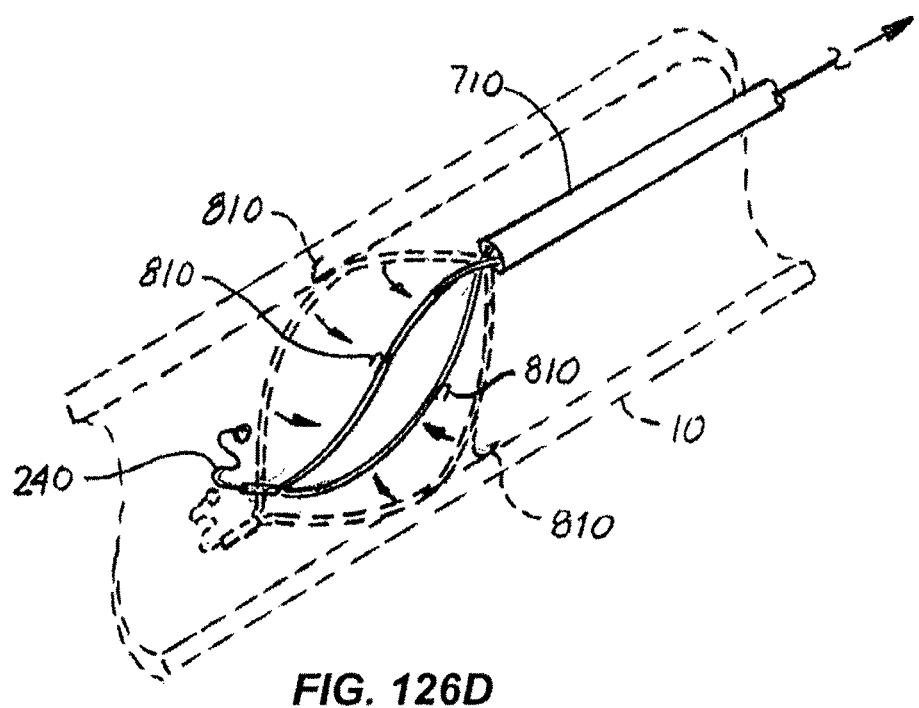

The snared device 900 can then be either pulled into the sheath 710, or alternatively and more preferably, the recovery sheath 710 is advanced over the device 900 while maintaining positive control of the snare 712 as the sheath 710 advances over the device 900. Advancing the recovery sheath 710 over the device 900 facilitates atraumatic removal of the device 900 from any tissue that has grown in or around the device 900. Additionally, the retrieval action, which tends to collapse the device radially inward (FIGS. 125C and 126C), also facilitates removal from any tissue layer formed on the device while also withdrawing the fixation elements from the lumen wall. Moreover, recovering the filtering device by pulling on a portion of the filter structure (i.e., a retrieval feature) removes the opposing spiral elements and the fixation elements or tissue engagement structure attached to them from the lumen wall. As the device 900 is drawn into the sheath 710, the pre-formed shape of the device 900 also urges the support members away from the lumen wall which also assists in retracting or disengaging fixation elements from the lumen wall (FIG. 126D).

Figure 124A:
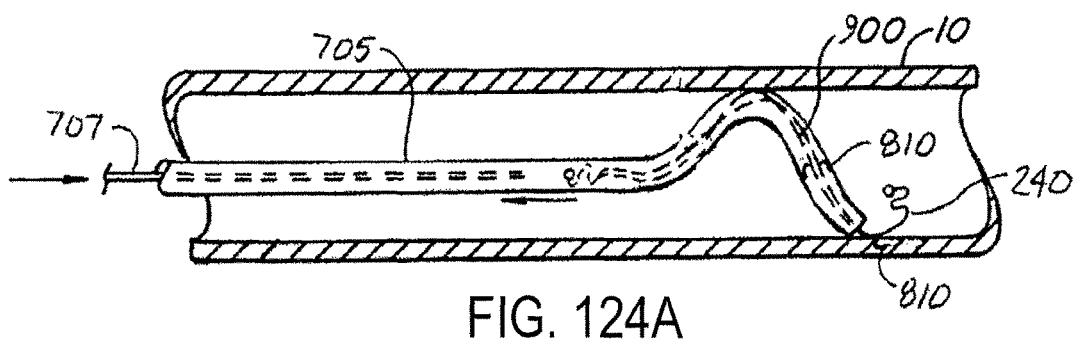
FIGS. 124A-124E illustrate an exemplary positioning and filter deployment sequence.
Figure 124B:
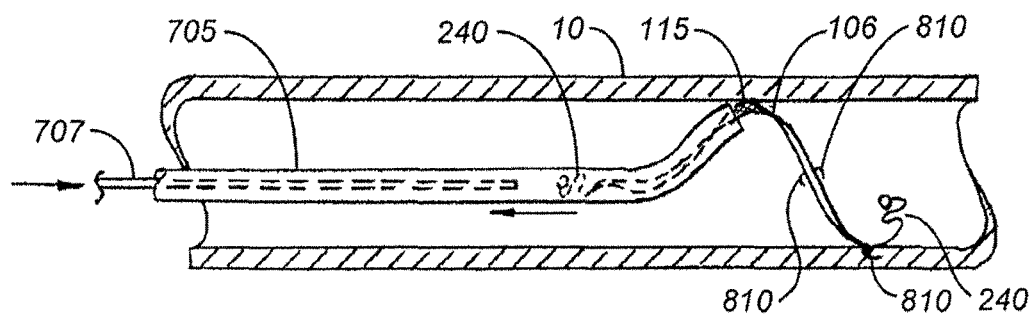
Figure 124C:
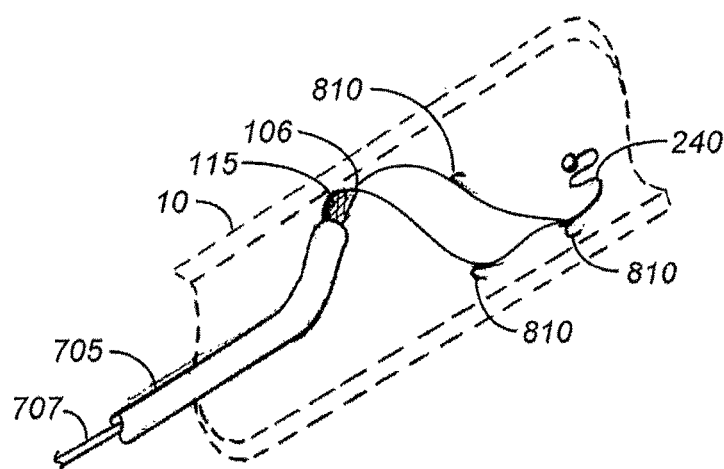

Having discussed the various techniques and alternatives for positioning, deploying and retrieving a filter, a method of positioning a filter within a lumen will now be described. FIGS. 123A and 123B illustrate an embodiment of a step of advancing a sheath containing a filter through a lumen. FIG. 124A illustrates an embodiment of a step of deploying a portion of the filter from the sheath into the lumen to engage the lumen wall with a fixation device while maintaining substantially all of a material capture structure of the filter within the sheath. As shown in FIG. 124A, the retrieval feature 240 and at least one fixation element 810 have exited the sheath 705. The remainder of the filter including the material capture structure is still inside the sheath 705. Next, as shown in FIGS. 124B and 124C, is an embodiment of a step of deploying a support frame from the sheath to a position along and engaged with the lumen. The support frame is also used to engage fixation elements with the lumen walls. The shape and design of the support frame itself generates radial forces that also assist in securing the filter into position and maintaining the position of the filter within the lumen. FIG. 124C illustrates the support frame deployed from the sheath 705 and opened along the lumen 10. Two fixation elements 810 are shown engaged the lumen wall. The crossover 106 is also deployed. A portion of the material capture structure 115 adjacent the crossover 106 is also shown exiting the sheath.

Figure 124D:
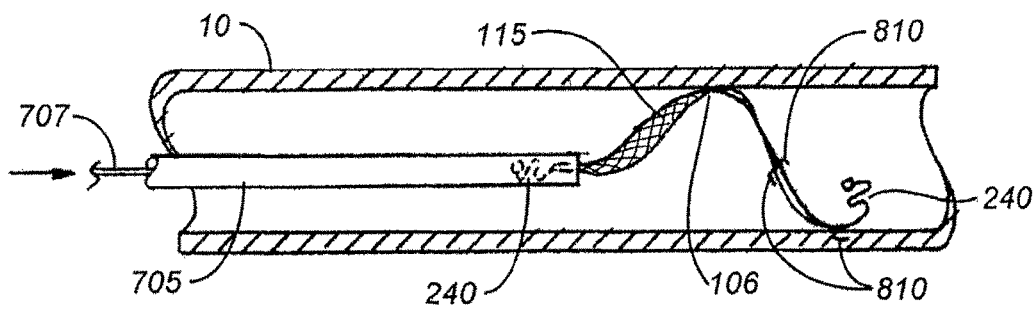

Next is the step of deploying the material capture structure of the filter from the sheath into a position across the lumen. FIG. 124D illustrates the material capture structure exiting the sheath. A retrieval feature 240 is still inside of the sheath (shown in phantom).

Figure 124E:
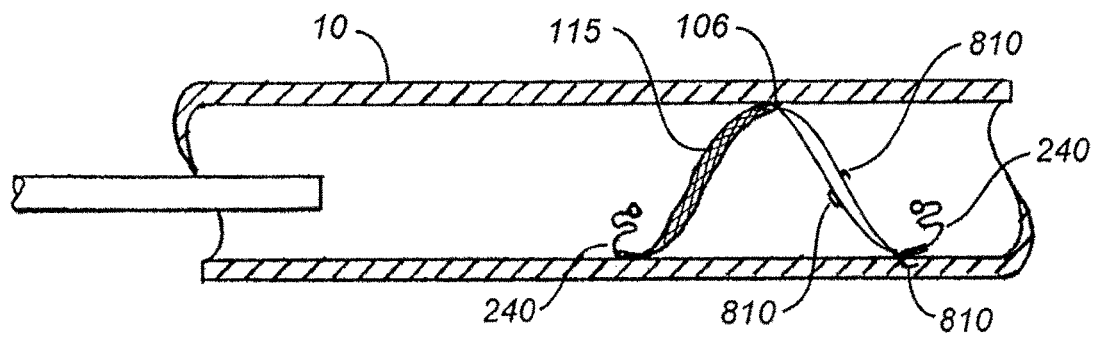

FIG. 124E illustrates the fully deployed filter 900. The second retrieval feature 240 is in position against the lumen wall and the material capture structure is deployed across the lumen. FIG. 124E also illustrates an embodiment of the step deploying a filter retrieval feature 240 from the sheath 710 after the step of deploying another portion of the filter step.

In one embodiment, the filter illustrated in FIG. 124E could be modified to include a fixation element 810 on or near both retrieval features 240. In such an embodiment, as the last portion of the filter and the second retrieval feature exists the sheath 710 (the movement from FIG. 124D to 124E), another fixation element 810 at or near the second retrieval feature engages the lumen wall.

In another aspect, the method of positioning a filter may include the step of deploying a crossover structure of the filter into the lumen before or after the deploying the material capture structure of the filter step. One aspect of this step is illustrated in FIGS. 124B and 124C. These two views illustrate the partially deployed filter 900 having one retrieval feature and three engagement elements 810 out of the sheath 710 and into contact with the lumen. Additionally in this illustration, the crossover 106 has exited the sheath 710. In this stage of deployment, the engagement feature 240 is against one lumen wall, the crossover 106 is against another wall generally opposite to the retrieval feature 240. The deployed open support frame extends along the lumen between the crossover 106 and the engagement feature 240.

The collapsible nature of the filters of the present invention allows for filter recovery from the same direction that the filter was deployed as well as recovery from the opposite direction the filter was deployed. Embodiments of the filters of the present invention also reliably position retrieval features against the lumen wall to present in a way that is easy to snare. A filter may be deployed into the inferior vena cava using a femoral access route. Then that same filter may be recovered using an access route from the jugular or the superior vena cava as shown in FIG. 125A. Similarly, a filter placed into the vena cava using a jugular deployment route may be removed using a femoral approach as shown in FIG. 126A. In one specific example, the recovery is accomplished by maneuvering a snare towards the filter in the same direction used during the advancing step described above. Next, there is the step of engaging the snare with a filter retrieval feature positioned against a wall of the lumen. In an alternative technique, there is the step of maneuvering a snare towards the filter in the opposite direction used during the advancing step. Next, there is the step of engaging the snare with a filter retrieval feature positioned against a wall of the lumen.

The techniques for filter placement and recovery may be modified in other ways as well. For example, a method of positioning a filter as described above may be adjusted to include the step of deploying a filter retrieval feature from the sheath before the deploying a portion of the filter step. In another alternative, the step of placing the filter retrieval feature against the lumen wall may be performed before or after the positioning of a crossover within the lumen. Additionally or alternatively, the step of deploying a filter retrieval feature may also include placing the filter retrieval feature against the lumen wall.

Additionally, repositioning the filter 900 from one lumen position to another is accomplished in a similar fashion as described above with regard to FIGS. 74A-74D. Many embodiments of the device 900 have at least one atraumatic end such as illustrated in the non-limiting examples of FIGS. 90C, 91, 99, 96, 97, 94, 89C, 89A, and 88. In this context an atraumatic end is one that does not have any fixation or tissue engagement features. Because of the atraumatic design of these filter device embodiments, repositioning of the filter device 900 may be accomplished by fully recapturing (see FIG. 74C) or only partially recapturing (FIG. see 74B) the device 900 into a recovery sheath 710. By maintaining the portion of the device 900 having fixation elements contained within the sheath 710, the atraumatic end may be moved into the desired position and confirmed in position before deploying the remainder of the device and engaging the fixation elements. The atraumatic design of the device 900 allows the device to partially deploy such that only the atraumatic end is in the lumen. The partially deployed device may then be pulled along the lumen wall into the desired position. Once in position, the remainder of the device is then released from the sheath thereby allowing the fixation elements to engage with the lumen walls as they are freed from the sheath. The delivery sheath and recovery sheath are provided with the same reference numbers since filter devices of the present invention may be deployed into and recovered from the vasculature using sheaths that are about the same size. As such, devices of the present invention may be deployed into the vasculature from a delivery sheath having a first diameter. Then, the device may be retrieved from the vasculature using a recovery sheath having a second diameter no more than 2 Fr larger than the first diameter (1 Fr=0.013"=⅓ mm). Alternatively, the second diameter may be no more than 1 Fr larger than the first diameter or, alternatively, the first diameter is about the same as the second diameter.

While many of the features and alternative designs of fixation elements and tissue engagement structures have been shown and described with regard to FIGS. 88-125, it is to be appreciated that the invention is not so limited. The features and alternative embodiments described in FIGS. 83A-87 may also be applied to the various filters with fixation elements and tissue engagement structures. Additionally, the filters and embodiments described with regard to FIGS. 2A, 2B, 2C, 6C, 7D, 7G, 9A-10B, 11-19, 64A-67, 69A-87 may also be adapted to include any of the fixation elements or tissue engagement structures described or illustrated in FIGS. 88-126D.

Delivery Device with Securement Feature

In some embodiments, as illustrated in FIG. 127A-127C, a delivery catheter 1200 can include a retractable outer shaft 1202 or sheath and an inner shaft 1204 or sheath disposed coaxially within the outer shaft 1202. The inner shaft 1204 can have a distal tracking tip 1206 and can have a lumen for receiving a guidewire 1208. Secured to the inner shaft 1204 is a securement device 1210 that engages the proximal retrieval feature 1214 of the filter 1212, which is stowed at the distal end of the delivery catheter 1200. The securement device 1210 can be an outwardly biased clip, as illustrated, that is held in a closed position by the outer sheath 1202. As long as a portion of the outer sheath 1202 remains disposed over the biased clip, the securement device remains in a closed position and stays engaged with the proximal retrieval feature of the filter. When the outer sheath 1202 is fully retracted off of the biased clip, the outward bias of the clip moves the clip outwardly and away from the inner shaft to an open position that releases the securement device 1210 from the proximal retrieval feature 1214 of the filter 1212. The securement device 1210 allows the operator to recapture the filter at any time during the deployment of the filter so long as the securement device 1210 is kept in the closed position. Therefore, the operator may retract the outer sheath 1202 up to the securement device 1210 to partially deploy the filter 1212 within the lumen while maintaining secure attachment between the securement device 1210 and the retrieval feature 1214. If the initial deployment is not adequate and/or the position of the filter needs to be adjusted, the operator can recapture the filter 1212 by advancing the outer sheath 1202 back over the filter. The delivery catheter 1200 can then be manipulated and its position adjusted for a subsequent redeployment of the filter. Once the operator is satisfied with the positioning and orientation of the partially deployed filter, the outer sheath 1202 can be fully retracted past the securement device 1210 to release the filter.

In some embodiments, the delivery catheter 1200 can have one or more markings or detents on a handle, outer sheath, and/or inner sheath to indicate the different stages of deployment, such as ¼ deployment, ½ deployment, ¾ deployment and full deployment, where retracting the outer sheath to the full deployment marker means that the distal end of the outer sheath has been fully retracted from the securement device 1210. Alternatively or additionally, the coefficient of friction of the telescoping handle can be altered for each stage of deployment, so that the user perceives a level of resistance at each stage of deployment.

In some embodiments, the securement device 1210 can be outwardly biased such that the securement device 1210 automatically releases the retrieval feature of the filter by swinging open when the outer sheath is 1202 is fully retracted from the securement device. The biased securement device 1210 can take a variety of forms, such as a biased clip or hook illustrated in FIGS. 128A and 128B. The biased hook can swing out to an angle α, which can be at least about 30, 45, 60, 75, or 90 degrees. FIGS. 129A and 129B illustrate a similar embodiment of the securement device 1210, except that this embodiment has two clips or hooks. Other embodiments, may have more than two hooks.

Figure 130A:
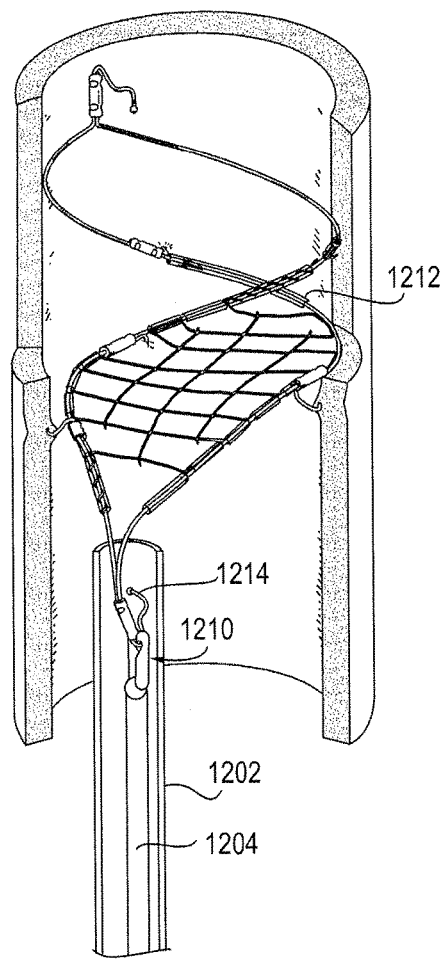
FIGS. 130A and 130B illustrate yet another embodiment of a securement device.
Figure 130B:
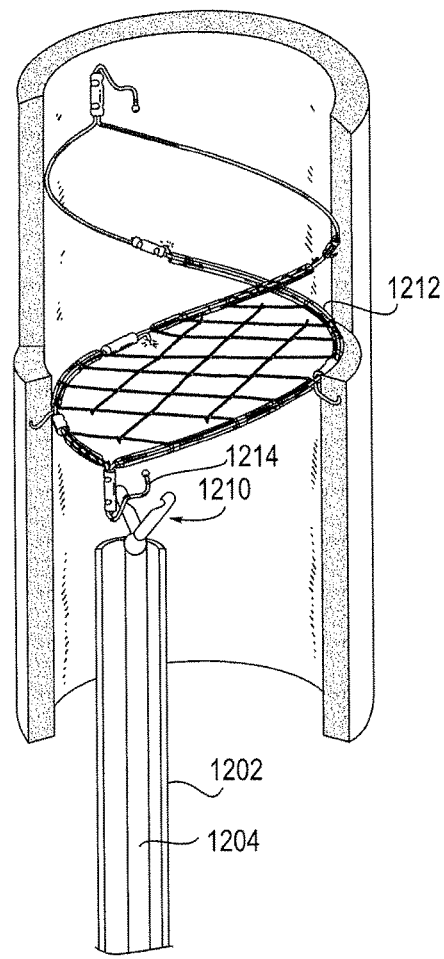

FIGS. 130A and 130B illustrate another embodiment of a securement device 1210, which can be biased outwardly for automatic release or can be actuated for release on demand. In this embodiment, the securement device 1210 can have a jaw configuration that can clamp onto the retrieval feature of the filter. The jaw can have a lower jaw portion and an upper jaw portion that can be outwardly biased such that the jaw must be covered by the sheath to retain the jaw in the closed configuration and clamped to the retrieval feature 1214 of the filter 1212. When the outer sheath 1202 is fully retracted from the jaw, the upper and lower jaw portions pivot or move apart to release the retrieval feature. In other embodiments, the jaw may be actuated by the user to open and close the jaw. For example, the jaw may have one or more wires connected to the jaw portions for actuating the jaws between an open configuration and a closed configuration.

Figure 131A:
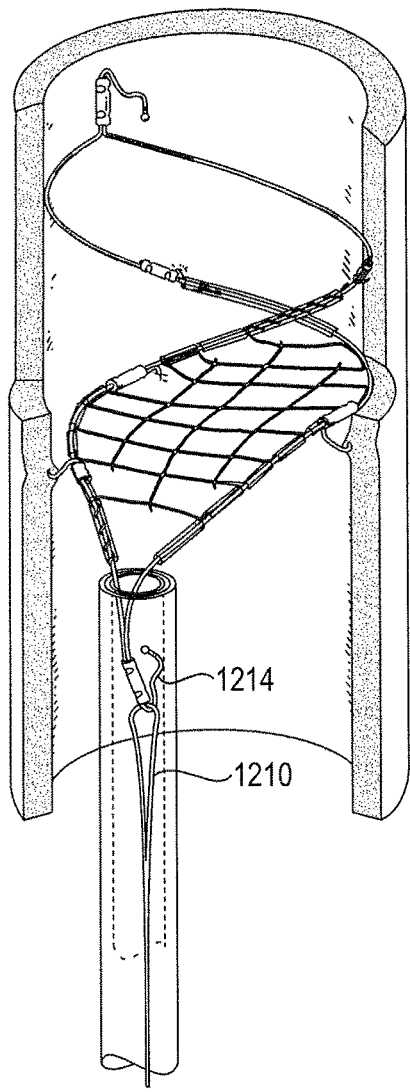
FIGS. 131A and 131B illustrate another embodiment of a securement device.
Figure 131B:
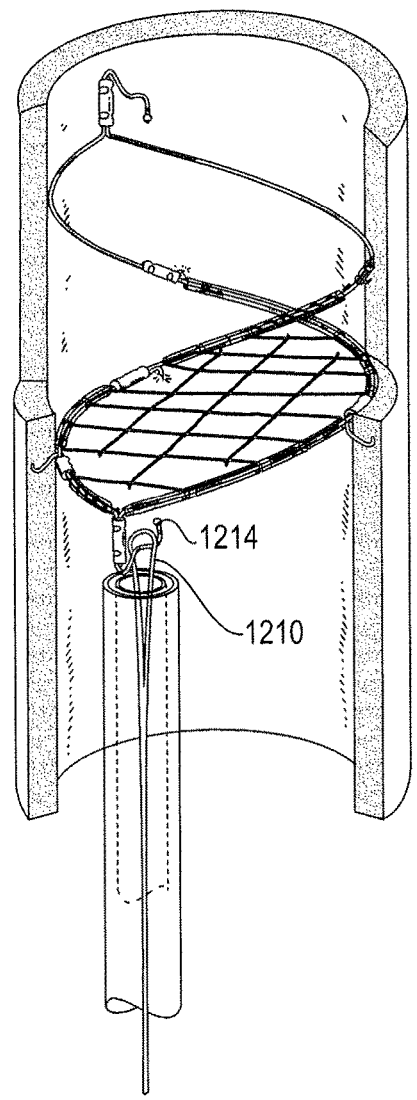

FIGS. 131A and 131B illustrated a user actuated securement device 1210 that is a loop or tether of suture, wire or string. The loop may have two free ends that can extend proximally out of the proximal portion of the delivery catheter. The loop can be maintained under tension around the retrieval feature 1214 in order to securely retain the filter within the delivery catheter until full deployment is desired. To enable full deployment of the filter and release of the retrieval feature from the loop, one free end of the loop can be pulled while the other free end can be released. The end of the loop can be pulled until the loop has been unraveled from the retrieval feature. Alternatively, the loop or tether can be cut using a user actuated blade, scissors or cutting device to free the filter. In some embodiments, the loop or tether can be metallic doped with an upright deflection capability, which can be provided by biasing the metallic doped tether or loop upwards and away from the retrieval feature. In some embodiments, the loop or tether can be a pre-shaped metallic wire loop, which can also be biased upwards away from the retrieval feature, that releases from the retrieval feature once the sheath is pulled completely away from the retrieval feature.

In some embodiments, the securement device, which can be a wire loop, tether, hook, or clip for example, can be made of a shape memory metal, such as nitinol, that can hold onto and secure the retrieval feature until the loop or tether is heated past a transition temperature, which can be greater than body temperature. The securement device can be heated by, for example, running an electrical current through the securement device, thereby causing the securement device to transition to a release configuration, such as a deflected configuration that moves away from the retrieval feature.

Figure 132A:
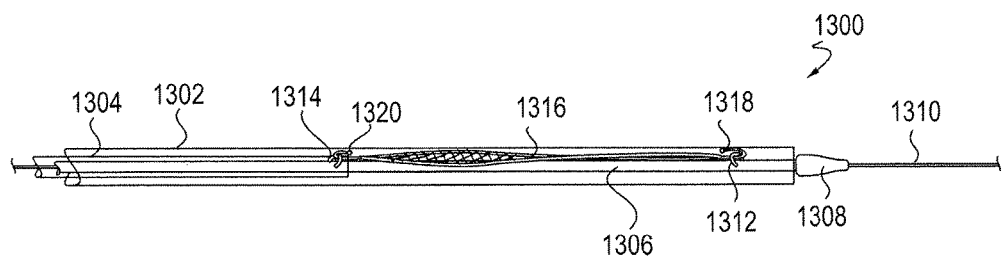
FIGS. 132A-132C illustrate an embodiment of a telescoping delivery device with a dual release mechanism.
Figure 132B:
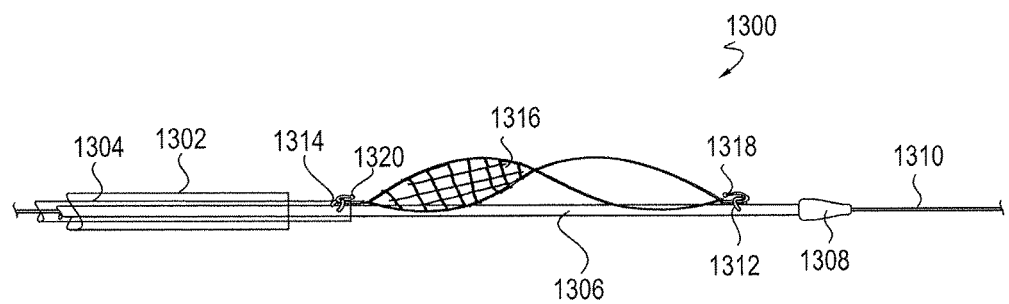
Figure 132C:
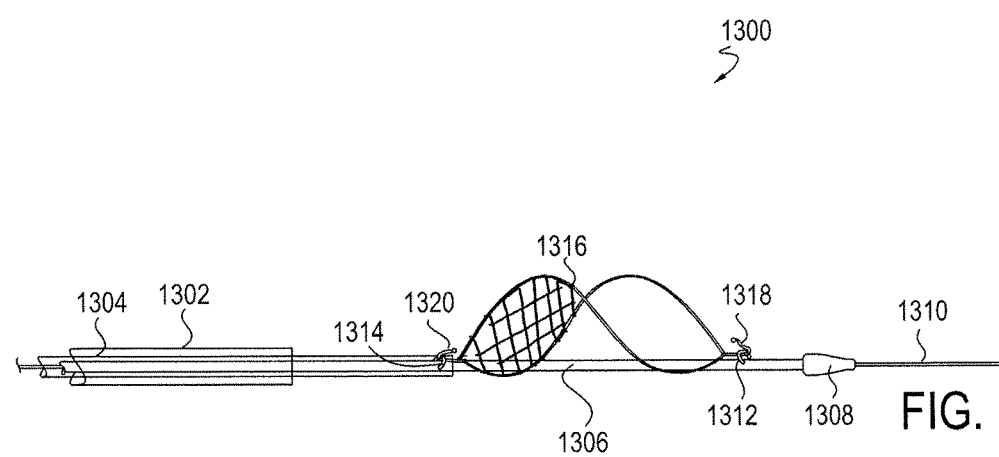

FIGS. 132A-132C illustrate an embodiment of a telescoping delivery catheter 1300 with dual release. The telescoping delivery catheter 1300 can have a retractable outer sheath 1302, an inner sheath 1304 disposed within the outer sheath, and a guidewire sheath 1306 disposed within the inner sheath 1304. The guidewire sheath can have a distal end with a tracking tip 1308 and can have a lumen for receiving a guidewire 1310. The distal end of the guidewire sheath 1306 can have a distal securement device 1312 and the distal end of the inner sheath 1306 can have a proximal securement device 1314. The filter 1316 can be secured to the telescoping delivery catheter 1300 by using the distal securement device 1312 to engage the distal retrieval feature 1318 of the filter and by using the proximal securement device 1314 to engage the proximal retrieval feature 1320. This configuration allows the filter to be completely unsheathed from the delivery catheter while remaining secured to the delivery catheter, allowing the operator to position the filter in the desired location and configuration before releasing the filter from the delivery catheter, as further described below.

The distal and proximal securement devices 1312, 1314 can both be user actuated securement devices, such as the loop type device that uses a suture or wire. For loop type devices, the securement device can include the suture or wire and a port, such that the suture or wire can be threaded through the lumen of the shaft or sheath, through the port, around the retrieval feature, and back through the port and into the lumen. In some embodiments, the distal securement device 1312 can be user actuated while the proximal securement device 1314 can be either user actuated or biased to automatically release the retrieval feature when the sheath is completely retracted off the securement device. If the proximal securement device 1314 is a biased type device with automatic release, the outer sheath 1302 should be maintained over the proximal securement device 1314 until the filter 1316 is correctly placed and full deployment is desired, and this cover should be maintained even while the inner sheath 1304 is advanced or retracted with respect to the guidewire sheath 1306. To ensure coverage, the outer sheath 1302 can be retracted up to the proximal securement device 1314 to expose most of the filter, and then the outer sheath 1302 and inner sheath 1304 can be moved back and forth in tandem. In some embodiments, the outer sheath 1302 and the inner sheath 1304 can be locked together to ensure tandem movement. If both securement devices are user actuated, the outer sheath 1302 can be completely retracted without prematurely deploying the filter.

The ability to telescope the inner sheath 1304 relative to the guidewire sheath 1306 allows an additional degree of control during filter deployment. By advancing the inner sheath 1304 in the distal direction, the filter is shortened longitudinally while increasing in diameter, thus the telescoping feature allows the length and diameter of the filter to be controlled during deployment. This may be advantageous to do when deploying the filter in a large lumen in order to ensure that the anchors on the filter properly engage the lumen wall. The telescoping feature also allows precise control on where the proximal and distal ends of the filter are deployed. Once the desired positioning of the filter is achieved, the securement devices 1312, 1314 can be actuated to release the filter.

The telescoping delivery catheter 1300 can have markings or detents on the various sheaths or shafts and handle to indicate the various deployment stages, or can have varied or altered levels of coefficient of friction, as described above.

The following embodiments provide examples of guided pullback systems that can be used for delivery of the devices described herein. Traditionally, the implants described herein can be deployed using a pin-pull method which involves pinning or maintaining the position of a portion of the delivery system, for example, an inner sheath to keep the implant in an advanced position, and pulling back another portion of the delivery system, for example, an outer sheath to expose the implant at a desired implant site. Such methods are traditionally performed by a clinician by hand. A clinician would have one hand on the portion of the delivery system to be 'pinned' (e.g., inner sheath) and another hand on the portion of the delivery system to be 'pulled'. Performing such a procedure by hand can tend to cause the two portions to become misaligned. As such, the pulling action can be out of axis, putting friction on any sliding mechanism, and making the deployment of the implant more difficult. Misalignment can also provide a risk of damaging the shaft components by requiring excessive force to compensate for the increased frictional force. The following embodiments provide systems capable of performing the pinning and pulling in axis, which can remove the element of human error introduced by a clinician attempting the same method by forcing the components to remain in alignment. Forced alignment can reduce frictional force caused by misalignment. As noted above, reduced frictional force can provide a smoother pullback motion for the clinician. The systems provided herein can also include ergonomic and simple to use mechanics, aiding in ease of use.

Figure 133A:
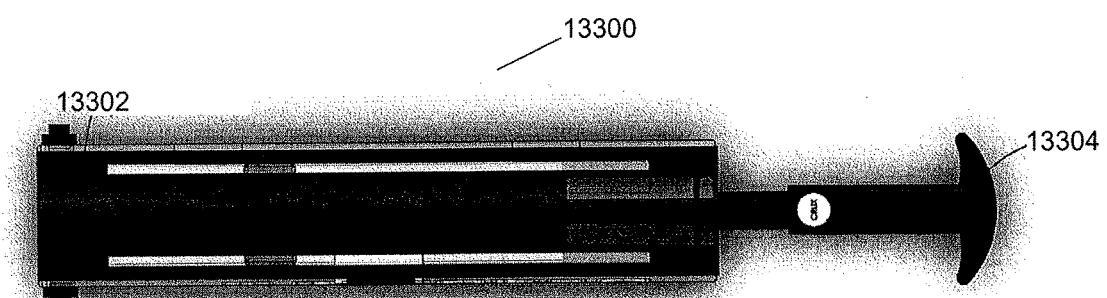
FIGS. 133A-C illustrate an embodiment of a pullback system.
Figure 133B:
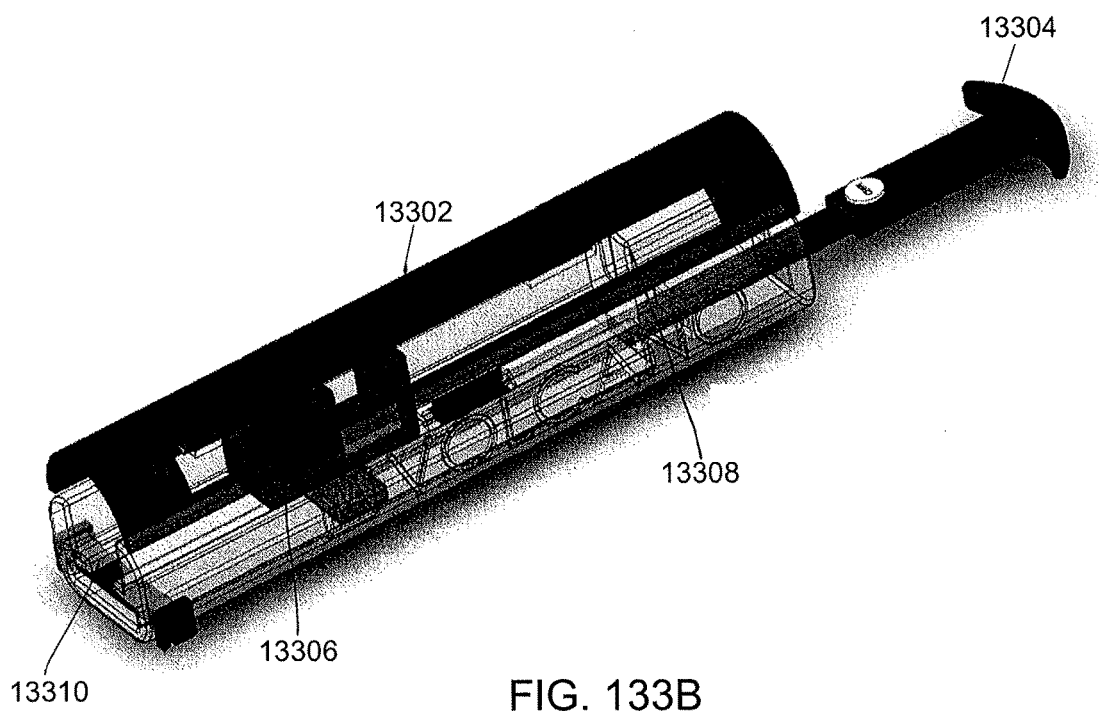
Figure 133C:
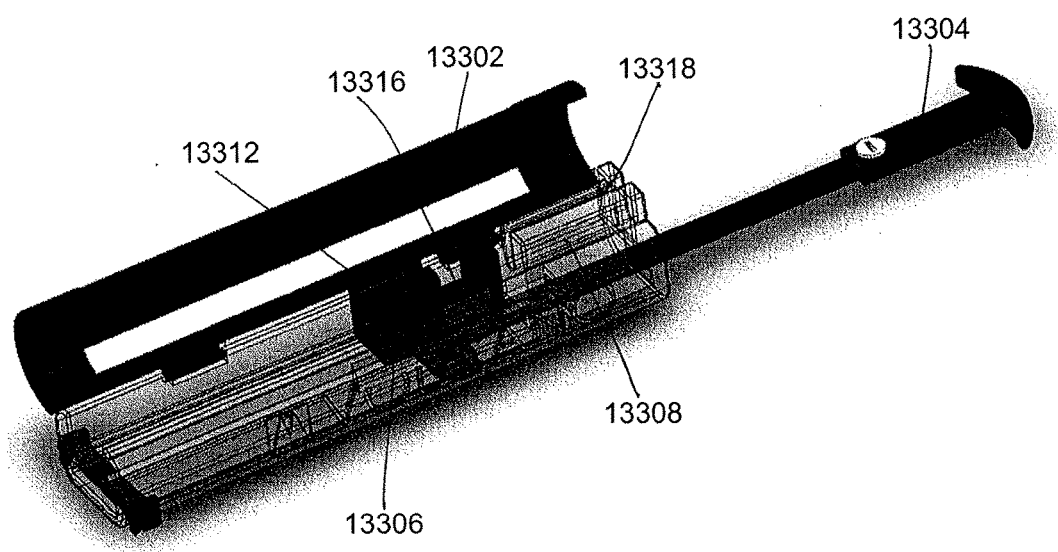

FIGS. 133A-C illustrate an embodiment of a guided pullback system 13300 that can be used with existing delivery catheter systems. FIG. 133A illustrates a top view of the system 13300, including cover 13302 and pullback grip 13304. The cover can be hinged or attached in another way, for example, using screws. FIG. 133B illustrates a perspective view of the system 13300. FIG. 133B illustrates the cover 13302 and pullback grip 13304. Also shown is sliding clip 13306 which can be moved relative to fixed clip 13308 by pulling on the pullback grip 13304. The sliding clip 13306 moves along rail 13310. FIG. 133C illustrates a perspective view of the system 13300 with the cover 13302 lifted up and the sliding clip 13306 pulled back towards the fixed clip 13308.

Figure 134:
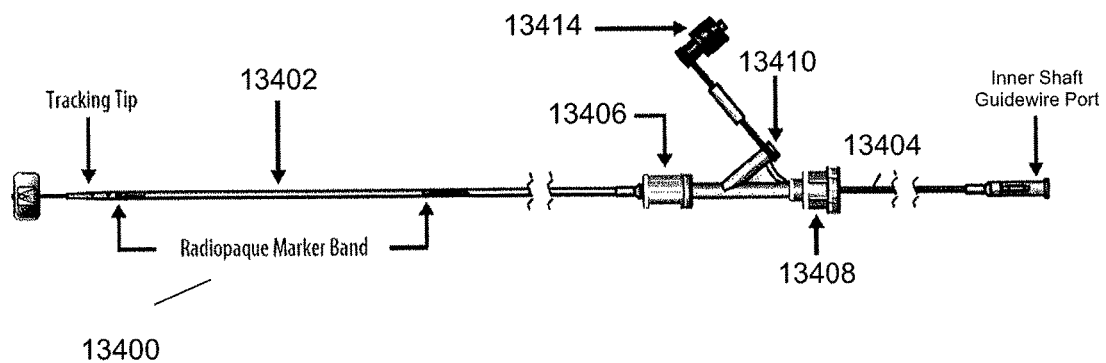
FIG. 134 illustrates an embodiment of a delivery catheter.

The system 13300 can be used as an attachment over existing delivery systems. For example, the system 13300 can be used with the delivery system shown in FIG. 134. The delivery catheter 13400 can include an outer shaft 13402 and an inner shaft 13404. The inner shaft 13404 can include a lumen for inserting, for example, a guidewire. The outer shaft 13402 can include an outer shaft handle 13406, a hemostasis valve 13408 and a flush port 13410. A check valve 13414 can be attached to the flush port 13410.

The delivery catheter 13400 can be used with the pullback system 13300. The delivery catheter 13400 can be placed into the system 13300. A component of the outer sheath 13402, for example, the hemostasis valve 13408, can be placed into the sliding clip 13306. The sliding clip 13306 can include a channel 13312 or groove for accepting the outer sheath 13402. The sliding clip 13306 can also include a recess or other features 13316 to receive or mate to a feature of the outer sheath. For example, recess 13316 can be shaped to accept hemostasis valve 13408. The outer sheath components can be fixed to the sliding clip 13306 using an interference fit. A component of the inner sheath 13404 can be placed into the fixed clip 13308. The fixed clip includes a groove or channel 13318 to accept components of the inner sheath. The grooves or recesses on the clip can allow anything (e.g., flush line) connected to the implant to remain connected during pullback. An interference fit can hold the inner sheath in place within the fixed clip. Other methods of attachment to the sliding and/or fixed clips are also possible.

An implant (e.g., the filter described herein) can be positioned at a distal end of the catheter, as described elsewhere herein. To deploy the filter, a clinician can pull back on the pullback grip 13304. This action moves the sliding clip 13306 with the attached outer shaft 13402 towards the fixed clip 13308 and attached inner sheath 13404, holding the inner sheath in place to maintain the position of the filter at the distal end of the catheter 13400, while retracting the outer sheath to expose the filter. Because the system 13300 maintains the clips 13306, 13308, and thus, the outer shaft 13402 and inner sheath 13404 in line during deployment, the delivery can be a smoother, easier motion than that in a delivery performed by hand.

FIG. 135A-E illustrate another embodiment of a pullback system 13500. The system 13500 can be lightweight and small with an external shell design. The system 13500 can be disposable. The design of system 13500 can allow for ease of manufacturing and compatibility with existing commercial delivery system.

Figure 135A:
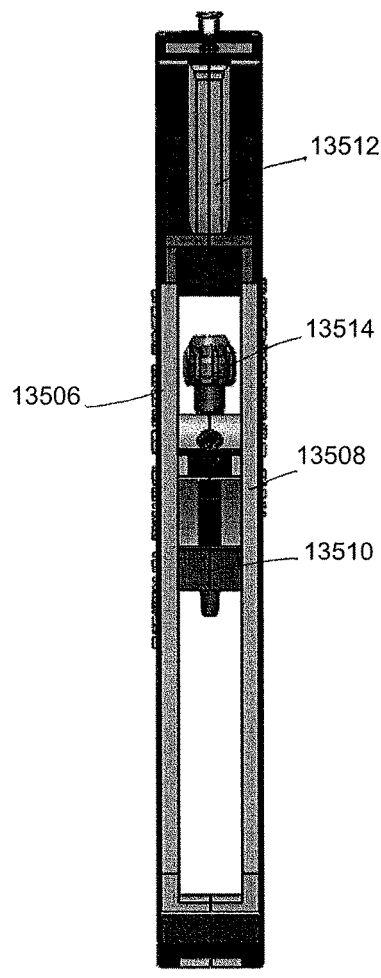
FIGS. 135A-E illustrate another embodiment of a pullback system.
Figure 135B:
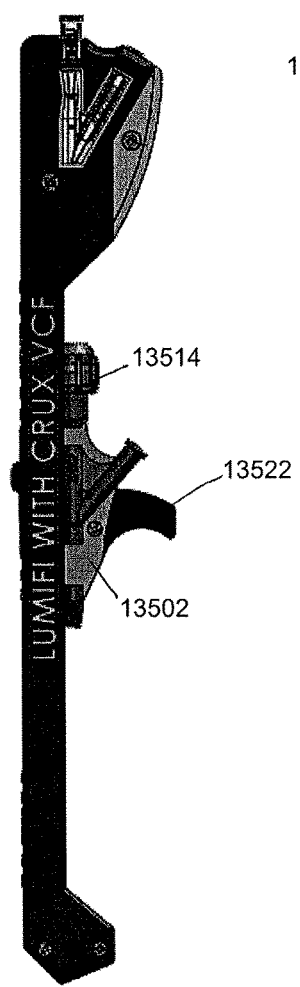
Figure 135C:
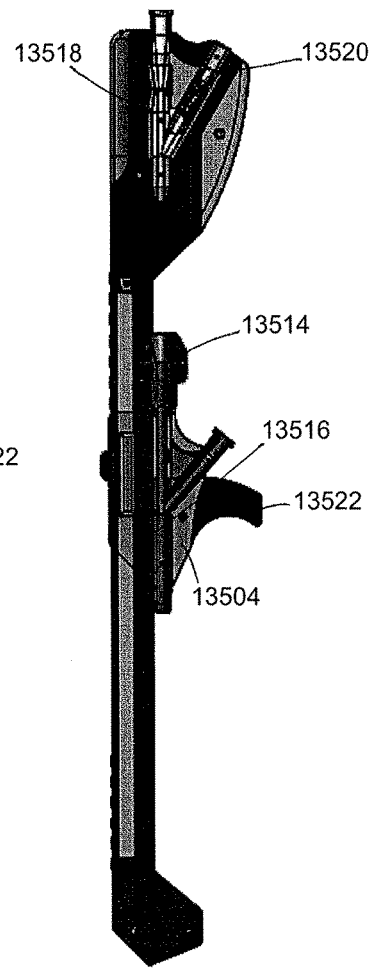

The system 13500 can comprise multiple pieces configured to snap over or be otherwise attached around (e.g., using screws) a delivery catheter system. In this embodiment, the system 13500 comprises 4 pieces, but systems having more or fewer pieces are also possible. The top view of FIG. 135A shows two pieces 13506, 13508 which provide the rail system. The side views of FIGS. 135B and 135C show the two other pieces 13502, 13504, which can enclose components of the outer sheath (e.g., the hemostasis valve).

Once assembled, the device comprises a sliding clip 13510 and a fixed clip 13512, similar to those described with respect to system 13300. The sliding clip 13510 can be configured to receive a portion of the outer sheath 13402 of the delivery catheter 13400. The sliding clip 13510 can include features configured to receive features of the outer sheath 13402. For example, a portion 13514 of the clip 13510 can be configured to receive the hemostasis valve 13408. A portion of the clip 13510 can be formed into a recess or lumen 13516 configured to receive a portion of the outer sheath. Fixed clip 13512 can comprise a recess or other feature configured to receive a portion of the inner sheath 13404 through lumen 13518. The system 13500 also includes a lumen 13520 configured to allow access to inner sheath, for example for inserting or removing a guidewire.

Figure 135D:
Figure 135E:
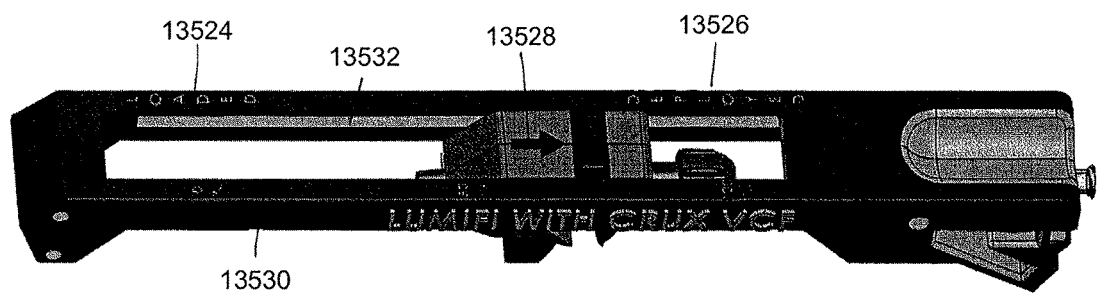

As shown in FIG. 135E, eliding clip 13510 can be pulled back using pullback grip 13522. Pulling back sliding clip 13510 moves it along rail 13532 relative to fixed clip 13512. With the delivery catheter 13400 positioned within system 13500, the pulling motion can retract the outer sheath 13402, while holding the inner sheath 13404 in place, as described above with respect to pullback system 13300. The side view of FIG. 135D shows the system 13500 in a loaded position, in which the filter or other implant is loaded within the delivery catheter prior to deployment. FIG. 135E shows the system 13500 in a deployed position. As shown in FIG. 135E, the system 13500 can include a 'loaded' indicator 13524 and a 'deployed' indicator 13526 to increase ease of use. An arrow 13528 can also be included to help with ease of use of the system. FIG. 135E also shows a scale 13530 that can be used to indicate an amount or proportion of the length of the filter deployed at a given pullback point. In some embodiments, the scale can provide additional information, for example, individual anchor deployment points, securement device position, etc.

In some embodiments, the pullback systems described herein can employ mechanisms such as wheels, gears, or wires to control a pullback rate. Such features can help a clinician avoid moving too quickly or slowly during deployment. In some embodiments, the rails comprise locking features to help control the pullback rate. For example, the rail can comprise multiple tracks that require shifting of the sliding clip to continue with the pullback. The pullback systems described herein can be electrically powered or otherwise automated. Such automated systems can also provide for smooth pullback. Electronic control of the pullback can provide consistent deployment force, deployment rate, and/or allow one-handed deployment.

While the systems have been described as pullback systems, it will be appreciated that similar systems could instead utilize a push mechanic from an end of the rail. For example, the outer sheath could be held in place using a fixed clip, and the inner sheath could be pushed forward using a sliding clip.

Pullback systems, such as those described herein, can include safety features to prevent accidental deployment. For example, in some embodiments, the rail can include a notch. This notch can serve to stop any accidental pullback by requiring a greater force to overcome the notch and continue with pullback.

It will be appreciated that the pullback systems described herein can also be used for delivery of implants other than those described herein, and can be used with delivery catheters other than those described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A delivery catheter for deploying and retrieving an implant with a proximal retrieval feature and a distal retrieval feature, the delivery catheter comprising:
    an outer sheath having a lumen configured to collapse the implant;
    an inner sheath slidably disposed within the lumen of the outer sheath, the inner sheath having a lumen;
    a guidewire sheath slidably disposed within the lumen of the inner sheath, the guidewire sheath having a lumen configured to receive a guidewire;
    a distal securement device attached to a distal end of the guidewire sheath, the distal securement device is positionable between a closed configuration for grasping the distal retrieval feature and an open configuration for releasing the distal retrieval feature, wherein the distal securement device is configured to engage the distal retrieval feature of the implant: and
    a proximal securement device attached to a distal end of the inner sheath, the proximal securement device is positionable between a closed configuration for grasping the proximal retrieval feature and an open configuration for releasing the proximal retrieval feature, wherein the proximal securement device is configured to engage the proximal retrieval feature of the implant;
    wherein the proximal and distal securement devices are relatively positionable in opposite directions with respect to each other for collapsing a previously-deployed implant.

2. The delivery catheter of claim 1, wherein both the proximal securement device and the distal securement device are user actuated.

3. The delivery catheter of claim 1, wherein the proximal securement device comprises a loop of suture or wire and a port in the inner sheath, and the distal securement device comprises a loop or suture or wire and a port in the guidewire sheath.

* * * * *